(12) United States Patent
Pierce et al.

(10) Patent No.: US 10,279,184 B2
(45) Date of Patent: May 7, 2019

(54) DEVICES AND METHODS FOR TREATING CARDIOVASCULAR AND METABOLIC DISEASE

(71) Applicants: Ryan Kendall Pierce, San Francisco, CA (US); Benjamin Kahn Cline, Palo Alto, CA (US)

(72) Inventors: Ryan Kendall Pierce, San Francisco, CA (US); Benjamin Kahn Cline, Palo Alto, CA (US)

(*) Notice: Subject to any disclaimer, the term of this patent is extended or adjusted under 35 U.S.C. 154(b) by 205 days.

(21) Appl. No.: 15/101,748

(22) PCT Filed: Dec. 8, 2014

(86) PCT No.: PCT/US2014/069096
§ 371 (c)(1),
(2) Date: Jun. 3, 2016

(87) PCT Pub. No.: WO2015/088972
PCT Pub. Date: Jun. 18, 2015

(65) Prior Publication Data
US 2016/0303381 A1  Oct. 20, 2016

Related U.S. Application Data

(60) Provisional application No. 61/913,388, filed on Dec. 9, 2013.

(51) Int. Cl.
*A61B 18/14* (2006.01)
*A61N 1/365* (2006.01)
(Continued)

(52) U.S. Cl.
CPC ........ *A61N 1/36564* (2013.01); *A61B 5/0215* (2013.01); *A61B 17/1204* (2013.01);
(Continued)

(58) Field of Classification Search
CPC ........... A61B 2018/00011; A61B 2018/00404; A61B 2018/00267; A61B 2018/00345;
(Continued)

(56) References Cited

U.S. PATENT DOCUMENTS 7,925,352 B2  4/2011  Stack et al.
8,290,595 B2  10/2012  Kieval et al.
(Continued)

FOREIGN PATENT DOCUMENTS

WO  WO2010035271  4/2010

OTHER PUBLICATIONS

International Search Report and Written Opinion of the International Searching Authority for International Patent Application No. PCT/US2014/069096, dated Mar. 31, 2015 (14 pages).
(Continued)

*Primary Examiner* — Jaymi E Della
(74) *Attorney, Agent, or Firm* — Merchant & Gould P.C.

(57) ABSTRACT

Devices and methods described herein may, among other uses, favorably cause the activation and/or deactivation of vascular baroreceptors in order to achieve a desired impact on a physiological condition, such as baroreflex-regulated conditions, hypertension, hypotension, nervous system disorders, metabolic disorders, cardiovascular disease, heart failure, cardiac arrhythmia, renal disease, respiratory disease, diabetes, and insulin resistance. The devices and methods may be used in concert with each other and/or other treatments, medications, interventions, or behavioral regimens. They may also be used in concert with devices and methods that perform or assist with assessing or measuring a mammal's blood pressure assessing, measuring, or predicting the impact of the described methods and devices on the patient's condition (including blood pressure), and/or protecting the surrounding anatomy from adverse effects.

14 Claims, 42 Drawing Sheets

(51) Int. Cl.

| | |
|---|---|
| *A61B 5/0215* | (2006.01) |
| *A61F 2/92* | (2013.01) |
| *A61F 2/82* | (2013.01) |
| *A61B 17/3207* | (2006.01) |
| *A61F 2/88* | (2006.01) |
| *A61F 2/91* | (2013.01) |
| *A61M 25/10* | (2013.01) |
| *A61B 17/12* | (2006.01) |
| *A61B 18/18* | (2006.01) |
| *A61F 2/915* | (2013.01) |
| *A61F 2/06* | (2013.01) |
| *A61B 17/221* | (2006.01) |
| *A61B 17/22* | (2006.01) |
| *A61B 18/00* | (2006.01) |
| *A61B 18/02* | (2006.01) |
| *A61N 7/00* | (2006.01) |
| *A61M 25/06* | (2006.01) |

(52) U.S. Cl.
CPC .. *A61B 17/12109* (2013.01); *A61B 17/12136* (2013.01); *A61B 17/320725* (2013.01); *A61B 18/1492* (2013.01); *A61B 18/1815* (2013.01); *A61F 2/82* (2013.01); *A61F 2/885* (2013.01); *A61F 2/91* (2013.01); *A61F 2/92* (2013.01); *A61M 25/10* (2013.01); *A61B 17/221* (2013.01); *A61B 2017/22067* (2013.01); *A61B 2018/00011* (2013.01); *A61B 2018/0022* (2013.01); *A61B 2018/00214* (2013.01); *A61B 2018/00267* (2013.01); *A61B 2018/00345* (2013.01); *A61B 2018/00404* (2013.01); *A61B 2018/00791* (2013.01); *A61B 2018/00994* (2013.01); *A61B 2018/0212* (2013.01); *A61F 2/915* (2013.01); *A61F 2002/068* (2013.01); *A61F 2002/825* (2013.01); *A61F 2002/91533* (2013.01); *A61F 2250/0031* (2013.01); *A61M 25/1011* (2013.01); *A61M 2025/0681* (2013.01); *A61M 2025/1015* (2013.01); *A61M 2025/1052* (2013.01); *A61N 2007/0043* (2013.01)

(58) Field of Classification Search
CPC ...... A61B 2018/00212; A61B 18/1492; A61B 5/0215
See application file for complete search history.

(56) References Cited

U.S. PATENT DOCUMENTS

| | | | |
|---|---|---|---|
| 8,548,600 B2 | 10/2013 | Deem et al. | |
| 2007/0255379 A1* | 11/2007 | Williams | A61M 5/14276 607/120 |
| 2010/0023088 A1* | 1/2010 | Stack | A61N 1/0558 607/44 |
| 2010/0211131 A1* | 8/2010 | Williams | A61N 1/056 607/44 |
| 2010/0292527 A1 | 11/2010 | Schneider et al. | |
| 2011/0218524 A1* | 9/2011 | Cattaneo | A61B 18/22 606/12 |
| 2012/0172680 A1* | 7/2012 | Gelfand | A61N 1/3627 600/301 |

OTHER PUBLICATIONS

Peter et al., "Fluid Structure Interaction with Contact Surface Methodology for Evaluation of Endovascular Carotid Implants for Drug-Resistant Hypertension Treatment," Journal of Biomechanical Engineering, Apr. 2012, pp. 041004-1-041004-10, vol. 134.

\* cited by examiner 1832    1838

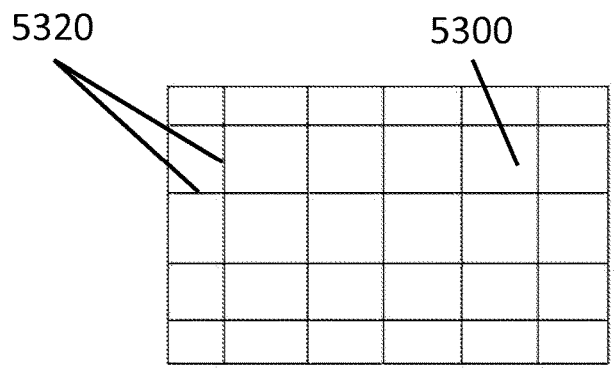
FIG. 53
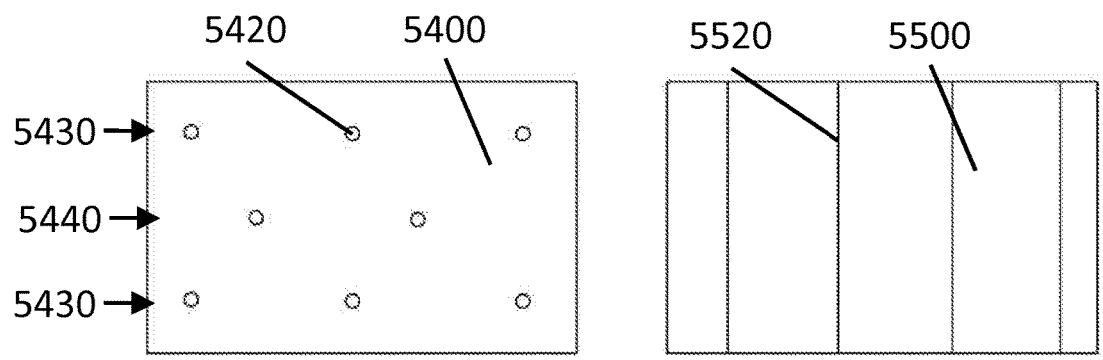
FIG. 54
FIG. 55
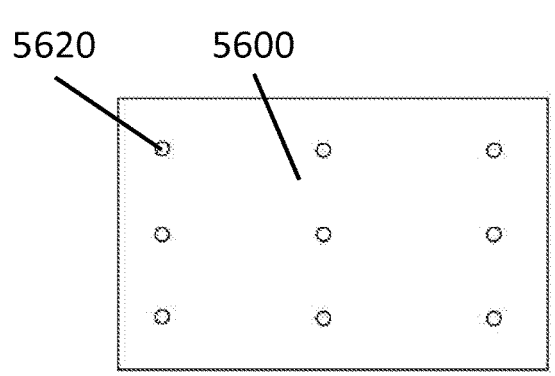
FIG. 56
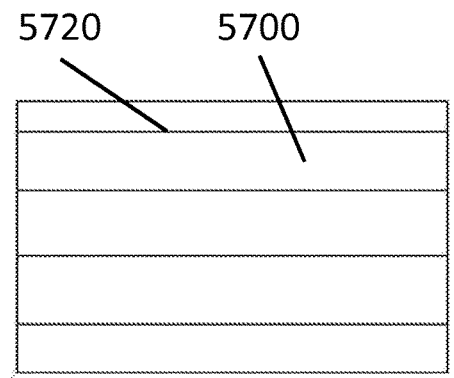
FIG. 57

DEVICES AND METHODS FOR TREATING CARDIOVASCULAR AND METABOLIC DISEASE

CROSS-REFERENCE TO RELATED APPLICATION

This application is the national stage application of International Patent Application No. PCT/US2014/069096, filed Dec. 8, 2014, and entitled "DEVICES AND METHODS FOR TREATING CARDIOVASCULAR AND METABOLIC DISEASE," which claims priority to, and the benefit of, U.S. Provisional Application No. 61/913,388, filed Dec. 9, 2013, both of which are hereby incorporated by reference in their entirety for all purposes.

BACKGROUND

Baroreceptor-mediated physiological processes and parameters, such as blood pressure, are related to a number of conditions that adversely affect millions of people. One such condition, hypertension, can contribute to heart failure, coronary heart disease, kidney failure, and other health problems, and is a leading indirect cause of morbidity and mortality. Existing drugs, devices, and methods of treatment for these conditions have proven inadequate or ineffective in many patients. It is therefore desirable to provide novel devices and methods to address these conditions.

SUMMARY

In one aspect of the present invention, a method of stimulating a baroreceptor in an artery of a patient may involve: applying a first amount of force to a region of a wall of the artery with a baroreceptor activation device implanted in the artery to stretch a baroreceptor in the wall during a first local blood pressure of a cardiac cycle within the artery; and applying a second amount of force to the region of the wall of the artery with the baroreceptor activation device during a second local blood pressure of the cardiac cycle within the artery. With this method, the first local blood pressure is lower than the second local blood pressure, and the first amount of force is less than the second amount of force.

In some embodiments, the baroreceptor activation device applies the first and second amounts of force at spaced-apart locations along the region of the wall of the artery, and the baroreceptor activation device includes at least one longitudinal strut and multiple connecting members attached to the strut(s) for applying the first and second amounts of force at the spaced-apart locations. In some embodiments, applying the first and second amounts of force involves applying more force at the spaced-apart locations where the connecting members reside than at locations between the connecting members. In some embodiments, the first amount of force is approximately zero force.

In some embodiments, the first and second local blood pressures are within the a lower and an upper quartile, respectively, of local blood pressures occurring within the cardiac cycle. In some embodiments, applying the first and second amounts of force further involves applying longitudinally varied amounts of force along a length of the baroreceptor activation device, where the first and second amounts of force are averages of the longitudinally varied amounts of force. In some embodiments, the method may further involve advancing the baroreceptor activation device into the artery through one or more blood vessels of the patient, using a delivery catheter and releasing the baroreceptor activation device from constraint within the delivery catheter to allow it to expand to contact the wall of the artery and apply the first and second amounts of force.

Some embodiments of the method may further involve advancing the baroreceptor activation device into the artery through one or more blood vessels of the patient, using a delivery catheter and expanding the baroreceptor activation device with the delivery catheter to cause it to contact the wall of the artery and apply the first and second amounts of force. In some embodiments, the baroreceptor activation device applies the first and second amounts of force asymmetrically to the wall of the artery, with a greater amount of force applied to a first circumferential portion of the wall and a lesser amount of force applied to a second circumferential portion of the wall. For example, the baroreceptor may reside in the first circumferential portion. In some embodiments, applying the first and second amounts of asymmetric force may involve expanding the baroreceptor device in an asymmetric cross-sectional shape.

In one embodiment, the artery is an internal carotid artery, and the region of the artery comprises a portion of the internal carotid artery at or adjacent a carotid sinus. In such embodiments, stimulating the baroreceptor may reduce systemic blood pressure in the patient. In some embodiments, the region of the artery is located within approximately 2 centimeters of a bifurcation of a common carotid artery into the internal carotid artery and an external carotid artery. In some embodiments, the method may further involve expanding the baroreceptor activation device to a non-circular cross-sectional shape within the artery.

The method may also optionally involve reducing strain in the wall of the artery, using the baroreceptor activation device. Reducing the strain, for example, may involve increasing an effective stiffness of the wall of the artery. The method may also optionally involve allowing a portion of the baroreceptor device to resorb within the artery over time. Such an embodiment may also optionally involve reducing strain in the wall of the artery with a non-resorbable portion of the baroreceptor activation device. In various embodiments, the first and second amounts of force may each include a longitudinally directed force component, a torsional force component, and/or a circumferential force component. In some embodiments, the first blood pressure occurs and the first amount of force is applied during a diastolic portion of a heart cycle of the patient, and the second blood pressure occurs and the second amount of force is applied during a systolic portion of the heart cycle.

In another aspect, a method of stimulating a baroreceptor in an internal carotid artery of a patient to reduce blood pressure in the patient may involve: advancing a baroreceptor activation device through a common carotid artery into an internal carotid artery, where the baroreceptor activation device comprises at least one longitudinal strut and multiple connecting members attached to the at least one longitudinal strut. The method may further involve deploying the baroreceptor activation device from a delivery device to allow it to expand and contact a wall of the internal carotid artery, applying a first amount of force to a region of a wall of the internal carotid artery at spaced-apart locations to stretch a baroreceptor in the wall during a first local blood pressure of a cardiac cycle of the patient, and applying a second amount of force to the region of the wall of the internal carotid artery with the baroreceptor activation device during a second local blood pressure of the cardiac cycle. The first local blood pressure is lower than the second local blood pressure, the first amount of force is less than the second amount of force, and stretching the baroreceptor in the wall of the internal carotid artery reduces blood pressure in the patient.

In some embodiments, the first amount of force is approximately zero. In some embodiments, the first and second local blood pressures are within a lower and an upper quartile, respectively, of local blood pressures occurring within the cardiac cycle. In some embodiments, applying the first and second amounts of force further involves applying longitudinally varied amounts of force along a length of the baroreceptor activation device, where the first and second amounts of force are averages of the longitudinally varied amounts of force. In some embodiments, the baroreceptor activation device applies the first and second amounts of force asymmetrically to the wall of the artery, with a greater amount of force applied to a first circumferential portion of the wall and a lesser amount of force applied to a second circumferential portion of the wall. In some embodiments, the baroreceptor resides in the first circumferential portion. In some embodiments, applying the first and second amounts of asymmetric force comprises expanding the baroreceptor device in an asymmetric cross-sectional shape.

In some embodiments, the region of the artery is a portion of the internal carotid artery at or near a carotid sinus located within approximately 2 centimeters of a bifurcation of common carotid artery into the internal carotid artery and an external carotid artery. In some embodiments, the baroreceptor activation device has a non-circular cross-sectional shape. In some embodiments, the method may involve, before the advancing step, temporarily stimulating the baroreceptor, and measuring blood pressure in the patient to predict whether implantation of the baroreceptor activation device will result in a reduction in blood pressure. For example, in one embodiment, temporarily stimulating may involve non-invasively stimulating the internal carotid artery at the target location.

In some embodiments, the first and second amounts of force each include a longitudinally directed force component, a torsional force component, and/or a circumferential force component. Some embodiments may further involve delivering a substance to the wall of the internal carotid artery via the baroreceptor activation device, where delivering the substance further stimulates the baroreceptor to facilitate reduction of the blood pressure. Some embodiments may further involve delivering energy to the wall of the internal carotid artery via the baroreceptor activation device, wherein delivering the energy further stimulates the baroreceptor to facilitate reduction of the blood pressure.

In another aspect, an implantable medical device for stimulating carotid baroreceptors to treat hypertension may include at least one longitudinal strut and multiple circumferential connectors attached to the strut(s). The circumferential connectors are configured to apply a first amount of force to a region of a wall of an internal carotid artery during a first local blood pressure of a heart cycle and a second amount of force to a region of the wall of the internal carotid artery during a second local blood pressure of the heart cycle. The first amount of force is less than the second amount of force, and the first local blood pressure is lower than the second local blood pressure.

In some embodiments, the longitudinal strut(s) and/or the circumferential connectors may be made of Nitinol. In some embodiments, at least a portion of the medical device comprises a resorbable material coupled with the Nitinol. In some embodiments, at least some of the circumferential connectors have a spring shape that facilitates a transition of the circumferential connectors between a contracted configuration and an expanded configuration. For example, the spring shape may be a zig-zag shape. In some embodiments, an end-on, cross-sectional shape of the device is non-circular, at least in an expanded configuration of the device. In some embodiments, an end-on, cross-sectional shape of the device is asymmetric, at least in an expanded configuration, and the asymmetric shape is configured to apply more force to a side of the internal carotid artery at an area where the baroreceptor is located than to an opposite side of the internal carotid artery.

In another aspect, a method of changing stiffness of a portion of an artery to facilitate activation of a baroreceptor in or adjacent a wall of the artery may involve: advancing a treatment portion of a flexible, elongate treatment delivery device into the artery in the vicinity of the baroreceptor; contacting the wall of the artery with the treatment portion; and delivering a treatment from the treatment portion to target tissue of the wall of the artery to change the stiffness of the target tissue. Strain in a region of the wall of the artery in the vicinity of the target tissue changes from a first amount of strain during a first local blood pressure of a cardiac cycle to a second amount of strain during a second local blood pressure of the cardiac cycle, where the first amount of strain is larger than the second amount of strain, and the first local blood pressure is higher than the second local blood pressure.

In some embodiments, the first and second local blood pressures are within an upper and a lower quartile, respectively, of local blood pressures occurring within the cardiac cycle. In various embodiments, delivering the treatment may involve delivering one or more of the following treatments: radiofrequency energy, microwave energy, ultrasound energy, X-ray energy, cryotherapy, light energy, laser energy, a chemical treatment and/or a mechanical alteration. In some embodiments, the first local blood pressure occurs during a systolic portion of a heart cycle of the patient, and the second local blood pressure occurs during a diastolic portion of the heart cycle. Optionally, the method may also include, before the advancing step, assessing a likelihood of success of the method. For example, assessing the likelihood may involve reversibly altering tissue stiffness of the portion of the artery with the changed tissue pattern and measuring a physiological parameter of the patient to determine whether the increased tissue stiffness has caused a desired effect.

In some embodiments, reversibly altering the tissue stiffness involves cooling a portion of the artery wall. In some embodiments, reversibly altering the tissue stiffness involves temporarily placing a mechanical device in the artery. In some embodiments, reversibly altering the tissue stiffness involves delivering a chemical to the artery to change its stiffness. Optionally, the method may also include protecting a non-treatment structure or non-treatment portion of the artery before and/or during delivering the treatment. In some embodiments, the method may further involve allowing blood to flow through a portion of the treatment device while the method is being performed. In one embodiment, the artery is an internal carotid artery, the baroreceptor is a carotid baroreceptor, and delivering the treatment helps to reduce systemic blood pressure in the patient. In one embodiment, the target tissue is located in a portion of the internal carotid artery within approximately 2 centimeters of a bifurcation of a common carotid artery into the internal carotid artery and an external carotid artery. In one embodiment, the target tissue is located in a carotid sinus.

In some embodiments, the method may also include measuring an amount of treatment delivered to the artery and providing feedback to a user regarding the measured amount of treatment. In some embodiments, delivering the treatment may include delivering the treatment asymmetrically to a circumference of the wall of the artery, such that a first portion of the wall closer to the baroreceptor receives more treatment than a second portion of the wall farther from the baroreceptor. In some embodiments, the treatment portion has a non-circular cross-section when expanded.

In another aspect, a method of changing stiffness of a portion of a wall of a carotid artery to facilitate activation of a carotid baroreceptor in a patient to treat hypertension in the patient may involve: advancing a treatment portion of a flexible, elongate treatment delivery device into the carotid artery at or in the vicinity of a carotid sinus; contacting the wall of the carotid artery with the treatment portion; and delivering a treatment from the treatment portion to target tissue of the wall of the carotid artery to change the stiffness of the target tissue. Strain in a region of the artery in the vicinity of the target tissue changes from a first amount of strain at or near a highest local blood pressure of a cardiac cycle to a second amount of strain at or near a lowest local blood pressure of a cardiac cycle, and the first amount of strain is larger than the second amount of strain.

In another aspect, a device for changing a tissue property of a portion of a wall of an artery to activate a baroreceptor in or adjacent a wall of the artery in a patient may include: a flexible, elongate catheter body having a proximal end and a distal end; an expandable treatment delivery portion at or near the distal end for expanding to contact the wall of the artery; at least one treatment delivery member attached to or integrated into the expandable treatment delivery portion; a handle coupled with the catheter body at or near the proximal end; and at least one actuator for controlling expansion of the treatment delivery portion. The treatment delivery member may be configured to deliver a treatment to a portion of the artery such that, after the treatment delivery, strain in a region of the wall of the artery in the vicinity of the treated portion of the artery changes from a first amount of strain during a first local blood pressure of a cardiac cycle to a second amount of strain during a second local blood pressure of a cardiac cycle. The first amount of strain is larger than the second amount of strain, and the first local blood pressure is higher than the second local blood pressure.

In some embodiments, the tissue property includes tissue stiffness, and delivering the treatment causes the tissue stiffness to increase along the treated portion of the artery. In some embodiments, the device may also include a cooling member coupled with the treatment delivery portion for cooling a portion of the artery wall. In some embodiments, the device may also include a tissue protection member coupled with the treatment delivery member for protecting a non-treatment structure or a non-treatment portion of the artery during delivery of the treatment. Optionally, the device may also include an aperture in the expandable treatment delivery portion configured to allow blood to flow through a portion of the treatment device during delivery of a treatment. In some embodiments, the device is configured for advancement into, and treatment of, an internal carotid artery, the baroreceptor is a carotid baroreceptor, and the device is configured to treat the internal carotid artery to reduce blood pressure in the patient.

Some embodiments include a sensor on or near the treatment delivery portion for measuring a parameter related to the treatment delivered to the artery and an alert member for providing feedback to a user regarding the measured parameter. In some embodiments, the treatment delivery member is asymmetrically disposed around a circumference of the treatment delivery portion to deliver the treatment asymmetrically to a circumference of the wall of the artery, such that a first portion of the wall closer to the baroreceptor receives more treatment than a second portion of the wall farther from the baroreceptor. In some embodiments, the treatment delivery portion has a non-circular cross-section when expanded.

In another aspect, a method of changing stiffness of a portion of a wall of an artery to facilitate activation of a baroreceptor in or adjacent a wall of the artery may involve: advancing a treatment portion of a flexible, elongate treatment delivery device to a target location in the artery in the vicinity of a baroreceptor; expanding the treatment portion to contact the wall of the artery with the treatment portion; and delivering a treatment from the treatment portion to the wall of the artery in a geometric arrangement to change stiffness of a portion of the artery defined by the geometric arrangement.

In some embodiments, the geometric arrangement includes a path that extends more than ninety degrees circumferentially around the artery. For example, the path may be a closed circumferential path. Alternatively, the path may be a helical path. In some embodiments, the geometric arrangement includes a path that that extends more than one centimeter longitudinally along the artery. In some embodiments, the geometric arrangement includes at least two separate tissue alterations, where each alteration is less than 2 centimeters long in the longest dimension. In some embodiments, the treatment portion includes at least two electrodes for the delivery of radiofrequency energy. In some embodiments, delivering the treatment from the treatment portion to the wall of the artery involves heating target tissue of the wall of the artery. Optionally, the method may also include cooling non-target tissue. Optionally, delivering a treatment from the treatment portion to the wall of the artery may involve cooling target tissue of the wall of the artery. The method may also involve heating non-target tissue. In some embodiments, the method may involve, before the treatment delivery step, assessing a likelihood of success of the method. For example, assessing may involve temporarily stimulating a region of the wall of the artery and monitoring the physiologic response of the patient to the stimulation.

In another aspect, a method of stimulating a baroreceptor in an internal carotid artery of a patient may involve delivering a treatment to increase strain in a region of a wall of the internal carotid artery in a vicinity of the baroreceptor, where delivering the treatment increases strain more in a first 180-degree circumferential portion of the wall of the artery that is closer to an external carotid artery than in a second 180-degree circumferential portion of the wall of the artery that is farther from the external carotid artery.

In some embodiments, the strain is a peak strain measured at a location along a longitudinal axis of the artery. In other embodiments, the strain is a mean strain measured at a location along the longitudinal axis of the artery. In some embodiments, delivering the treatment comprises changing a tissue property of a portion of the wall of the internal carotid artery to activate a baroreceptor in or adjacent a wall of the artery. In some embodiments, delivering the treatment may involve delivering an implant for mechanical activation of a baroreceptor.

In another aspect, a method of stimulating a baroreceptor in an internal carotid artery of a patient may involve advancing a treatment device into the artery, rotating the treatment device to position a portion of the device to face the external carotid artery, and delivering a treatment to increase strain in a region of a wall of the internal carotid artery in a vicinity of the baroreceptor.

In another aspect, an implantable medical device for stimulating baroreceptors in an artery may involve at least two longitudinal struts, where each of the struts has an outward facing surface and an inward facing surface, and where at least some of the longitudinal struts include at least one of a recess on the outward facing surface or an aperture extending from the outward facing surface to the inward facing surface. The device also includes at least two circumferential connectors attached to the longitudinal struts. In one embodiment, at any location along a central longitudinal axis of the implantable medical device, a plane normal to the central longitudinal axis of the device intersects the aperture, the recess, or a pair of struts that subtend an angle in the plane, originating at the central longitudinal axis, of less than thirty degrees.

In another aspect, a method of stimulating a baroreceptor in an artery of a patient may involve: advancing a baroreceptor activation device into the artery through one or more blood vessels of the patient, using a delivery catheter; and releasing the baroreceptor activation device from constraint within the delivery catheter to allow it to expand to contact the wall of the artery. The baroreceptor activation device includes: at least two longitudinal struts, where each of the struts has an outward facing surface and an inward facing surface, and wherein at least some of the longitudinal struts include at least one of a recess on the outward facing surface or an aperture extending from the outward facing surface to the inward facing surface; and at least two circumferential connectors attached to the longitudinal struts. In some embodiments, contacting the wall of the artery with the baroreceptor activation device induces tissue ingrowth into at least one recess or aperture.

In another aspect, a method of stimulating a baroreceptor in an internal carotid artery of a patient to reduce blood pressure in the patient may involve advancing an expandable baroreceptor activation device through a common carotid artery into the internal carotid artery, where the baroreceptor activation device includes two circumferential loops joined by a longitudinal connecting member, and releasing the baroreceptor activation device from a delivery device to allow it to expand and contact a wall of the internal carotid artery. Radial expansion of the baroreceptor activation device during a pulse cycle induces torsion in the device.

In another aspect, a method of stimulating a baroreceptor in an internal carotid artery of a patient to reduce blood pressure in the patient may involve: advancing an expandable baroreceptor activation device through a common carotid artery to a target location in the internal carotid artery, where the baroreceptor activation device comprises at least one longitudinal strut attached to multiple circumferential connectors, and releasing the baroreceptor activation device from a delivery device to allow it to expand and contact a wall of the internal carotid artery. Radial expansion of the baroreceptor activation device during a pulse cycle induces longitudinal strain in a region of the wall of the artery.

BRIEF DESCRIPTION OF THE DRAWINGS

A number of devices and methods claimed, including some described previously, are illustrated by the following figures.

FIGS. 53, 54, 55, 56, 57, 58, 59, 60, and 61 illustrate flattened views of blood vessel wall segments, onto which example geometric arrangements of alterations are projected.

DETAILED DESCRIPTION

Figure 1:
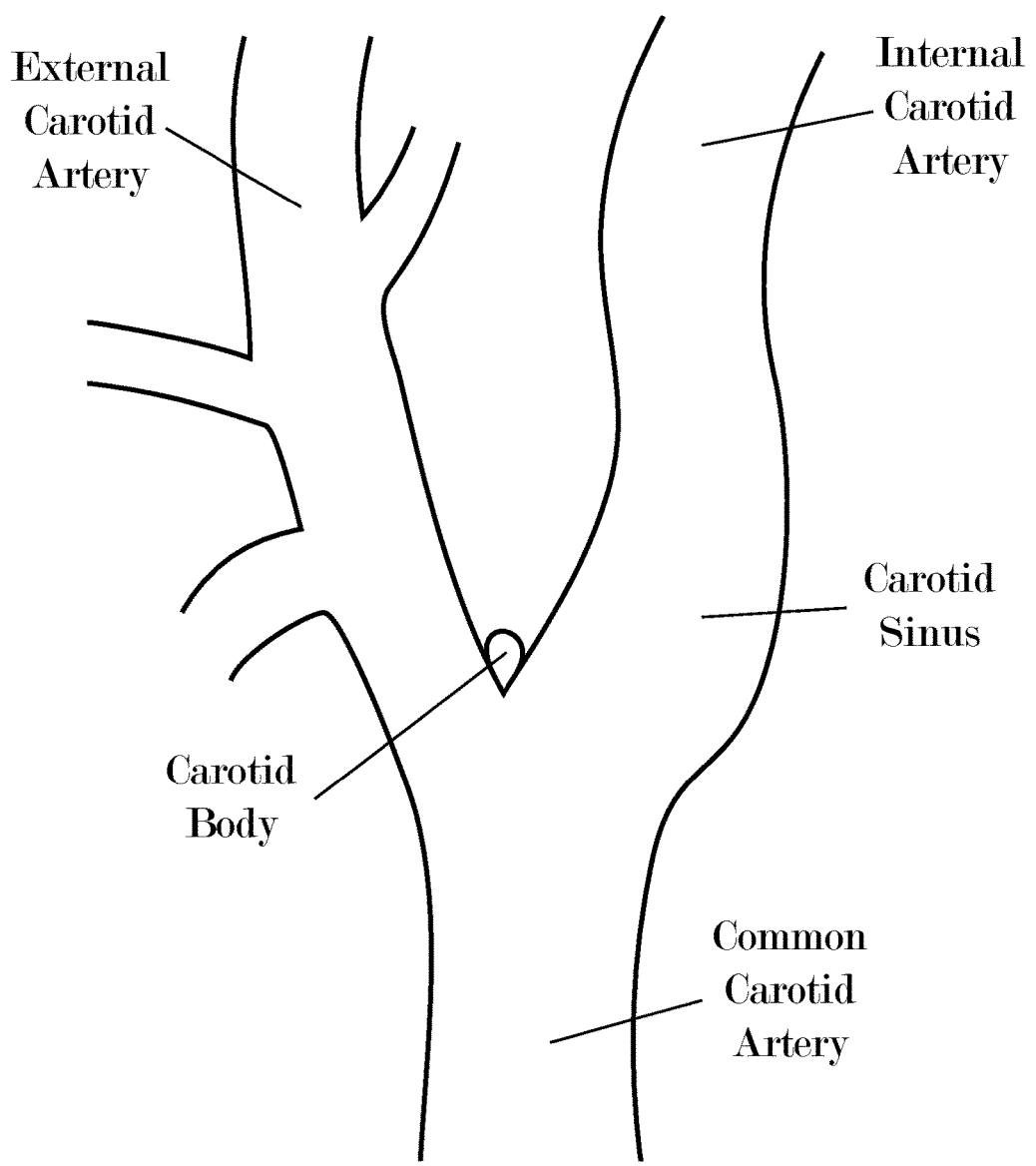
FIG. 1 illustrates the anatomy of the blood vessels near the bifurcation of the common carotid artery, including the external carotid artery, the internal carotid artery, the carotid sinus, and the carotid body.

FIG. 1 shows the anatomy of the blood vessels near the bifurcation of the common carotid artery, including the external carotid artery, the internal carotid artery, and the carotid sinus, and the carotid body.

Figure 2:
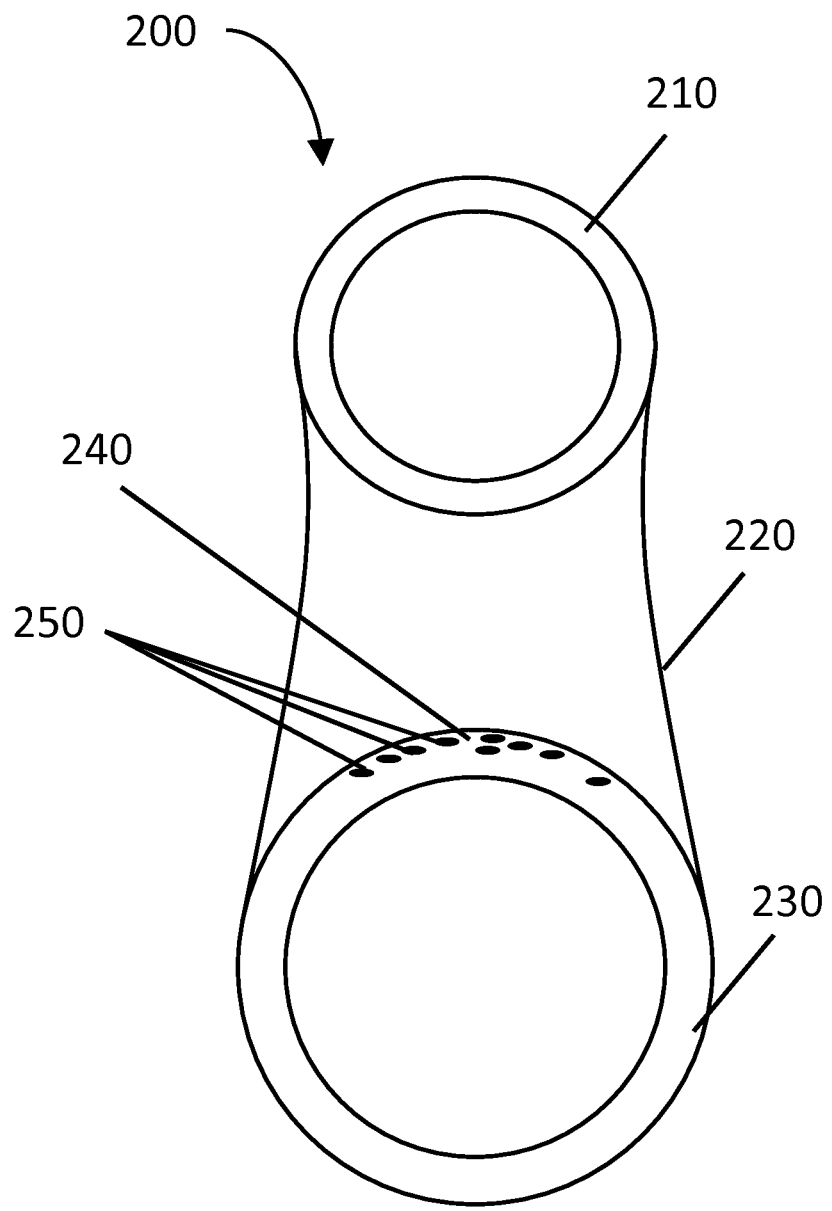
FIG. 2 illustrates a region of the carotid vasculature, in cross section distal to the carotid bifurcation.

FIG. 2 shows a region of the carotid vasculature 200, in cross section distal to the carotid bifurcation. The external carotid artery 210 is shown in cross section. The carotid bifurcation 220 is also shown. The internal carotid artery 230 is shown in cross section. A region of the internal carotid artery 240 is shown in cross section, opposite the external carotid artery, in which baroreceptors 250 are concentrated. In some cases, the embodiments described herein enable a mechanism of action to be focused in a region of baroreceptor concentration, understood here to be a particular vessel known, thought, or tested to contain baroreceptors, or a specific region or location within the vessel in which baroreceptors are known, thought, or tested to be concentrated, including, but not limited to, locations within the carotid vasculature, aortic arch, heart, subclavian arteries, pulmonary arteries, and/or brachiocephalic artery. In some embodiments, the devices described herein may be applied to modulate the signaling of one or more peripheral chemoreceptor, such as a carotid body. The embodiments described herein may be used to treat or prevent a variety of conditions, including but not limited to one more of the following: baroreflex-regulated conditions, hypertension, hypotension, nervous system disorders, metabolic disorders, cardiovascular disease, heart failure, cardiac arrhythmia, renal disease, respiratory disease, diabetes, and insulin resistance. The embodiments described herein may be used to modulate heart rate, blood pressure, and nervous system activity.

Figure 3:
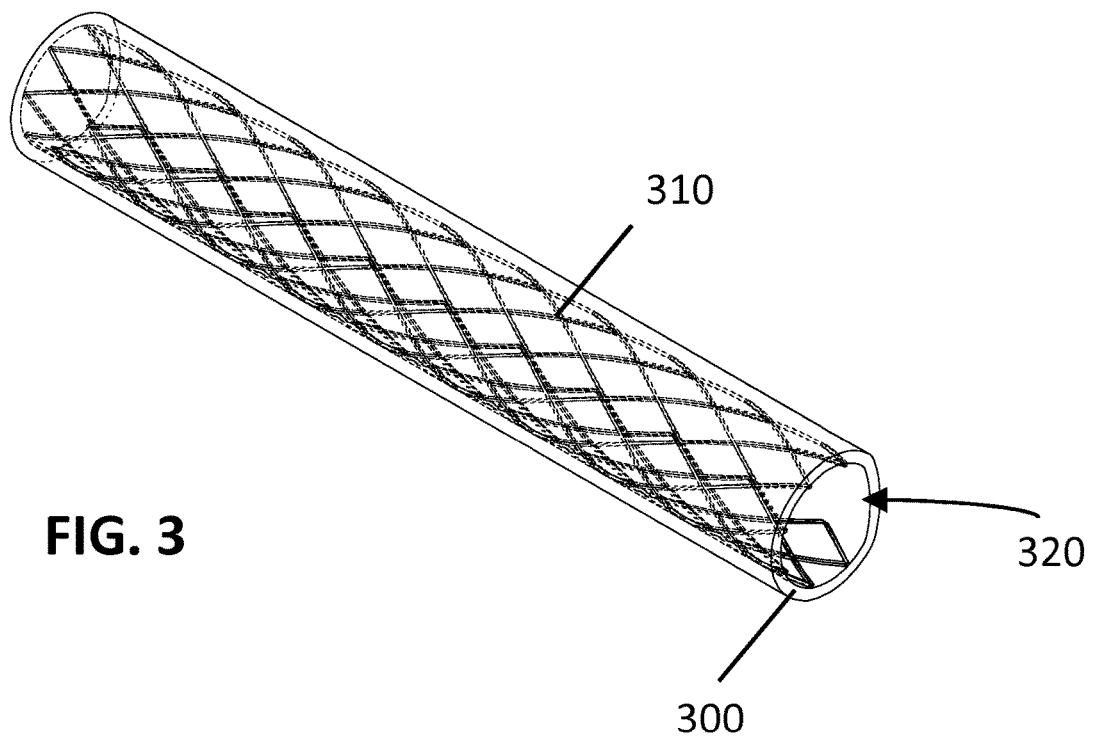
FIG. 3 illustrates an example of an intravascular device positioned within a region of the carotid sinus, which provides a concentrated stretch in a vessel at a site of known or suspected concentration of baroreceptors.

FIG. 3 shows an example of an intravascular device 310 positioned within a region of the carotid sinus 300, which provides a concentrated stretch in a vessel at a site of known or suspected concentration of baroreceptors. In one embodiment, the device 310 is made by laser-cutting a Nitinol tube, and then heat-treating the resulting structure, to create a structure that, in a free and unloaded state, would generally assume a radius of curvature greater than the internal radius of curvature of the target vessel. The radius of curvature generally assumed in the free and unloaded state varies in order to focus the circumferential stretch created by the device 310 on a region of the vessel where receptors are concentrated. In the embodiment, a discontinuity 320 runs in the longitudinal direction, and a circumferential gap preferentially exists at or near the site of a desired concentration in circumferential stretch. In the embodiment, the device 310 may be delivered to the target site using an intravascular catheter, introduced using a traditional transfemoral approach, which allows an operator to unsheath the properly positioned device within the desired vessel, causing the device to self-expand at the desired location.

More generally, in a variety of embodiments, the device 310 and method embodied in FIG. 3 may: use one or more of a variety of biocompatible metals or polymers known to be used in intravascular stents; feature a strut pattern that achieves desired flexibility and radial force during delivery and upon implantation; include resorbable, degradable, dissolvable, and/or absorbable components that, upon resorbing, degrading, dissolving, and/or absorbing, allow a change in the forces imparted by the remaining device structure on the vessel; be placed endovascularly via catheter, or extravascularly through surgery; target the proximal-most 1 cm of the internal carotid artery, and/or a region believed, known, or confirmed to contain a concentration of baroreceptors; target the medial wall of the internal carotid artery, and/or a region believed, known, or confirmed to contain a concentration of baroreceptors; target the side of the internal carotid artery originating in the crotch of the common carotid artery bifurcation and/or facing the external carotid artery, and/or a region believed, known, or confirmed to contain a concentration of baroreceptors; feature a discontinuity 320 in the generally longitudinal direction (relative to the axis of the vessel) along part, all, or none of the device 310 length; feature, in a free and unloaded state, a radius of curvature (in the radial direction) that is larger or exceptionally larger (e.g. more unfurled, along part or all of the longitudinal discontinuity) which acts to focus the circumferential stretch imparted on the vessel wall, by the device 310 and/or blood pressure, on a desired region; feature, in a free and unloaded state, a range of radii of curvature (in the radial direction) that causes force to be imparted on the vessel wall in a manner that favorably focuses the circumferential stretch imparted on the vessel wall, by the device 310 and/or blood pressure, on a desired region; feature a radial stiffness that varies, around the circumference and/or along the length, in a manner that favorably focuses the circumferential stretch imparted on the vessel wall, by the device 310 and/or blood pressure, on a desired region; conform to the shape of the carotid sinus, including (but not limited to) a region that is substantially non-circular and/or non-cylindrical; enable an operator to peri-operatively adjust the radial and/or longitudinal force imparted by the device 310 on the vessel.

The device 310 may also feature augmentations or recesses that create localized stress concentrations in the vessel wall, or act to reconfigure the cross section of the vessel wall in a manner that changes the stress in the vessel wall that arises from blood pressure. The augmentations or recesses may be exposed continuously to the vessel wall, exposed to the vessel wall when blood pressure falls above or below a given threshold, or exposed to the vessel when overlapping regions of a device 310 are moved into a non-overlapping configuration.

Figure 4:
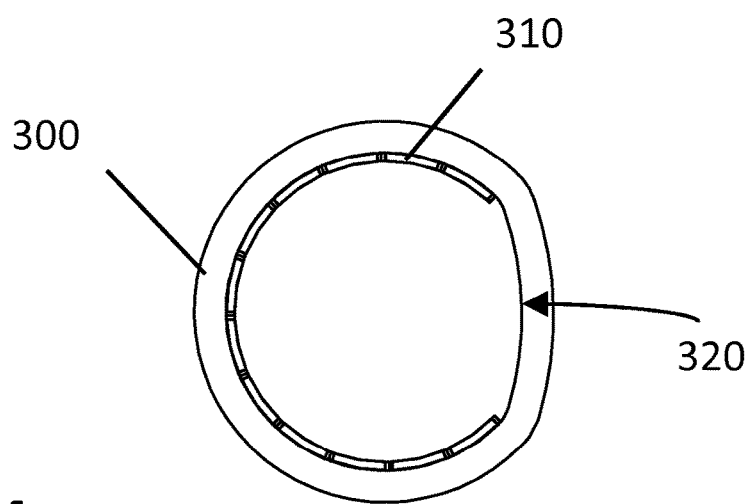
FIG. 4 illustrates an end view of an embodiment shown in FIG. 3.

FIG. 4 shows an end view of the embodiment shown in FIG. 3. In the embodiment shown, the circumferential discontinuity 320 runs the length of the device 310, and the device 310 has a circumferential region in which the discontinuity 320 is preserved. It shall be understood that, though, that in some embodiments, the circumferential discontinuity 320 may run only part of the length of the device 310, and that the circumferential discontinuity 320 may occupy varying circumferential locations, including some in which the circumferential region is not visibly preserved from an end view.

Figure 5:
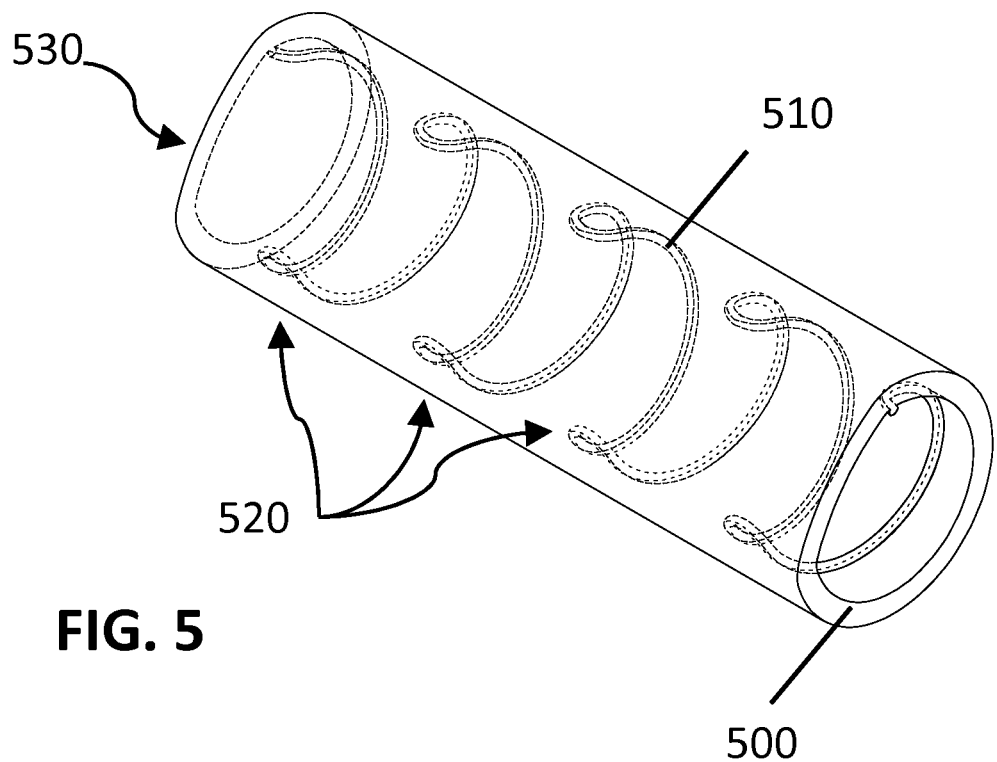
FIG. 5 illustrates an example of an intravascular device comprised of substantially one continuous member that assumes a curved configuration upon delivery via catheter into a blood vessel.

FIG. 5 shows an example of an intravascular device 510 positioned within a blood vessel 500 and comprised of substantially one continuous member that assumes a curved configuration upon delivery via catheter into a blood vessel. In one embodiment, the device 510 is made of biocompatible metal (including at least some portion comprised of Nitinol), assumes a substantially straightened configuration while within a delivery catheter, and assumes a curved configuration upon exiting a delivery catheter that causes strain to be focused on a particular region of the vessel wall that has a high concentration of stretch receptors.

In the embodiment shown, a circumferential discontinuity 530 can be seen that runs the length of the device 510, and an end view of the device 510 reveals a circumferential region in which the discontinuity is preserved. It shall be understood, though, that in some embodiments, the circumferential discontinuity 530 may run only part of the length of the device 510, and that the circumferential discontinuity 530 may occupy varying circumferential locations, including some in which the circumferential region is not visibly preserved from an end view.

In one embodiment, the device 510 may feature a radius of curvature, relative to its gross longitudinal axis (i.e., when viewed from one end), that is larger where nearer to the reversal 520 where the primary wire reverses circumferential direction, thus creating higher strain in the vessel wall where it spans reversing regions of the primary wire. The reversal of circumferential direction may take the form of various shapes or structures. For example, the reversal 520 may be take the form of one or more of: a sharp change in direction, a gradual change in direction; a change in direction in two dimensions; a change in direction in three-dimensions; a complete change of direction; a partial change of direction; other changes; or a combination thereof.

More generally, in a variety of embodiments, the device 510 and method of FIG. 5 may: feature a radio-opaque coil wound around a Nitinol core wire, with the two attached to one another at least at the distal end; be placed endovascularly via catheter, or extravascularly through surgery; be wrapped around the exterior of a blood vessel; and have resorbable, degradable, dissolvable, and/or absorbable members which, upon resorbing, degrading, dissolving, or absorbing, transfer residual force in the device 510 and/or vessel in a favorable manner, such as to locate strains to favorably activate stretch receptors in the vessel wall.

Figure 6:
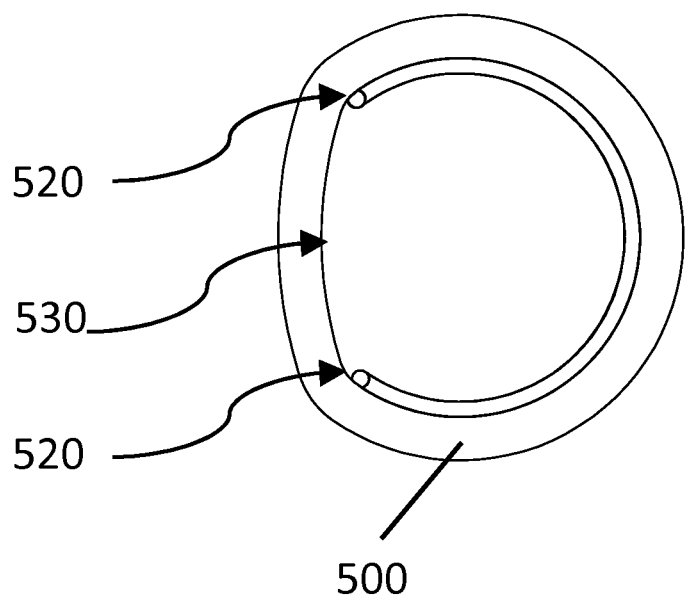
FIG. 6 illustrates an end view of an embodiment shown in FIG. 5.

FIG. 6 shows an end view of the embodiment illustrated in FIG. 5, including discontinuity 530. At some longitudinal locations, discontinuity 530 is bounded circumferentially at the location 520 where the primary wire reverses circumferential direction.

Figure 7:
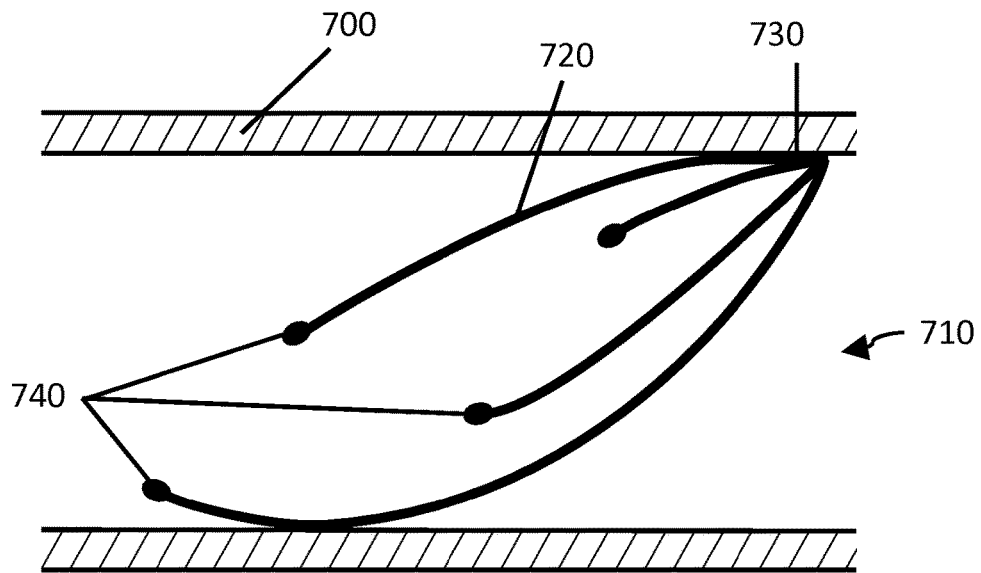
FIG. 7 illustrates an example of an intravascular device that features one or more members that apply radial force on a vessel wall.

FIG. 7 shows an example of an intravascular device 710 that features one or more members 720 that apply radial force on a vessel wall 700. In the embodiment shown, the members 720 concentrate outward radial force on multiple distinct longitudinal locations in order to alter or deform the vessel wall 700. The outward radial force may also help the implant maintain a desired position within the vessel. The ends 740 of the members 720 may be bluntly shaped to avoid unwanted trauma to the vessel wall. The embodiment may be laser-cut from a biocompatible stainless steel tube, and delivered via endovascular catheter.

One embodiment of intravascular device 710 may comprise a series of elongate members 720 extending from a hub 730. Elongate members 720 may be of the same size, may be of different sizes, or a combination thereof. Elongate members 720 may have a gentle curve, sharp curve, be straight, take other forms described herein, or combinations thereof. Although the ends 740 may be bluntly shaped to avoid trauma, they need not (or need not alone) exert outward radial pressure on the vessel wall 700. Portions along the elongate members 720, the hub 730, or combinations thereof may also exert forces.

More generally, in a variety of embodiments, the device 710 and method of FIG. 7 may: be made of biocompatible metals or polymers; be placed endovascularly via catheter, or extravascularly through surgery; include members specifically purposed to hold the implant in a desired position, as well as other members specifically purposed to impart a desired force on the vessel wall; include members that extend different longitudinal and/or circumferential lengths, and/or impart force at distinct longitudinal and/or circumferential locations; or include combinations of these features.

Figure 8:
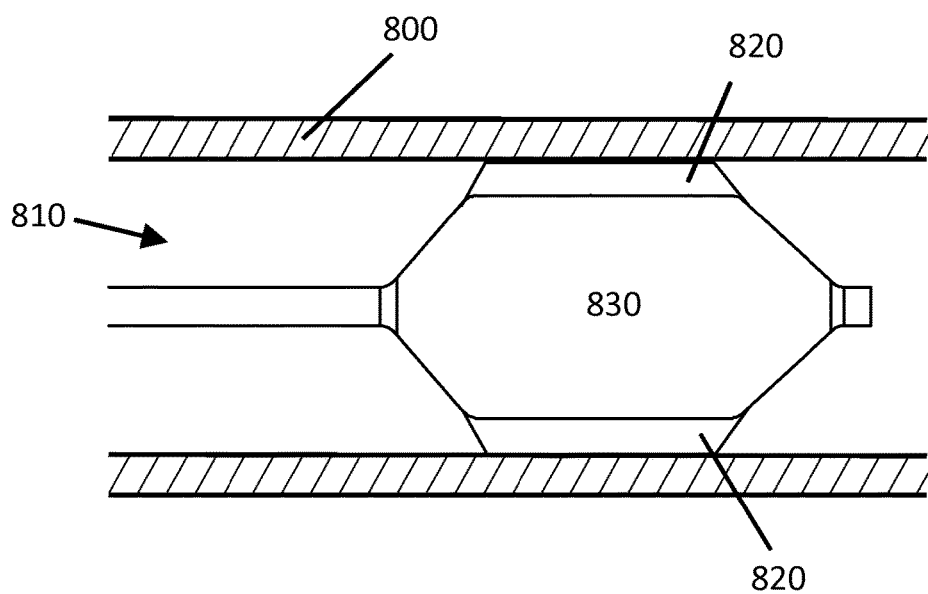
FIG. 8 illustrates an example of an intravascular device that features one or more cutting members, which cut the internal wall of the target vessel in order to increase the amount of strain in the vessel wall caused by a range of blood pressures.

FIG. 8 shows an example of an intravascular device 810 that features one or more cutting members 820, which cut the internal wall of the target vessel in order to increase the amount of strain in the vessel wall 800 caused by a range of blood pressures. The cuts may be made such that when the tissue heals, scar tissue is formed that alters the mechanical properties of the treated tissue. In one embodiment, one or more cutting members 820 are mounted onto an inflatable balloon 830 on a balloon catheter. The balloon catheter is positioned within the carotid sinus, and the balloon 830 is inflated, causing the cutting member 820 to engage with the vessel wall 800. The balloon 830 is then deflated, and the balloon catheter is removed.

More generally, in a variety of embodiments, the device 810 and method of FIG. 8 may: feature one or more cutting members 820; feature one or more cutting members that extend part or substantially all of the length of the balloon, or a combination thereof; feature cutting members 820 that alter the effective strain resistance—in the circumferential direction, longitudinal direction, or both—of the blood vessel in which the balloon is inflated; utilize no balloon at all, but instead feature a cutting member incorporated into a catheter; or may include combinations of these features or characteristics. The cutting member 820 may take the form of various shapes or configurations. For example, the cutting member 820 may be: jagged, toothed, even, uneven, straight, curved, serrated, granton edged, scalloped, wavy, take other forms, or combinations thereof.

Figure 9:
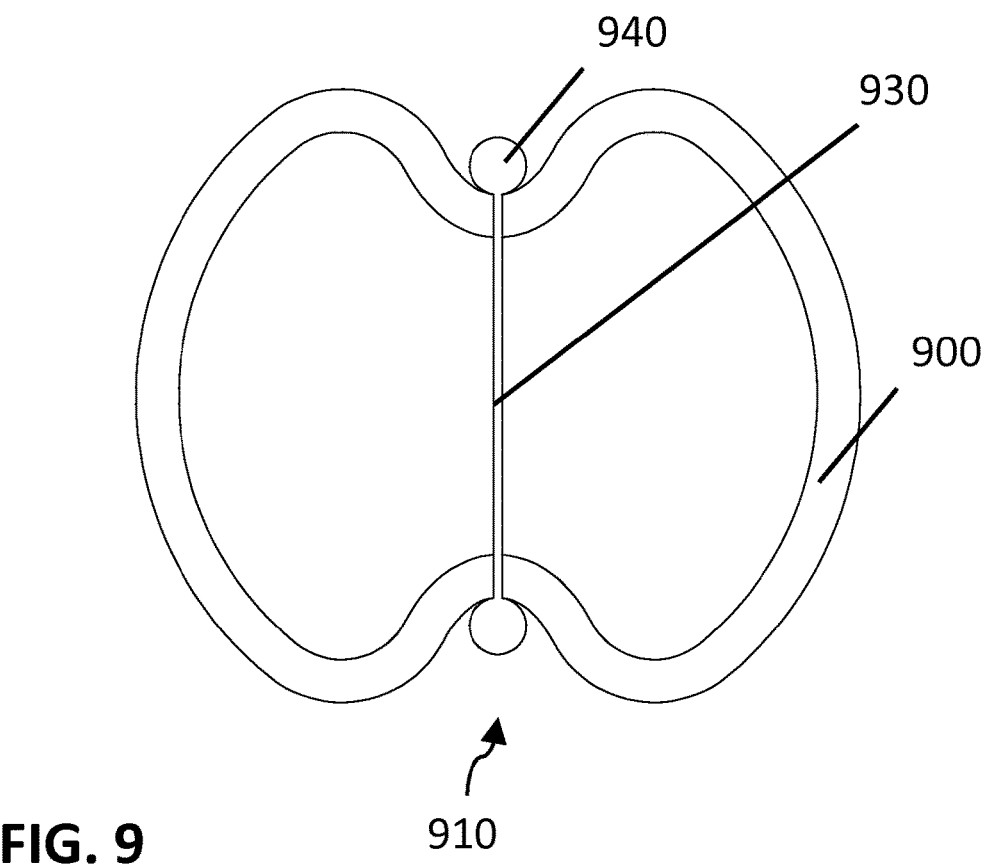
FIG. 9 illustrates a cross-sectional view of an example of a method and device that repositions one or more sites along the circumference or length of a vascular region, for the purposes of adjusting the strain occurring at one or more sites.

FIG. 9 is a cross-sectional illustration showing an example of a method and device 910 that repositions one or more sites along the circumference or length of a vascular region, for the purposes of adjusting the strain occurring at one or more sites (though not necessarily at the same one or more sites repositioned). In one embodiment, shown in FIG. 9, a metallic member 930 is anchored to two sites in a wall of blood vessel 900 and spans part of the lumen of the vessel, pulling the two sites toward the radial center of the blood vessel 900. The resulting vessel configuration increases strain at receptor sites in the vessel wall within the range of blood pressures encountered, causing general systemic blood pressure to be reduced at physiologically-encountered blood pressures.

More generally, in a variety of embodiments, the device 910 and method of FIG. 9 may: feature one or more members 930 that span at least part of the blood vessel lumen, or which reside substantially against the interior of the blood vessel, or which reside against the outside the blood vessel; feature one or more anchors 940 which mechanically secure to the vessel wall or its surrounding tissues, or become embedded into the wall or surrounding tissues due to a biological tissue response, or adhesively engage the vessel wall; be comprised of biocompatible metal or polymers; be delivered via intravascular catheter and/or a surgical procedure and/or minimally invasive surgical tools; be placed endovascularly via catheter, or extravascularly through surgery; or may include combinations of these features or characteristics.

In an embodiment, member 930 (with anchors 940 at one or more ends) may travel from a first location inside the blood vessel, through the blood vessel wall to a location within or outside of the blood vessel wall, and back to a second location inside the blood vessel; member 930 may be tensioned to cause a deformation of the blood vessel. A delivery system for said device may enable invagination of a portion of the blood vessel wall (for example, using vacuum) to aid in proper placement of the device. A ratcheting mechanism may enable member 930 to be secured in one or more anchor 940 at a desired location, with excess length, and a severing or release mechanism may allow removal of excess length of member 930.

In an embodiment, member 930 (with anchors 940 at one or more ends) may travel from a first location outside the blood vessel wall, through the blood vessel wall to a location within or inside of the blood vessel wall, and back to a second location outside of the blood vessel wall; member 930 may be tensioned to cause a deformation of the blood vessel. A delivery system for said device may enable invagination of a portion of the blood vessel wall (for example, using vacuum) to aid in proper placement of the device. A ratcheting mechanism may enable member 930 to be secured in one or more anchor 940 at a desired location, with excess length, and a severing or release mechanism may allow removal of excess length of member 930.

Figure 10:
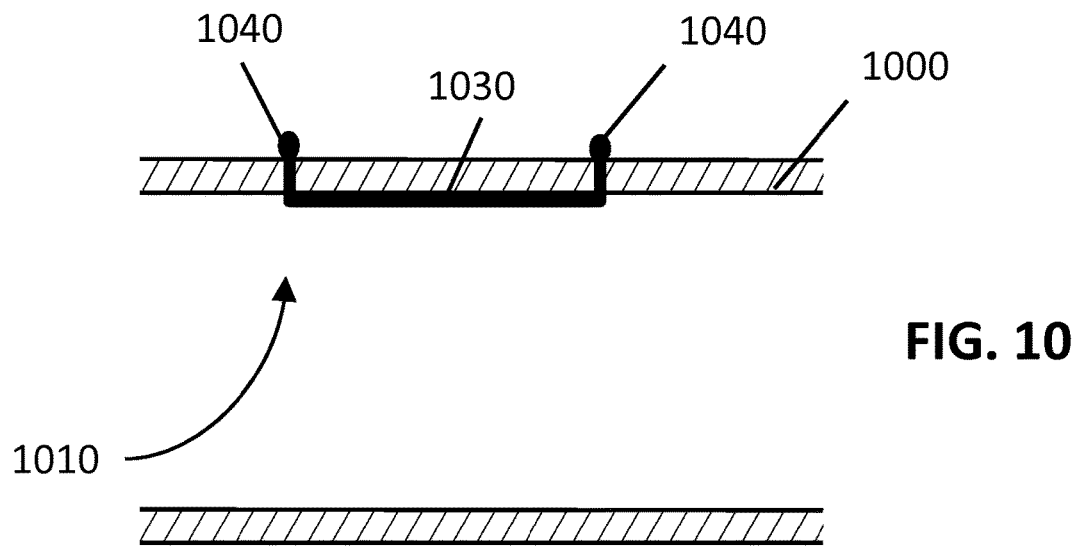
FIG. 10 illustrates a cross-sectional view of an example of a method and device that repositions one or more sites along the circumference or length of a vascular region, for the purposes of adjusting the strain occurring at one or more sites, in which a member is anchored at two sites that vary in longitudinal location along a vessel wall, and in which the member travels generally along the inside wall of the vessel.

FIG. 10 illustrates an embodiment of a device 1010 with similar characteristics to those illustrated in FIG. 9, in which a member 1030 is anchored by anchors 1040 at two sites that vary in longitudinal location along the outside of vessel wall 1000, and in which the member 1030 travels generally along the inside wall of the vessel.

Figure 11:
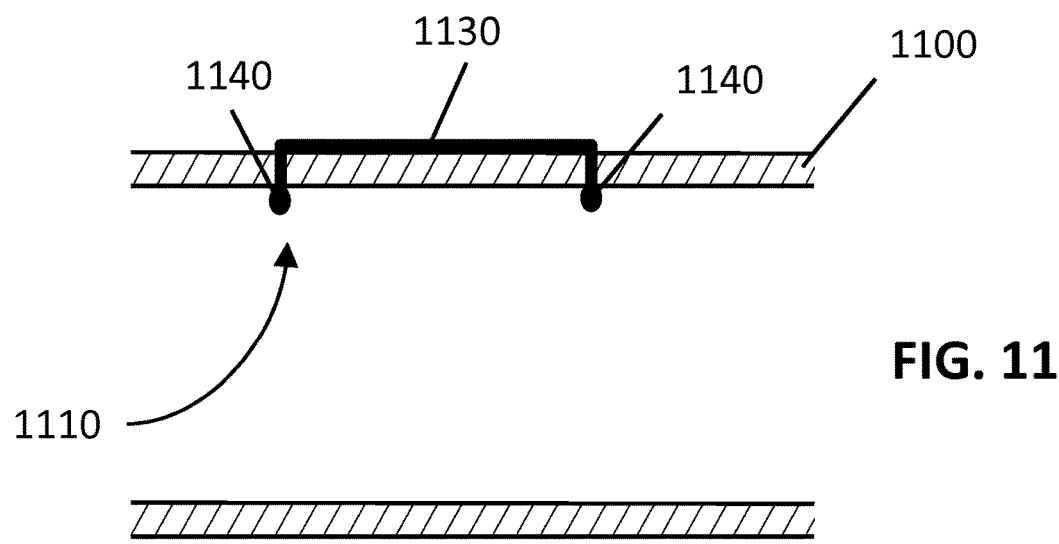
FIG. 11 is a cross-sectional illustration showing an example of a method and device that repositions one or more sites along the circumference or length of a vascular region, for the purposes of adjusting the strain occurring at one or more sites, in which a member is anchored at two sites that vary in longitudinal location along a vessel wall, and in which the member travels generally along the outside wall of the vessel.

FIG. 11 illustrates an embodiment of a device 1110 with similar characteristics to those illustrated in FIG. 9, in which a member 1130 is anchored by anchors 1140 at two sites that vary in longitudinal location along the inside of vessel wall 1100, and in which the member 1130 travels generally along the outside wall of the vessel.

FIGS. 12, 13, 14, and 15 show examples of devices 1210, 1310, 1410, that exhibits strain or deformation in one or more sections of the devices 1210, 1310, 1410 or directions when a strain is created in another one or more sections of the devices 1210, 1310, 1410, or another direction. In some embodiments, the devices 1210, 1310, 1410 are delivered endovascularly and assume a position within a vessel. The geometry of the devices 1210, 1310, 1410 may be such that radial dilation of the devices (as may be caused by an increase in blood pressure during the cardiac cycle) causes longitudinal strain (elongation and/or shortening) of part or all of the implant 1210, 1310, 1410, and/or pushes or pulls part or all of the implant longitudinally, circumferentially, or both, imparting strain on the host vessel. In some cases, incorporation of the implant 1210, 1310, 1410 into surrounding tissues, or incorporation of surrounding tissues into the implant 1210, 1310, 1410, may play a role in pushing or pulling tissues as implant 1210, 1310, 1410 changes shape. These devices 1210, 1310, 1410 may all have similar structures. Generally, they may have connecting members 1220, 1320, 1420, and links 1240, 1340, 1440. In one embodiment, connecting members 1220, 1320, 1420 may take various shapes including zig-zag shaped, triangle wave shaped, saw tooth wave shaped, sinusoidal wave shaped, other repeating patterns, non-repeating patterns, or combinations thereof. Links 1240, 1340, 1440 may be described as members that extend from connecting members 1240, 1340, 1440 and which may link two connecting members (see, e.g., FIGS. 12, 13, and 15), and which also may vary in shape. During radial dilation of the devices, connecting members 1220, 1320, 1420 may move or swing in the general direction marked with small arrows, which may create strain in the vessel wall. In some embodiments, an absence of device material within the connecting members 1220, 1320, 1420 and/or links 1240, 1340, 1440 may promote or enable tissue ingrowth and/or may improve the anchoring of the device in the vessel wall and/or may improve the flexibility of the device and/or reduce undesired levels of a stress concentration. Substantially straight and/or substantially unbending links 1240, 1340, 1440 may act to constrain the distance between sites on connecting members 1220, 1320, 1420, and/or sites along links 1240, 1340, 1440.

Figure 12:
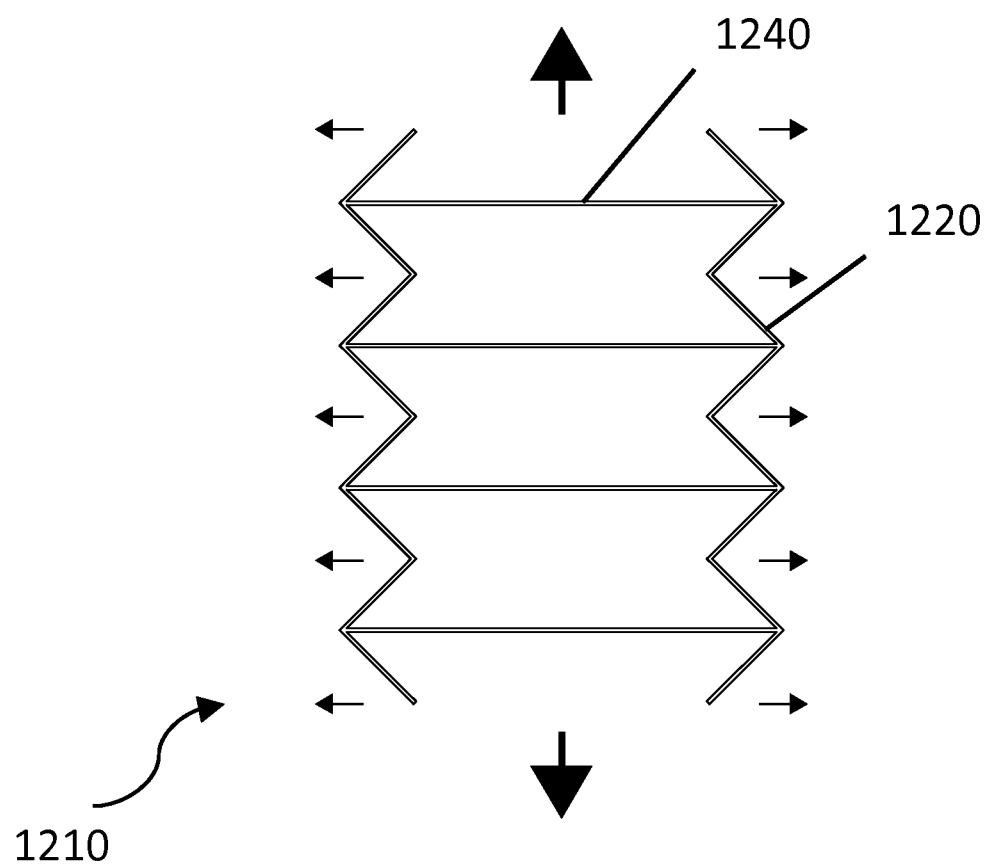
FIGS. 12, 13, and 14 illustrate flattened representations of embodiments of devices.

FIG. 12 illustrates a flattened representation of an embodiment of device 1210 that elongates at the locations marked with small arrows when circumferential strain (associated with radial dilation) marked with large arrows occurs. The resulting longitudinal strain imparted on the host vessel activates stretch receptors in the host vessel. Device 1210 comprises connecting members 1220 and links 1240.

Figure 13:
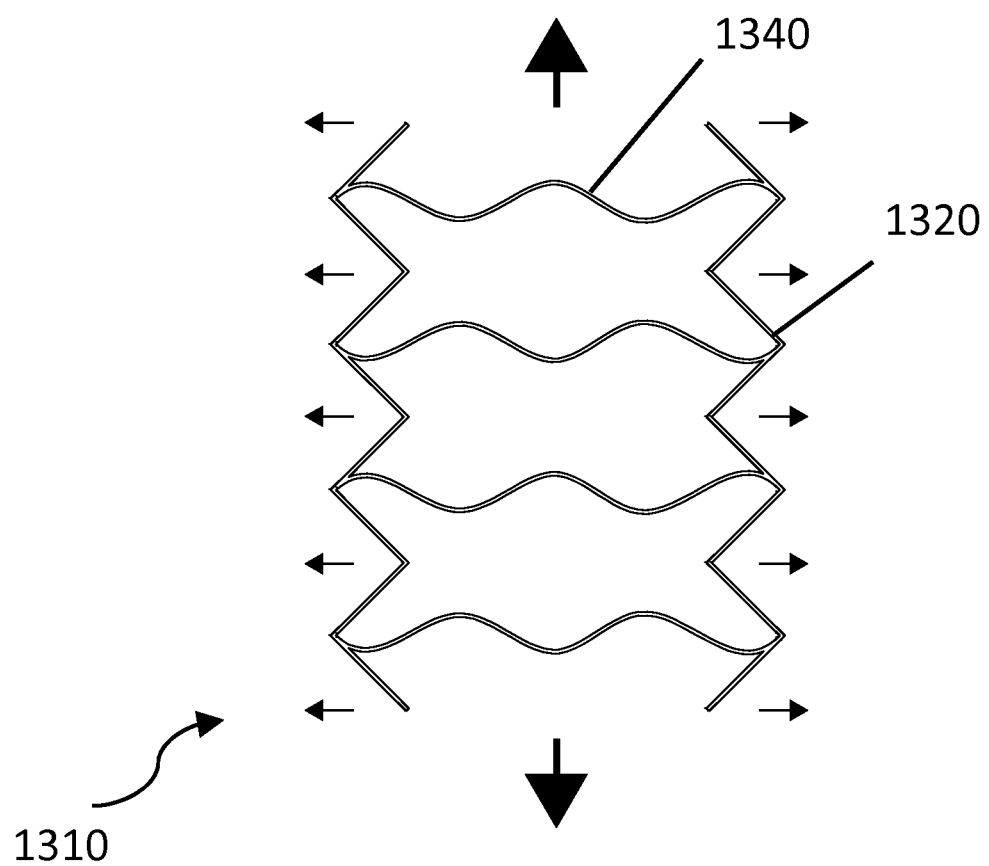

FIG. 13 illustrates a flattened representation of an embodiment of device 1310, which features a number of connecting members 1320 between more distal and more proximal regions of the device 1310, the connecting members 1320 providing and/or promoting a desired spring constant between the locations at which they interface with the more distal and more proximal regions of the device 1310, and/or providing and/or promoting a desired distribution, direction, and/or amount of strain arising in the blood vessel wall as the device 1310 changes shape. The connecting members may be connected by one or more links. In some embodiments, the connecting members 1320 may vary in effective spring constant along their length. In some embodiments, the connecting members 1320 may interface with the more distal and more proximal regions of the device 1310 at circumferentially non-aligned locations. In some embodiments, changes in shape of the device 1310 (for example, changes in the more distal and more proximal regions of the device 1310) arising from vessel dilation during the cardiac cycle cause shape changes in the connecting members 1320 of the device 1310 that advantageously stretch baroreceptors.

Figure 14:
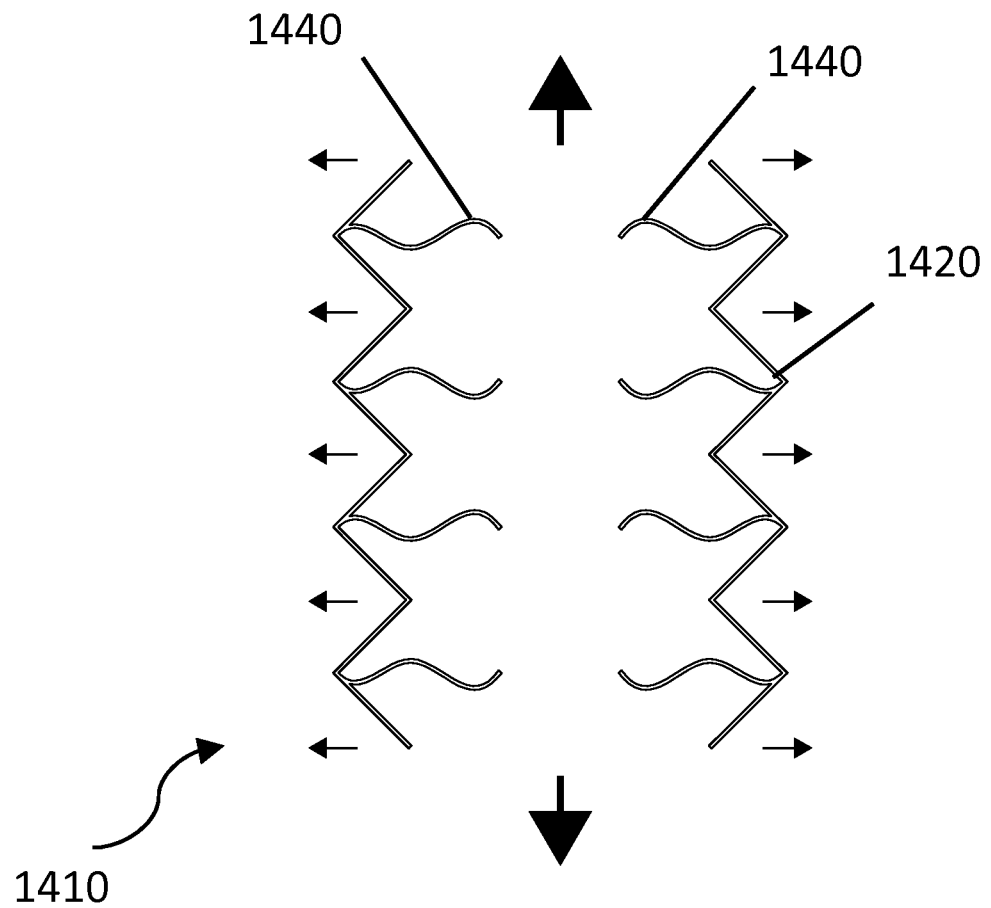

FIG. 14 illustrates an embodiment of device 1410, which has some incomplete or partial links 1440 that do not extend all of the way between or connect with the connecting members 1420 and either more proximal or more distal sections. In some embodiments, there may be a combination of incomplete or partial links 1440 and complete links.

Figure 15:
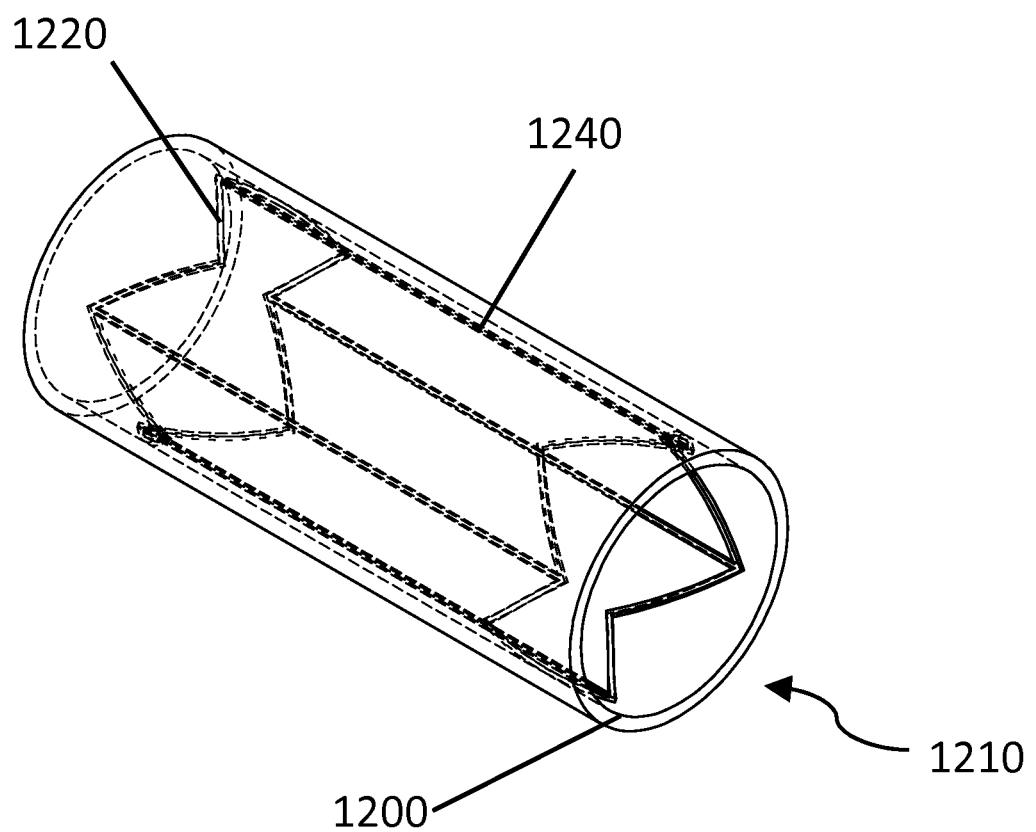
FIG. 15 illustrates an embodiment of a device that exhibits strain or deformation in one or more sections of the device or directions when a strain is created in another one or more sections of the device or another direction.

FIG. 15 illustrates the device 1210 shown in FIG. 12 implanted in a blood vessel 1200. When device 1210 is implanted in a blood vessel 1200, a first end of a connecting member 1220 may connect to a second end of a connecting member 1220 to form a substantially circular or other shape. In an embodiment, the links 1240 may be substantially parallel to the axis of the vessel 1200.

Some embodiments of the aforementioned devices 1210, 1310, 1410 or other devices may include strut angles that cause regions of the device 1210, 1310, 1410, or the full device 1210, 1310, 1410, to lengthen and/or twist when the device 1210, 1310, 1410 is radially expanded; cause or allow different amounts of longitudinal strain at different circumferential locations, and/or at different longitudinal locations, for example due to variations in the geometry or effective spring constant of the longitudinal and/or circumferential sections. An embodiment may lack links 1240, 1340, 1440 between at least some connecting members 1220, 1320, 1420 and either more proximal or more distal sections, such that changes in the shape of the more proximal or more distal section arising from the cardiac cycle impart less constrained movement on at least some connecting members, and thereby advantageously change the strain in the vessel wall.

More generally, in a variety of embodiments, the devices 1210, 1310, 1410 and methods of FIGS. 12, 13, 14, and 15 may: be made of biocompatible metals or polymers; be placed endovascularly via catheter, or extravascularly through surgery; include elements which become anchored within the tissues of the vessel, and other elements which are prone to movement and/or deformation and do not become anchored within the tissues of the vessel (e.g. in order to maintain freedom of motion for the latter elements and/or to avoid unwanted trauma to tissues); be configured to provide desired forces on a region of a vessel after one or more resorbable, degradable, dissolvable, and/or absorbable portions of the structure of the device 1210, 1310, 1410 come to un-constrain permanent portions of the device 1210, 1310, 1410; include combinations of these features.

Figure 16:
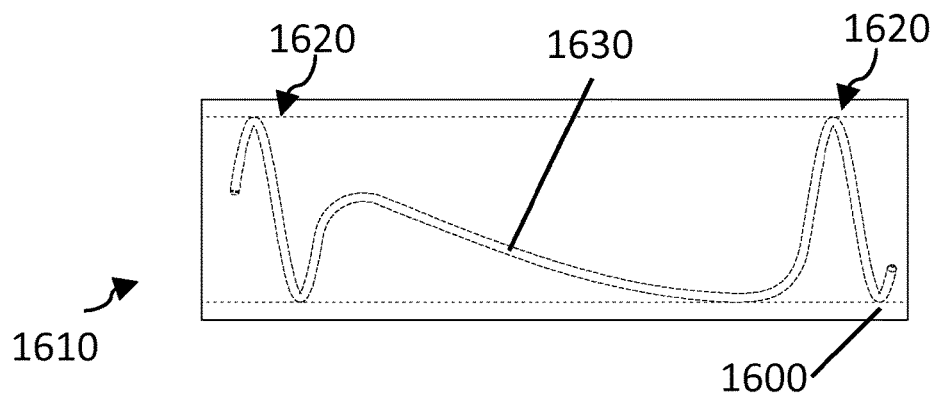
FIG. 16 illustrates a side view of a method or device that creates torsional and longitudinal stress in a blood vessel wall.

FIG. 16 illustrates a side view of an embodiment of a method or device 1610 that creates torsional and longitudinal stress in a blood vessel 1600. In one embodiment, two loops 1620 are positioned in a vessel, each mechanically anchoring to the vessel wall 1600 such that they will not rotate relative to the vessel 1600, and each assuming an approximately circumferential position within the vessel 1600. A member 1630 that is not substantially parallel to the main axis of the blood vessel 1600, which resides substantially within a cylinder that approximates the inner wall of the vessel 1600, connects the two loops 1620, and creates torsional stress in the wall of the blood vessel that varies during the cardiac cycle.

Figure 17:
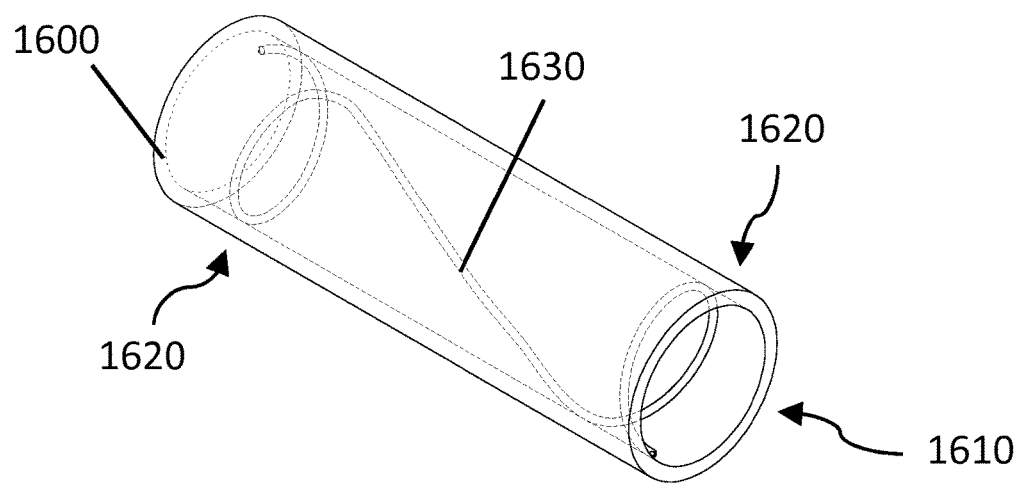
FIG. 17 illustrates a perspective view of a method or device illustrated in FIG. 16.

FIG. 17 illustrates a perspective view of the embodiment illustrated in FIG. 16. More generally, in a variety of embodiments, the device 1610 and method of FIGS. 16 and 17 may: feature loops 1620 that are partial, or substantially complete; feature loops 1620 that are substantially planar, or follow a generally helical and/or spiral pattern; feature loops 1620 with a constant or changing radius of curvature; feature a small number of loops 1620 (e.g. two loops) or a large number of loops 1620 (e.g., sixteen loops); feature loops 1620 that become embedded into the wall of the vessel 1600 after implantation, preventing the loops 1620 from rotating relative to the wall of the vessel 1600; feature a small number of members 1630 between loops 1620 (e.g., two members), up to a large number of members between loops 1620 (e.g., sixteen members); feature members 1630 loaded in tension throughout the cardiac cycle, loaded in compression throughout the cardiac cycle, or loaded in compression or tension at different times during the cardiac cycle; feature one or more members 1630 that are not substantially parallel to the main longitudinal axis of the vessel, and which are concentrated on one or more side of the vessel, in order that longitudinal deformation of the vessel 1600 is asymmetrically prevented by the device 1610, thus causing the curvature of the vessel 1600 to change during the cardiac cycle; feature one or more members 1630 that are substantially parallel to the main longitudinal axis of the vessel 1600, and which are concentrated on one or more side of the vessel 1600, in order that longitudinal deformation of the vessel 1600 is asymmetrically prevented by the device 1610, thus causing the curvature of the vessel 1600 to change during the cardiac cycle; feature members 1630 which travel in alternating directions (clockwise vs. counter-clockwise) between some or all adjacent longitudinal loop-member-loop sections; feature a configuration of loops 1620 and one or more members that promotes any combination of the following stresses: longitudinal stress, torsional stress, and/or circumferential stress; be placed endovascularly via catheter, or extravascularly through surgery; have other features, or combinations of these and/or other features.

FIGS. 18, 19, 20, and 21 illustrate an embodiment of a device 1810 with three or more longitudinal regions, separated from other longitudinal regions at a given longitudinal location (or latitude) by one or both of (a) one or more of a first kind of absence of device 1810 material, where there is no contact between the device 1810 and the vessel wall, and the radius of curvature of the vessel wall is increased, and/or (b) one or more of a second kind of absence of device 1810 material, where there is no contact between the device 1810 and the vessel wall, and the radius of curvature of the vessel wall is not increased.

Figure 18:
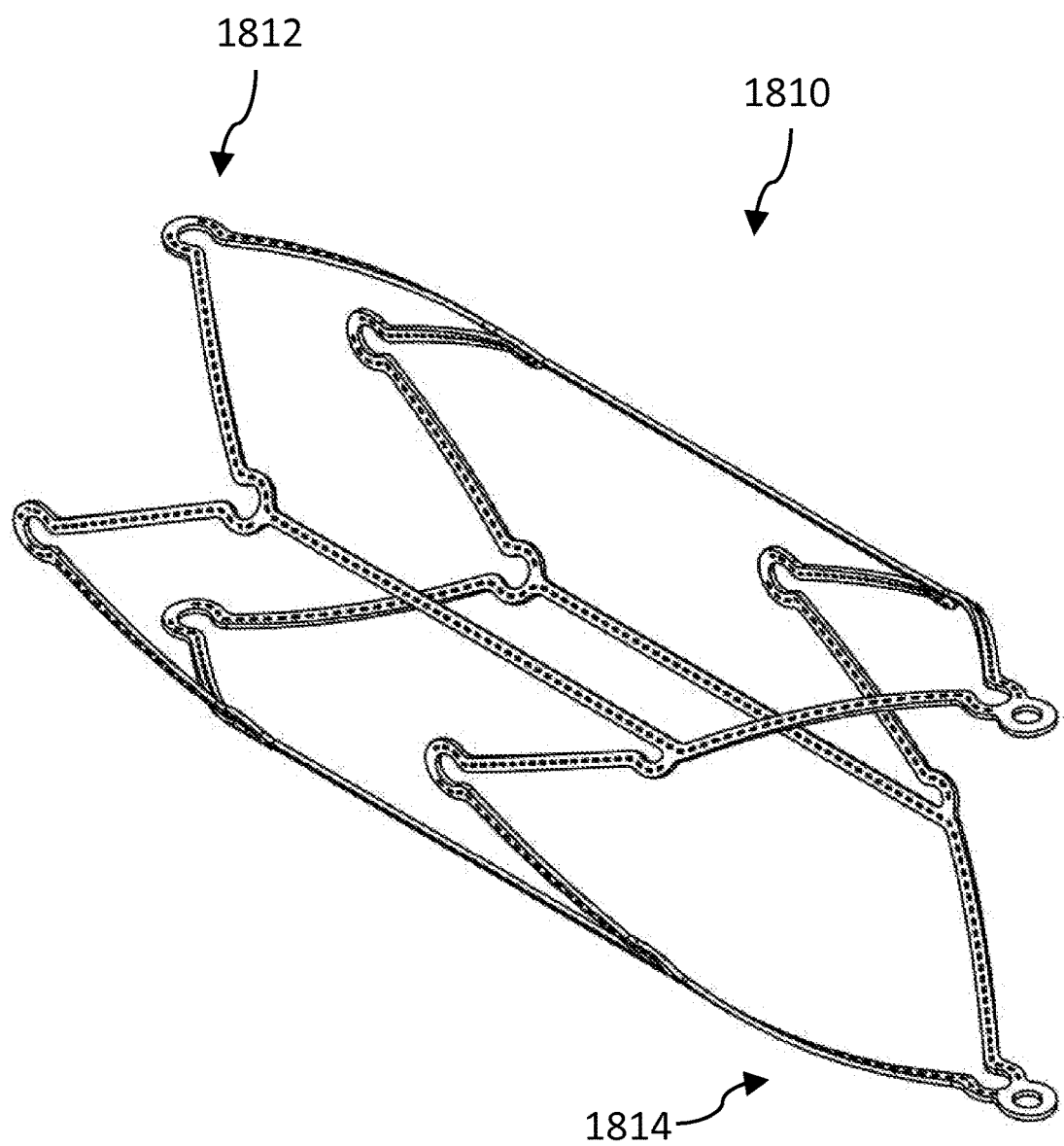
FIGS. 18, 19, 20, and 21 illustrate a projected view, a cut-and-flattened view, a zoomed-in view, and another zoomed-in view, respectively, of an embodiment of a device with three or more longitudinal regions, separated from other longitudinal regions at a given longitudinal location by one or both of (a) one or more of a first kind of absence of device material, where there is no contact between the device and the vessel wall, and the radius of curvature of the vessel wall is increased, and/or (b) one or more of a second kind of absence of device material, where there is no contact between the device and the vessel wall, and the radius of curvature of the vessel wall is not increased.

FIG. 18 illustrates a projected view of the device 1810. This perspective shows the device having a first end 1812 and a second end 1814.

Figure 19:
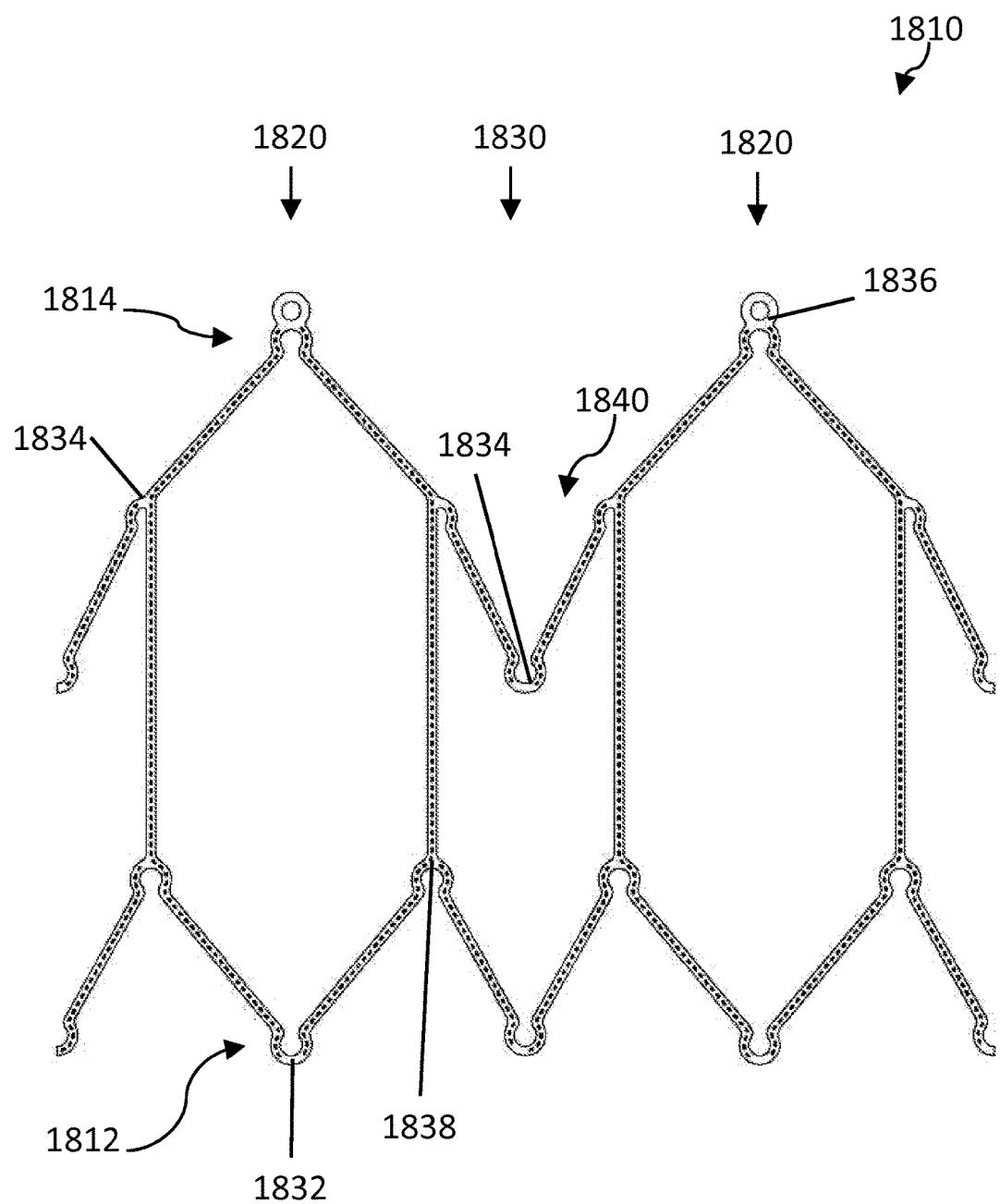

FIG. 19 illustrates a cut-and-flattened view of the device 1810. This perspective illustrates one embodiment of device 1810 having two substantially polygonal sections 1820, 1830. In one embodiment, polygon 1820 has an elongate, generally hexagonal shape, and polygon 1830 has six sides and a concavity 1840. The polygons 1820, 1830 may have substantially similar or different shapes, including one being narrower, taller, wider, thicker, thinner, otherwise different from the other, or combinations thereof. The bends of the polygons 1820, 1830 may have or be replaced with special structures, for example, two-connection horseshoe loop 1832, three-connection horseshoe loop 1838, half-horseshoe loop 1834, loop-and-ring horseshoe 1836, other structures, or combinations thereof. Different portions of the device 1810 may have different structures or combinations of these structures in order to produce useful mechanical characteristics. For example, first end 1812 may lack loop-and-ring horseshoe 1836 structures, while second end 1814 may have such a structure at one or more polygonal bends. The pattern formed on the first end 1812 of the device 1810 may be different from a pattern formed on the second end 1814 of the device 1810.

Figure 20:
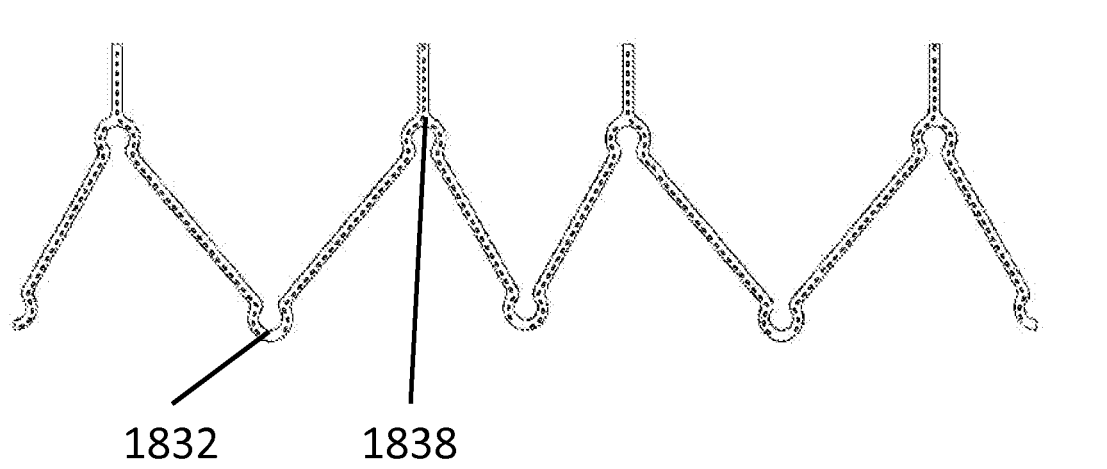

FIG. 20 illustrates a zoomed-in view of a first end of the device 1810. For example, FIG. 20 illustrates an embodiment of 1810 where the first end 1812 of device 1810 forms a pattern similar to a triangle wave with varying frequency. This pattern may provide and/or promote a desired spring constant. The constant may vary across the length or width of the device 1810. Further, the configuration or design of the structures (e.g. two-connection horseshoe loop 1832) may also contribute to varying spring constants across the device 1810.

Figure 21:
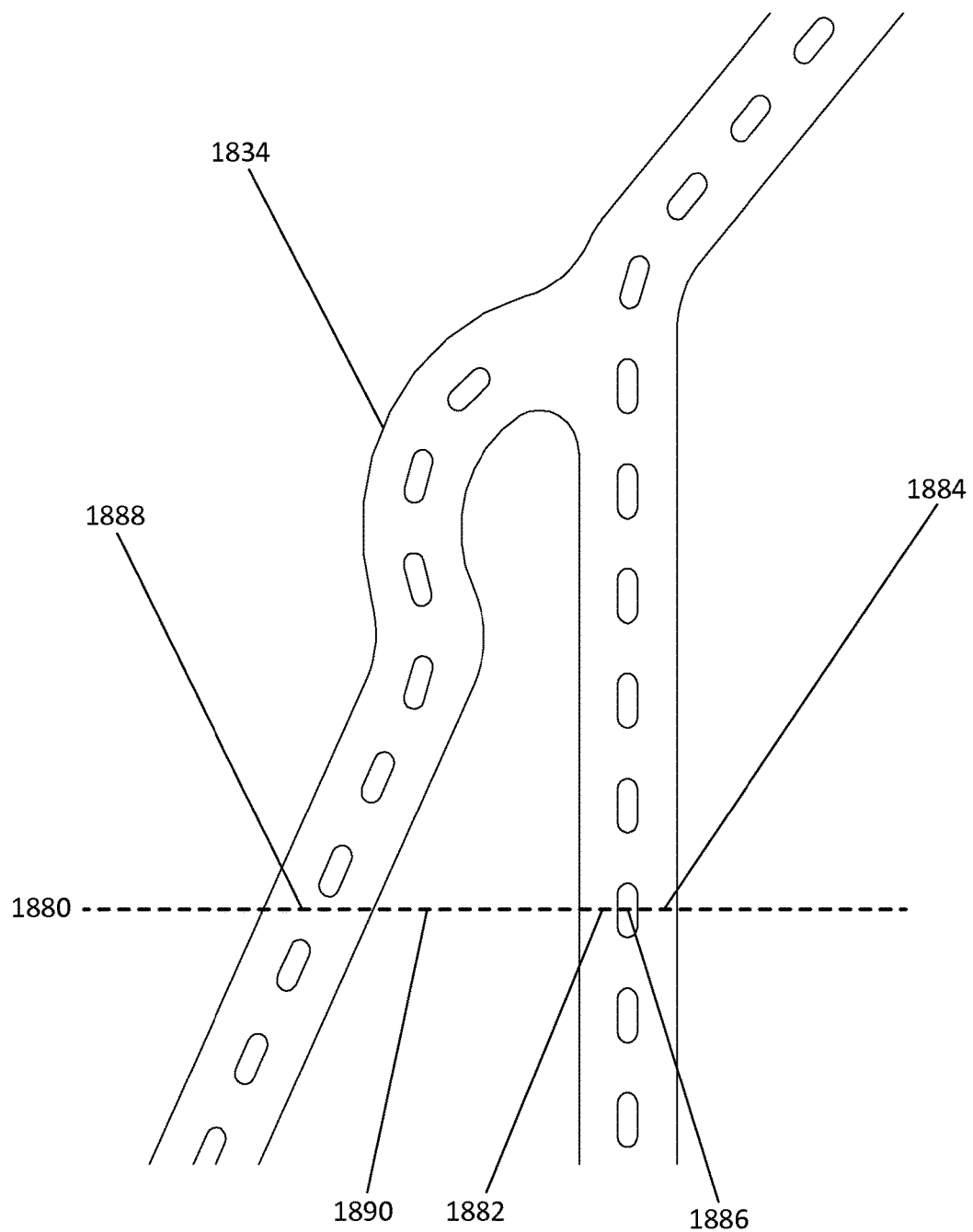

FIG. 21 illustrates a zoomed-in view of an area of the device 1810. Longitudinal region 1882 is located at a given longitudinal location denoted by dotted line 1880, and is separated at that longitudinal location from both longitudinal region 1888 and longitudinal region 1884. Longitudinal regions 1882 and 1888 are separated at the longitudinal location by a first kind of absence of device material 1890, where there is no contact between the device and the vessel wall, and the radius of curvature of the vessel wall is increased. Longitudinal regions 1882 and 1884 are separated at the longitudinal location by a second kind of absence of device material 1886, where there is no contact between the device and the vessel wall, and the radius of curvature of the vessel wall is not increased. In some embodiments, the second kind of absence of device material, where there is no contact between the device and the vessel wall, and the radius of curvature of the vessel wall is not increased, may promote or enable tissue ingrowth and/or may improve the anchoring of the device in the vessel wall. In some embodiments, the second kind of absence of device material, where there is no contact between the device and the vessel wall, and the radius of curvature of the vessel wall is not increased, may improve the flexibility of the device and/or reduce undesired levels of a stress concentration. More generally, it shall be understood that the following characteristics may in some embodiments pertain to the device herein described, and shown in one embodiment in FIGS. 18, 19, 20, and 21:

The separations between the longitudinal regions herein described are along a circumferential path of the device and/or the arterial wall, and "longitudinal" refers to the long axis of the vessel and/or the general direction of blood flow. The increase in radius of curvature of the vessel wall achieved by the first kind of absence of device material 1890 is achieved by blood flow or blood pressure. The lack of increase in radius of curvature of the vessel wall achieved by the second kind of absence of device material 1886 is achieved by the size or geometry of the area of absence, and/or by the partial or full isolation of the vessel wall spanning the second kind of absence from blood pressure or flow. The device may feature a single continuous surface that contacts the vessel wall. Regions may be defined as presences of material at a given longitudinal and/or circumferential location relative to the general path and/or position of the device and/or vessel.

Figure 22:
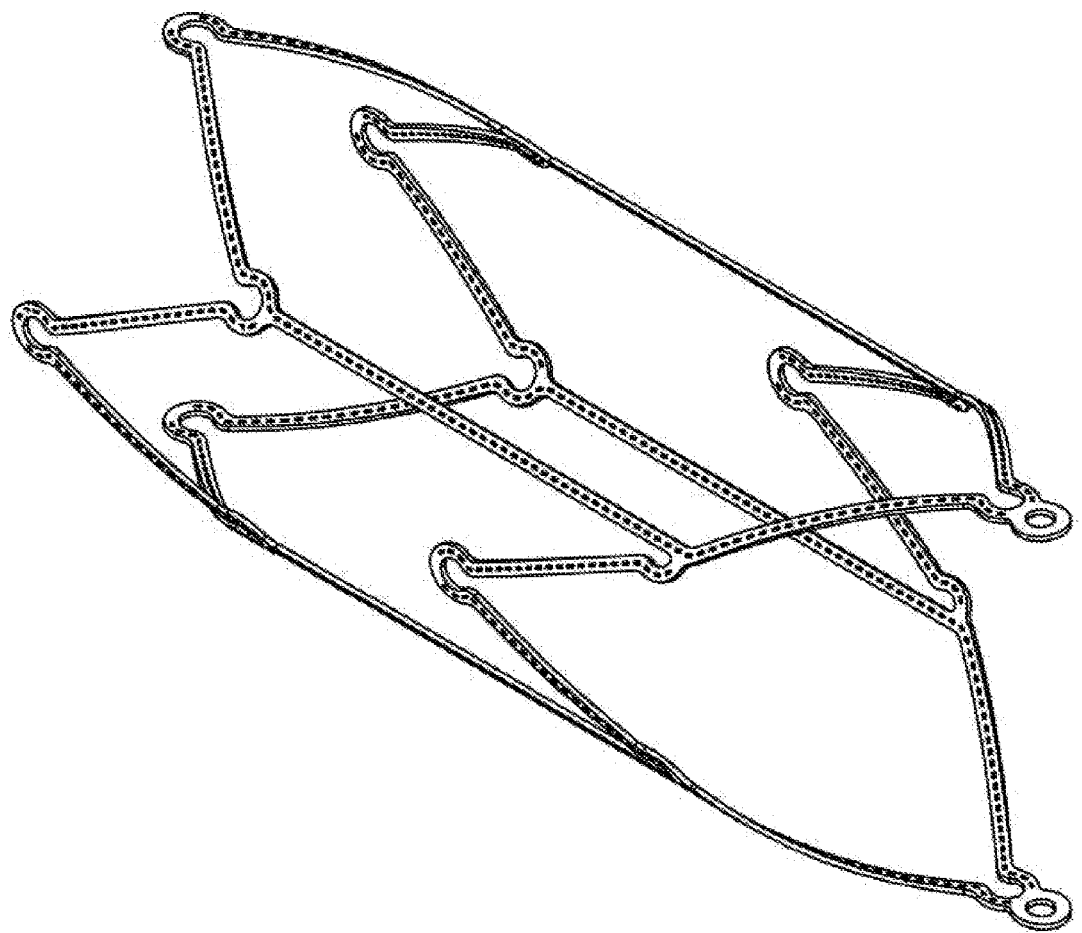
FIGS. 22, 23, 24, and 25 illustrate a perspective view, a cut-and-flattened view, an end view, and a zoomed-in view, respectively, of an embodiment of a device with three or more longitudinal regions, separated from other longitudinal regions at a given longitudinal location by one or both of (a) one or more of a first kind of absence of device material, where there is no contact between the device and the vessel wall, and the vessel wall at the absence is allowed to stretch and contract during the cardiac cycle, and/or (b) one or more of a second kind of absence of device material, where there is no contact between the device and the vessel wall, and the vessel wall at the absence is restricted from stretching and contracting during the cardiac cycle.
Figure 23:
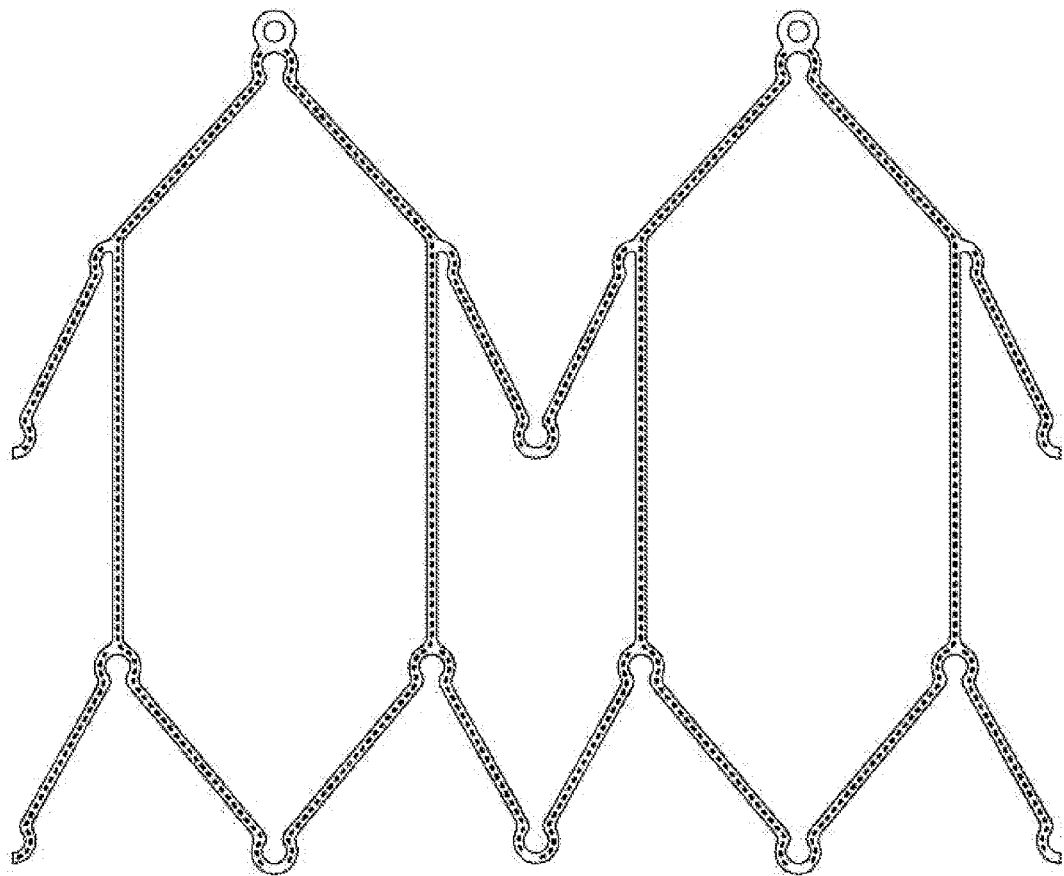
Figure 24:
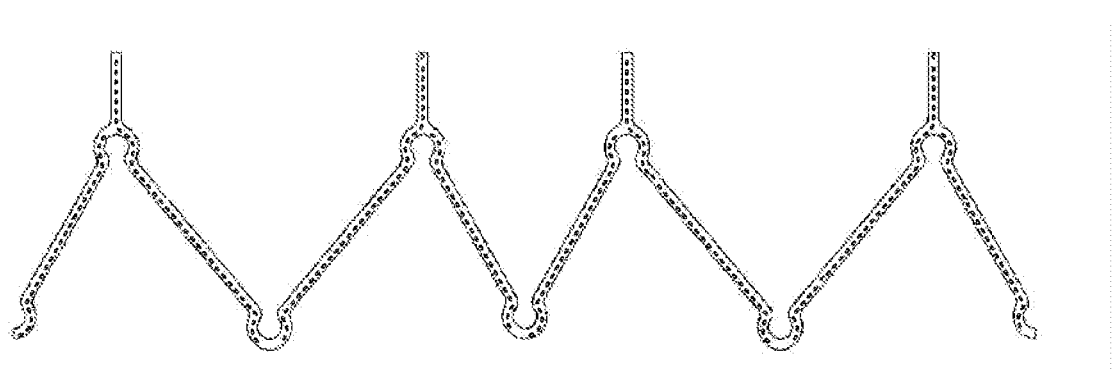
Figure 25:
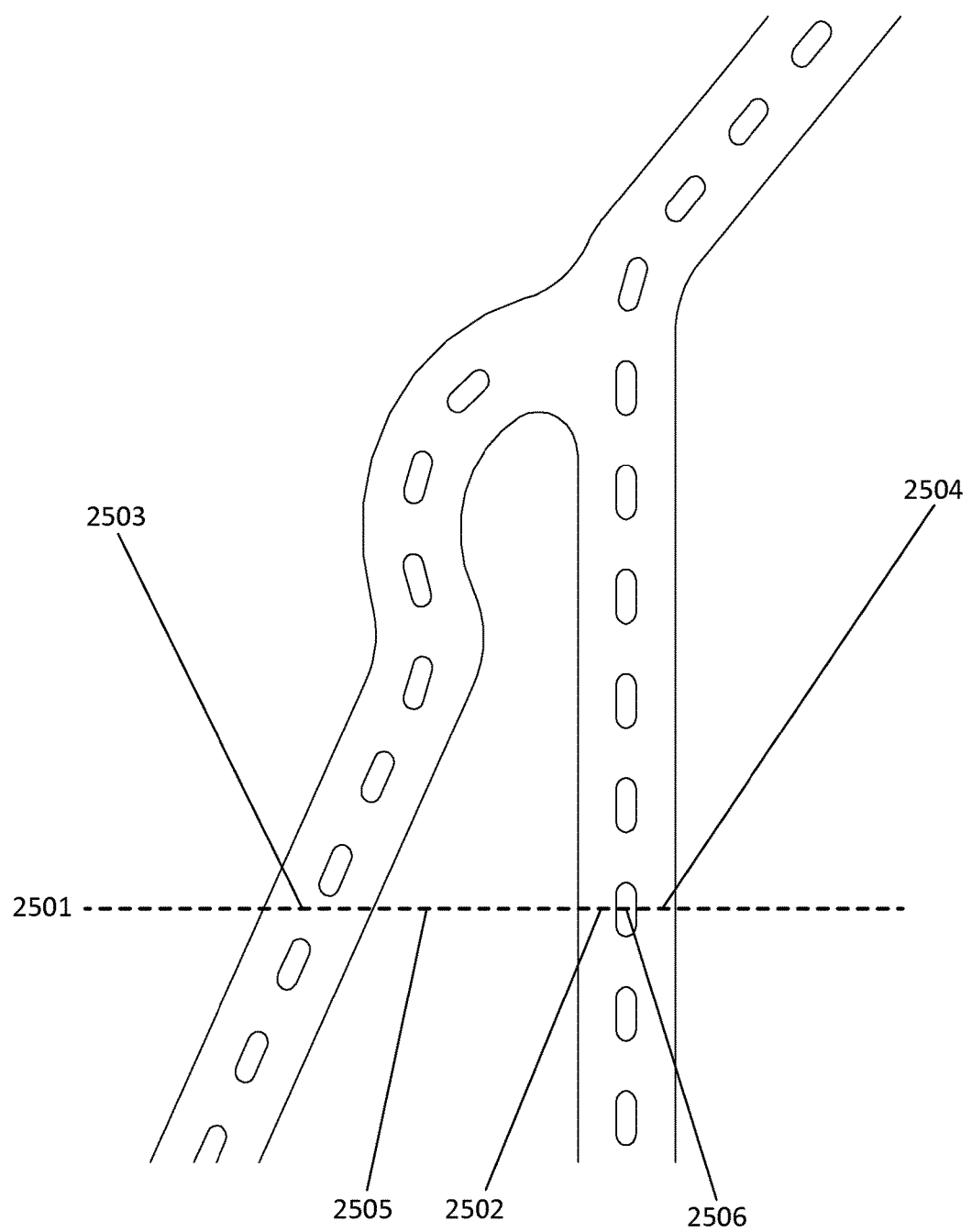

FIGS. 22, 23, 24, and 25 show an embodiment of a device with three or more longitudinal regions, separated from other longitudinal regions at a given longitudinal location by one or both of (a) one or more of a first kind of absence of device material 2505, where there is no contact between the device and the vessel wall, and the vessel wall at the absence is allowed to stretch and contract during the cardiac cycle, and/or (b) one or more of a second kind of absence of device material 2506, where there is no contact between the device and the vessel wall, and the vessel wall at the absence is restricted from stretching and contracting during the cardiac cycle. Of the one embodiment, FIG. 22 shows a projected view of the device; FIG. 23 shows a cut-and-flattened view; FIG. 24 shows a zoomed-in view of one end of the device; and FIG. 25 shows a zoomed-in view of another area of the device. Longitudinal region 2502 is located at a given longitudinal location (denoted by dotted line 2501) and is separated at that longitudinal location from both longitudinal region 2503 as well as longitudinal region 2504. Longitudinal regions 2502 and 2503 are separated at the longitudinal location by first kind of absence of device material 2505, where there is no contact between the device and the vessel wall, and the vessel wall at the absence is allowed to stretch and contract during the cardiac cycle. Longitudinal regions 2502 and 2504 are separated at the longitudinal location by second kind of absence of device material 2506, where there is no contact between the device and the vessel wall, and the vessel wall at the absence is restricted from stretching and contracting during the cardiac cycle. In some embodiments, the second kind of absence of device material, where there is no contact between the device and the vessel wall, and the radius of curvature of the vessel wall is not increased, may promote or enable tissue ingrowth and/or may improve the anchoring of the device in the vessel wall. In some embodiments, the second kind of absence of device material 2506, where there is no contact between the device and the vessel wall, and the radius of curvature of the vessel wall is not increased, may improve the flexibility of the device and/or reduce undesired levels of a stress concentration. More generally, it shall be understood that the following characteristics may in some embodiments pertain to the device herein described, and shown in one embodiment in FIGS. 22, 23, 24, and 25:

The separations between the longitudinal regions herein described are along a circumferential path of the device and/or the arterial wall, and "longitudinal" refers to the long axis of the vessel and/or the general direction of blood flow. The stretching and contracting of the vessel wall achieved by the first kind of absence of device material is achieved by blood flow or blood pressure. The restriction of stretching and contracting of the vessel wall achieved by the second kind of absence of device material is achieved by the size or geometry of the area of absence, and/or by the partial or full isolation of the vessel wall spanning the second kind of absence from blood pressure or flow. The device may feature a single continuous surface that contacts the vessel wall. Regions may be defined as presences of material at a given longitudinal and/or circumferential location relative to the general path and/or position of the device and/or vessel.

FIGS. 26, 27, 28, and 29 show an embodiment of a self-expanding implantable device 2610 that is unsheathed intravascularly to achieve deployment. In at least some embodiments, device 2610 provides substantial circumferential coverage and/or radial force in one or more regions that alternate with one or more regions of substantially less circumferential coverage and/or radial force, using a structure with strut angles that are conducive to resheathability and/or radial expansion.

Figure 26:
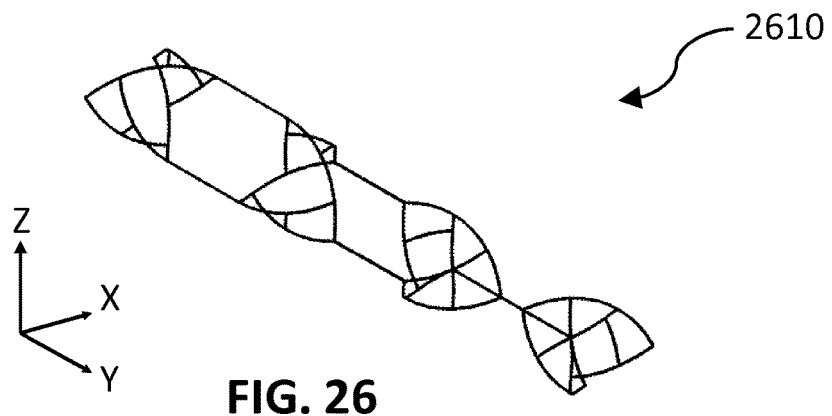
FIGS. 26, 27, 28, and 29 illustrate a perspective view, a side view, a top view, and a view in proximity to a sheath, respectively, of an embodiment of a self-expanding implantable device that is unsheathed intravascularly to achieve deployment.

FIG. 26 shows a perspective view of the device 2610. The angles and directions shown may be measured or constrained within curved two-dimensional planes characterized by the circumferential shape of the sheath and/or the device, or circling the longitudinal axis of the sheath, device, and/or vessel.

Figure 27:
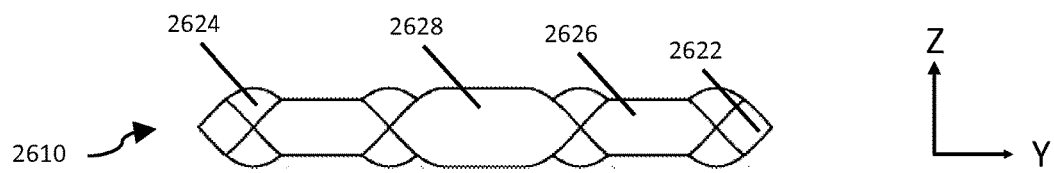
Figure 28:
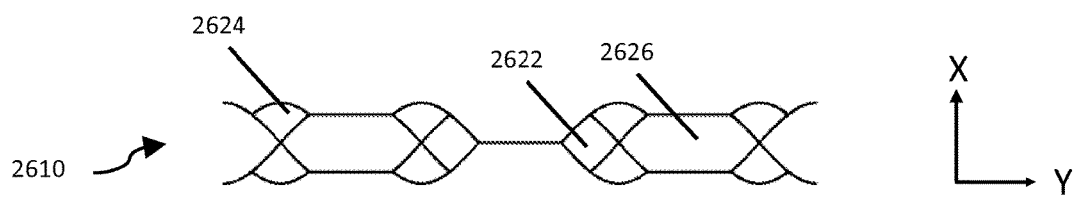

FIG. 27 shows a side view of the device 2610. A three-dimensional embodiment of device 2610 may be constructed so it has the following pattern when viewed from a side view. The structure may have an alternating pattern of geometric shapes (e.g. polygons 2626, 2628, which may be substantially hexagonal) having differing shapes, sizes, orientations, other characteristics, or combinations thereof. For example, polygon 2628 may be oriented such that when viewed from a side view it appears to have displacement in both an x direction and a y direction, but when viewed from the top, it appears to have displacement in primarily only a y direction. Polygon 2626 may be oriented such that it appears to have displacement in each of an x direction, a y direction, and a z direction when viewed from the side or top views. These arrangements may, for instance, be constructed by orienting polygon 2628 and polygon 2626 at 45-degree angles to each other. FIG. 28 shows a top view of the device 2610.

Figure 29:
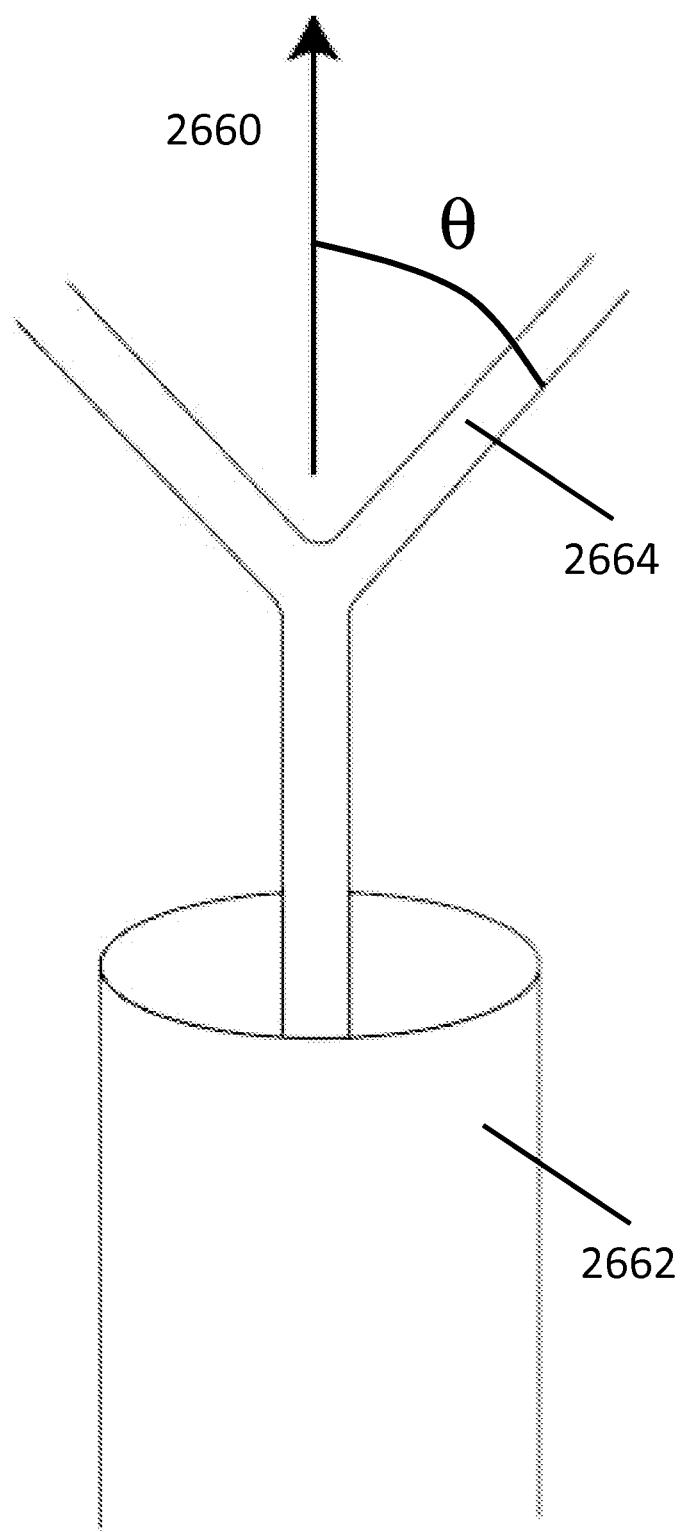

FIG. 29 illustrates a portion of device 2610 in proximity to a sheath. Arrow 2660 denotes the direction of the sheath 2662's movement relative to the device 2610 during resheathing, and in this embodiment, also a direction normal to the leading edge of sheath 2662. Angle θ denotes an angle between the direction of arrow 2901 and the divergence direction of region 2664 (the divergence direction measured from the edge of region 2664 nearest the sheath 2662), Angle θ being less than 90-degrees from the direction of arrow 2660. More generally, it shall be understood that the following characteristics may in some embodiments pertain to the device 2610 herein described, and shown in one embodiment in FIGS. 26, 27, 28, and 29. The direction of the sheath 2662's movement and a direction normal to the leading edge of the sheath 2662 at any given location may or may not be the same direction. Convergence directions, analogous to the divergence direction described above, may be measured from the edge of a region facing the sheath 2662.

Figure 30:
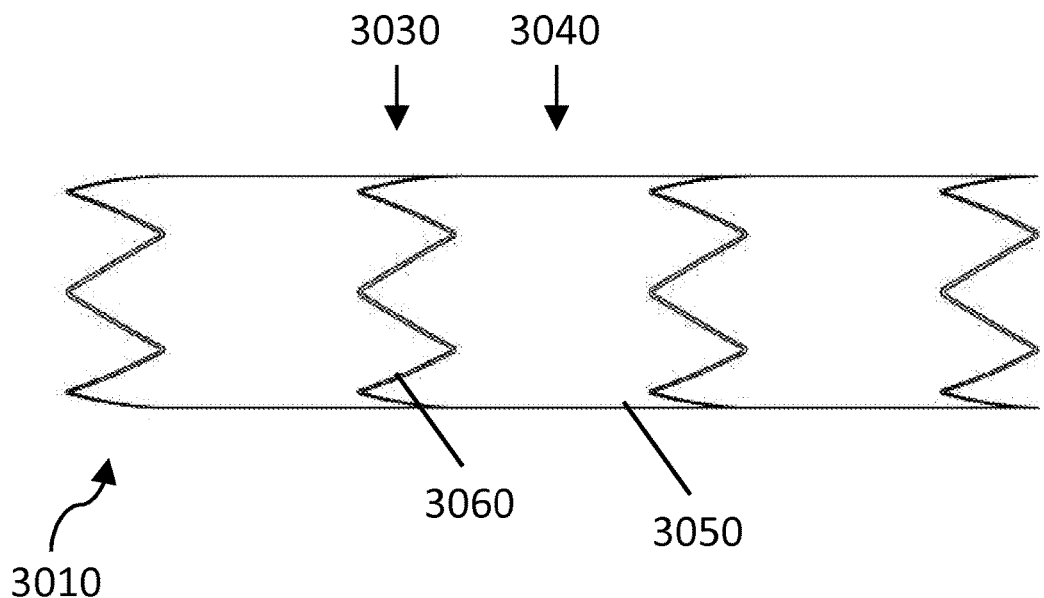
FIGS. 30, 31, 32, and 33 illustrate a top view, a side view, a projected view, and another projected view, respectively, of an example of a device with regions of a first kind that provide substantial circumferential coverage and/or radial force, interspersed longitudinally (relative to the long axis of the blood vessel) with regions of a second kind that provide considerably less circumferential coverage and/or radial force.
Figure 31:
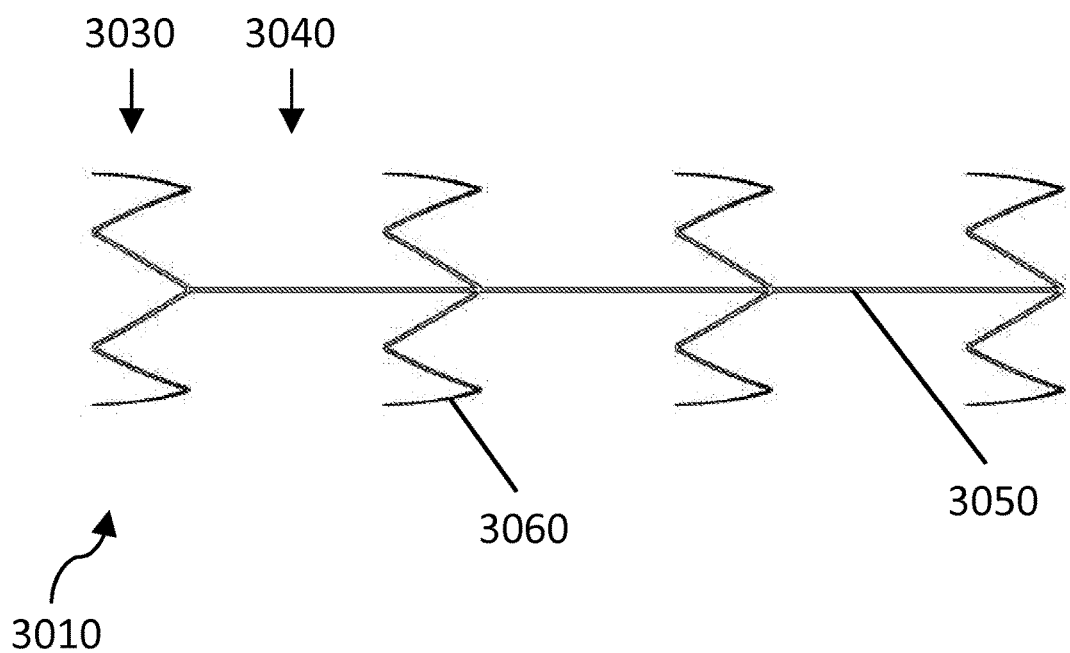
Figure 32:
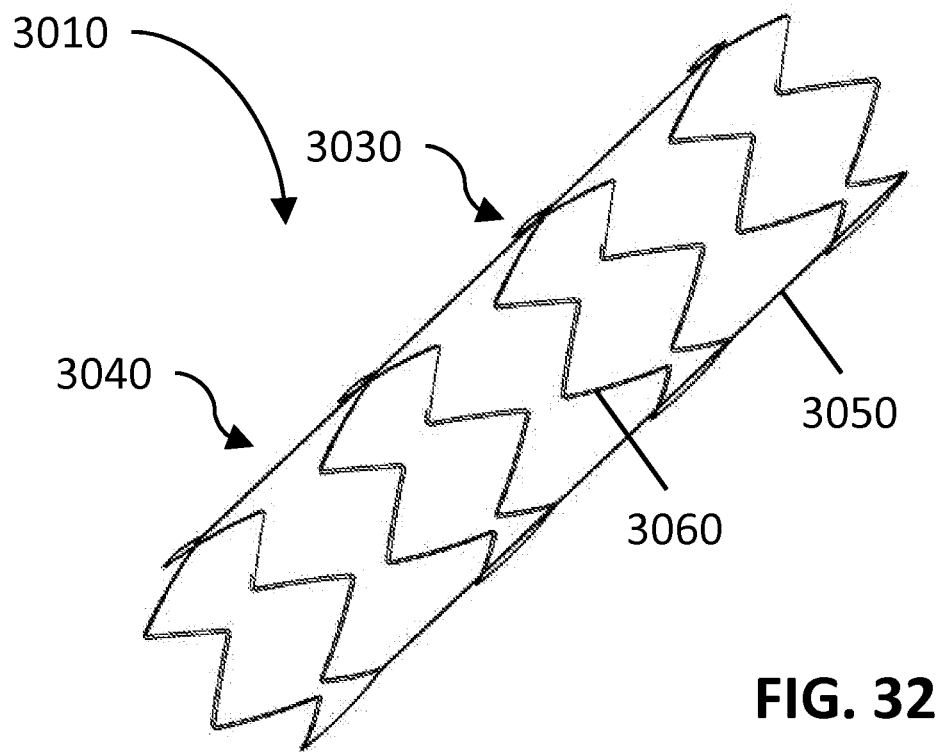
Figure 33:
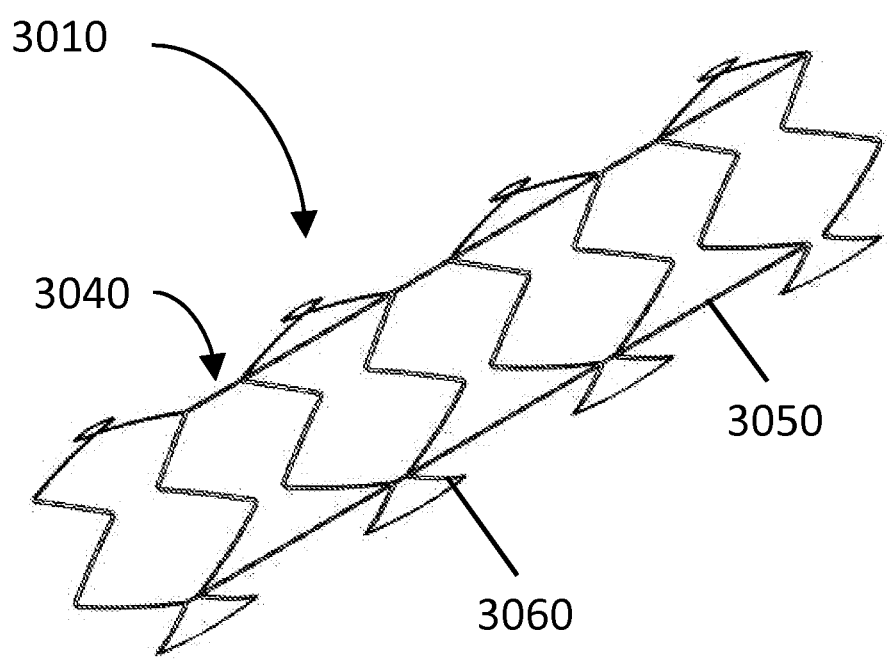

FIGS. 30, 31, 32, and 33 show an example of a device 3010 with a first plurality of regions 3030 that provide substantial circumferential coverage and/or radial force, interspersed longitudinally (relative to the long axis of the blood vessel) with a second plurality of regions 3040 that provide considerably less circumferential coverage and/or radial force. FIGS. 30 and 31 show top and side views of the device 3010, respectively, while FIGS. 32 and 33 show different projected views of the device 3010. Regions 3030 are examples of regions of substantial circumferential coverage and/or radial force, interspersed longitudinally with regions 3040 that provide considerably less circumferential and/or radial force. More generally, it shall be understood that the following characteristics may, in some embodiments, pertain to the device 3010. The regions 3030 of substantial coverage may range in number from very few regions (including just one region), to many regions. The regions 3040 of substantially less coverage may range in number from very few regions (including just one region), to many regions. Rather than or in addition to distinct regions of circumferential coverage, distinct regions of longitudinal coverage may also be used. Regions 3030 of substantial coverage may be connected by a single longitudinal or circumferential link 3050, or by a plurality of such members, or varying numbers of links.

FIG. 30 illustrates a top view of an embodiment of device 3010 having regions 3030 of substantial circumferential coverage and regions 3040 having considerably less circumferential coverage 3030. The characteristics of these regions 3030, 3040 may be the result of a particular configuration of rings 3060 and/or links 3050. For example, as shown in FIG. 30, device 3010 may have rings 3060 comprised of a material having a substantially triangular waveform. Rings 3060 may exert radial forces when compressed by, for example, a lumen or a vessel wall. As such, these regions 3030 may urge themselves against a vessel wall and provide substantial coverage. In addition to defining regions 3030, the rings 3060 may define the outer boundary or edge of a region 3030 having few or no structures and therefore defining a region 3040 having considerably less circumferential coverage.

FIG. 31 illustrates a side view of an embodiment of the device 3010. As shown, members 3050 may be arranged on opposite sides of the device 3010; however, links 3050 need not be opposite each other. Links 3050 may be arranged near each other, leaving a substantial portion of the circumference of device 3010 without links 3050. Links 3050 may be elongate structures that connect rings 3060.

FIGS. 32 and 33 illustrate perspective views of an embodiment of the device 3010.

Figure 34:
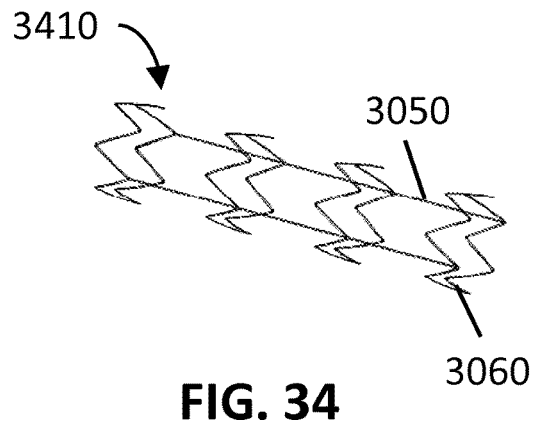
FIGS. 34, 35, 36, 37, 38, and 39 illustrate perspective views of some embodiments of devices that partially resorb, dissolve, or degrade.
Figure 35:
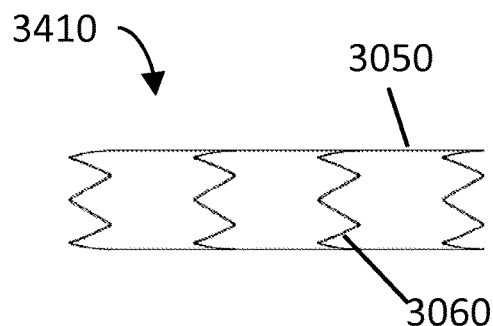
Figure 36:
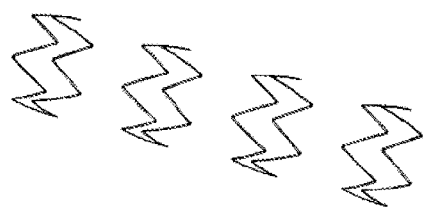
Figure 37:
Figure 38:
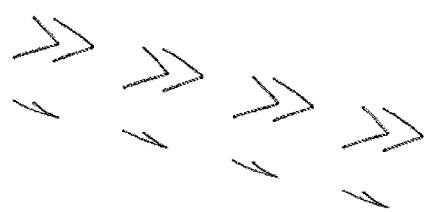
Figure 39:

FIGS. 34, 35, 36, 37, 38, and 39 show some embodiments of a device 3410 that partially resorb, dissolve, or degrade. FIGS. 34 and 35 show separate views of a beginning structure, prior to partial resorption, dissolution, or degradation. FIGS. 36 and 37 show separate views of a set of possible residual structures remaining after the resorption, dissolution, and/or degradation of part of a beginning structure. FIGS. 38 and 39 show separate views of a different set of possible residual structures remaining after the resorption, dissolution, and/or degradation of part of a beginning structure. In the case of FIGS. 36 and 37, residual structures are continuous circumferentially, but no longer connected longitudinally. In the case of FIGS. 38 and 39, residual structures have both longitudinal and circumferential discontinuities. More generally, it should be understood that devices that partially resorb, dissolve, and/or degrade: may provide a small number of residual structures (as few as one), or many residual structures; may introduce circumferential discontinuities, longitudinal discontinuities, or both; may provide stretching forces and/or compressive forces on a vessel before, during, and/or after partial resorption, dissolution, and/or degradation; may include combinations of these features or characteristics.

In addition, the structures may be comprised of biocompatible metals and/or polymers, and may feature drugs or other chemical agents intended to affect rates of resorption, dissolution, and/or degradation, and/or to promote a desired biological response. For example, certain regions or structures may be constructed from materials that are conducive to resorption such as iron, magnesium, zinc, or certain polymers, while other regions or structures may be constructed from materials that do not rapidly degrade such as tantalum, titanium, chromium, or certain polymers. Specifically, FIGS. 36 and 37 illustrate a device 3410, post-resorption, where the device 3410's links 3050 were constructed from a resorption-prone material and device 3410's rings 3060 were constructed from a generally resorption-resistant material. As such, FIGS. 36 and 37 illustrate that after a given period of time, links 3050 have substantially resorbed while rings 3060 remain substantially intact. As another specific example, FIGS. 38 and 39 illustrate a device 3410, post-resorption, where the device 3410's links 3050 and portions of rings 3060 were constructed from a resorption-prone material and other portions of device 3410's rings 3060 were constructed from a generally resorption-resistant material. As such, FIGS. 38 and 39 illustrate that after a given period of time, links 3050 and regions of rings 3060 have substantially resorbed while other regions of rings 3060 have remained substantially intact.

Figure 40:
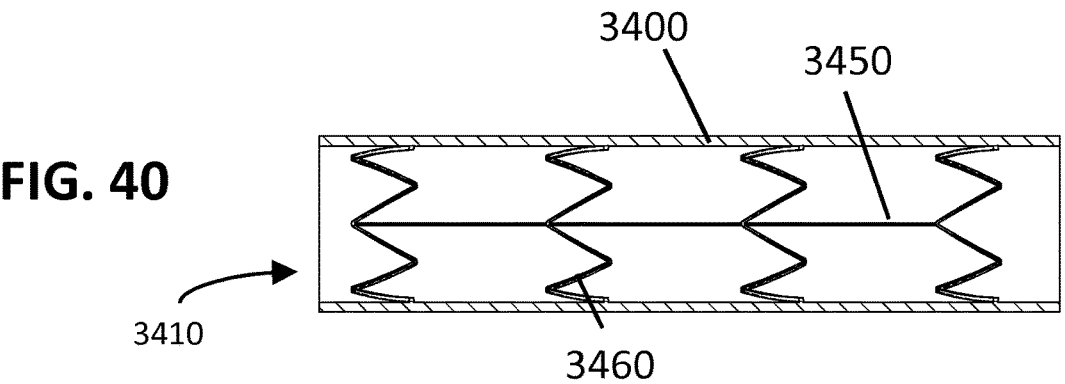
FIGS. 40, 41, and 42 illustrate side views of a device that partially resorbs, dissolves, or degrades at various stages that may occur after implantation.
Figure 41:
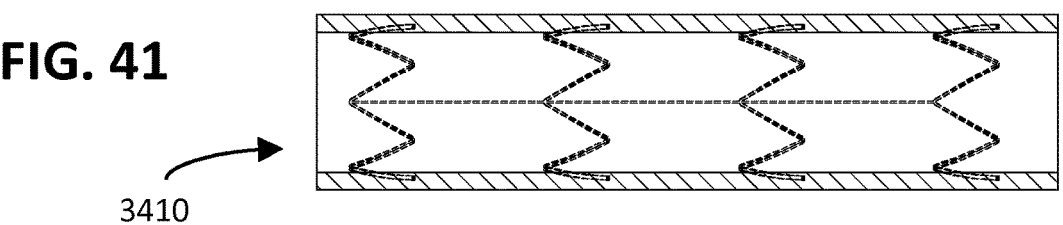
Figure 42:
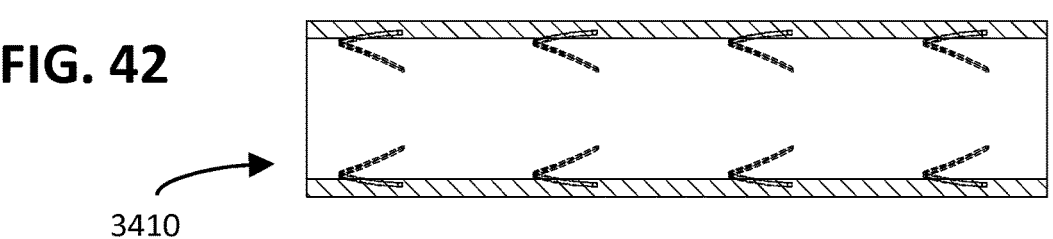

FIGS. 40, 41, and 42 illustrate side views of a device 3410 that partially resorbs, dissolves, or degrades (such as those shown in FIGS. 34, 35, 36, 37, 38 and 39) at various stages that may occur after implantation.

FIG. 40 illustrates an embodiment of the device 3410 deployed within a vessel 3400, prior to significant integration into the vessel 3400 (as might result from biological responses known to occur upon implantation of a stent). Device 3410 may include links 3450 and rings 3460.

FIG. 41 illustrates an embodiment of the device 3410 integrated into the vessel wall, but prior to significant resorption, dissolution, or degradation of the device 3410.

FIG. 42 illustrates an embodiment of the device 3410 after at least partial resorption, dissolution, or degradation of device 3410 has occurred. For example, links 3450 have resorbed and residual structures (e.g., portions of rings 3460) which have integrated into the vessel wall 3400. The integration of the residual structures into the vessel wall may, in some embodiments, prevent movement of the residual structures to undesired locations (preventing, for example, embolization of the residual structures into more distal vasculature).

FIGS. 43, 44, and 45 illustrate a variety of views of some embodiments of devices 4310, 4410, 4510 made of one or more elastic metals and/or polymers (e.g., Nitinol) that assumes a shape, when implanted into a blood vessel, that causes stretch receptors in the vessel wall to be activated. The devices 4310, 4410, 4510 may be comprised of substantially one continuous member that assumes a curved configuration upon delivery via catheter into a blood vessel. In one embodiment, the devices 4310, 4410, 4510 are made of biocompatible metal (including at least some portion comprised of Nitinol), assume a substantially straightened configuration while within a delivery catheter, and assume a curved configuration upon exiting a delivery catheter that causes strain to be focused on a particular region of the vessel wall that has a high concentration of stretch receptors. Some of the embodiments of the devices 4310, 4410, 4510 may have an end loop 4330, 4430, 4530 or other structure designed to (a) reduce or prevent vessel trauma, and/or (b) facilitate deployment (such as by electrolysis or mechanical release) and/or retraction and/or radiographic visualization, and/or (c) provide a desired concentration and/or lack of concentration of pressure and/or force on a vessel.

Figure 43A:
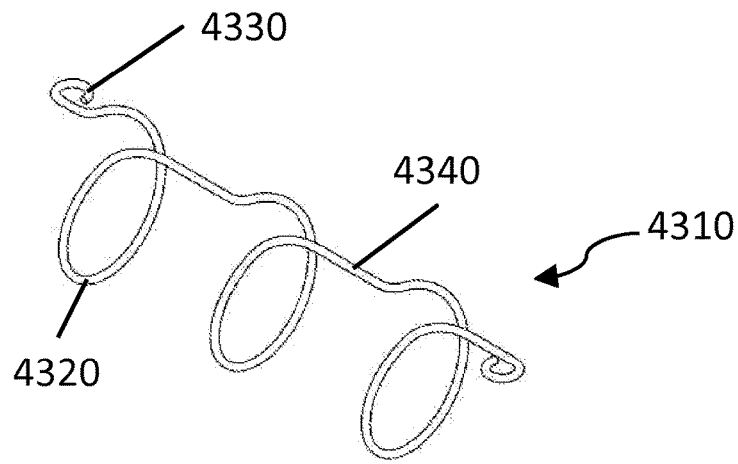
FIGS. 43A, 43B, 43C, and 43D illustrate perspective, front, side, and top-down views, respectively, of an embodiment of a device made of one or more elastic metals and/or polymers that assumes a shape, when implanted into a blood vessel, which causes stretch receptors in the vessel wall to be activated.
Figure 43B:
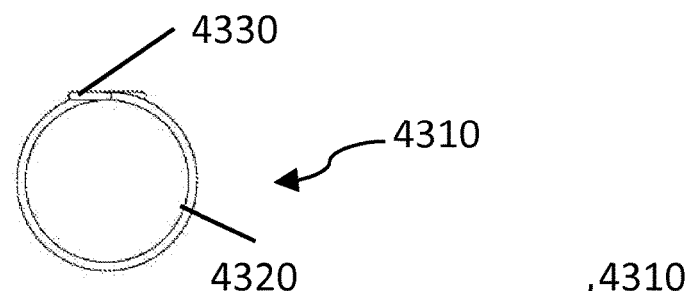
Figure 43C:
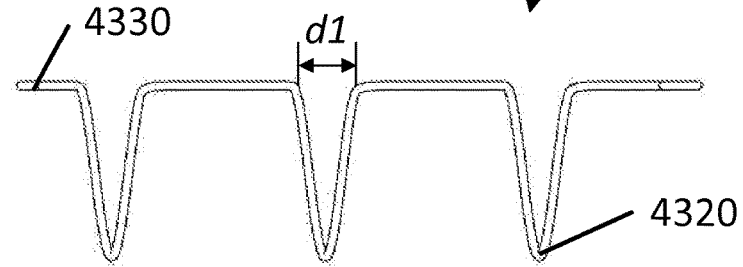
Figure 43D:
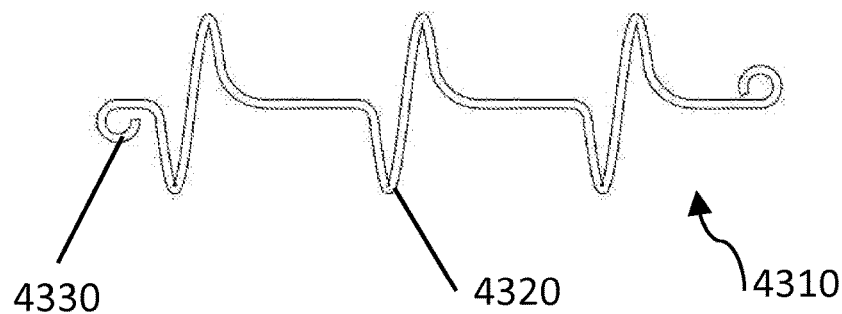

FIG. 43A illustrates a perspective view of device 4310. Device 4310 may comprise a substantially elongate piece 4340, forming loops 4320 and end loops 4330. Loops 4320 may be substantially parallel to each other and be substantially circular. End loops 4330 may be substantially perpendicular to loops 4320 and may be of a smaller size. FIG. 43B illustrates a front view of device 4310, including loops 4320 in a substantially circular configuration. FIG. 43C illustrates a side view of device 4310, including a distance of travel d1 of the loops 4320. FIG. 43D illustrates a top view of device 4310. In some embodiments, distance of travel d1 of the loops 4320, the radius of loops 4320, and the angle between loops and the general axis of a blood vessel may vary within device 4310.

Figure 44A:
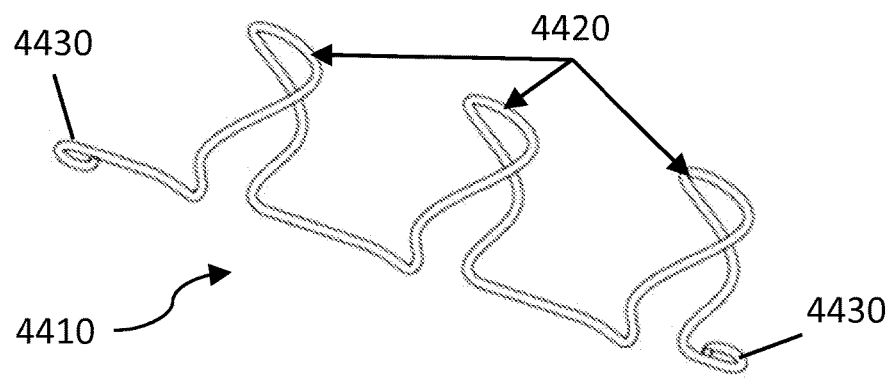
FIGS. 44A, 44B, and 44C illustrate perspective, side, and top-down views, respectively, of an embodiment of a device made of one or more elastic metals and/or polymers that assumes a shape, when implanted into a blood vessel, which causes stretch receptors in the vessel wall to be activated.
Figure 44B:
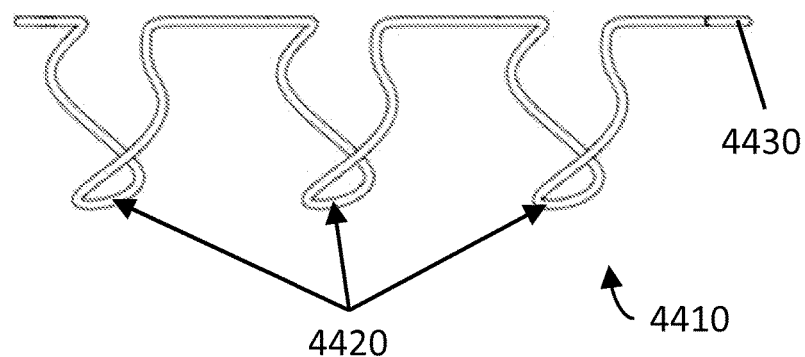
Figure 44C:
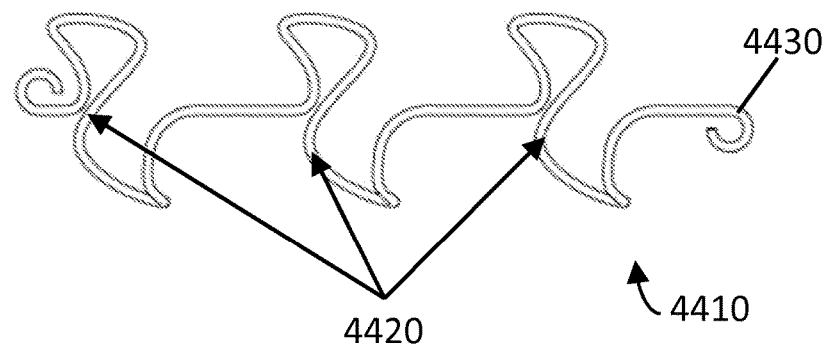

FIG. 44A illustrates a perspective view of device 4410, including loops 4420. Loops 4420 may be described as following a path that angles distally for at least some distance, and a path that angles proximally for at least some distance. FIG. 44B illustrates a side view of device 4410. FIG. 44C illustrates a top-down view of device 4410, including loops 4420, which in some embodiments may also be described as having a substantially zig-zag shape.

Figure 45A:
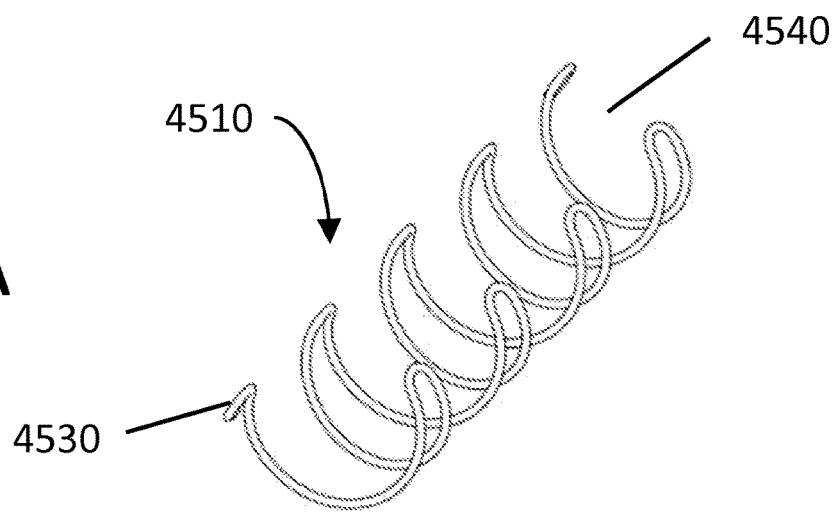
FIGS. 45A, 45B, and 45C illustrate perspective, side, and top-down views, respectively, of an embodiment of a device made of one or more elastic metals and/or polymers that assumes a shape, when implanted into a blood vessel, which causes stretch receptors in the vessel wall to be activated.

FIG. 45A illustrates a side view of device 4510. In one embodiment, the device 4510 may feature a radius of curvature, relative to its gross longitudinal axis (i.e., when viewed from one end), that is larger where nearer to the location 4520 where the primary wire reverses circumferential direction, thus creating higher strain in the vessel wall where it spans reversing regions of the primary wire. The reversal of circumferential direction may take the form of various shapes or structures. For example, the reversal may take the form of one or more of: a sharp change in direction, a gradual change in direction; a change in direction in two dimensions; a change in direction in three-dimensions; a complete change of direction; a partial change of direction; other changes; or a combination thereof.

A circumferential discontinuity 4540 can be seen that runs the length of the device 4510, and an end view of the device 4510 reveals a circumferential region in which the discontinuity is preserved. It shall be understood, though, that in some embodiments, the circumferential discontinuity 4540 may run only part of the length of the device 4510, and that the circumferential discontinuity 4540 may occupy varying circumferential locations, including some in which the circumferential region is not visibly preserved from an end view. At some longitudinal locations, the discontinuity 4540 is bounded circumferentially at the location 4520 where the primary wire reverses circumferential direction.

More generally, in a variety of embodiments, the device 4410 and method of FIG. 45A may: feature a radio-opaque coil wound around a Nitinol core wire, with the two attached to one another at least at the distal end; be placed endovascularly via catheter, or extravascularly through surgery; be wrapped around the exterior of a blood vessel; and have resorbable, degradable, dissolvable, and/or absorbable members which, upon resorbing, degrading, dissolving, or absorbing, transfer residual force in the device 4510 and/or vessel in a favorable manner, such as to locate strains to favorably activate stretch receptors in the vessel wall.

Figure 45B:
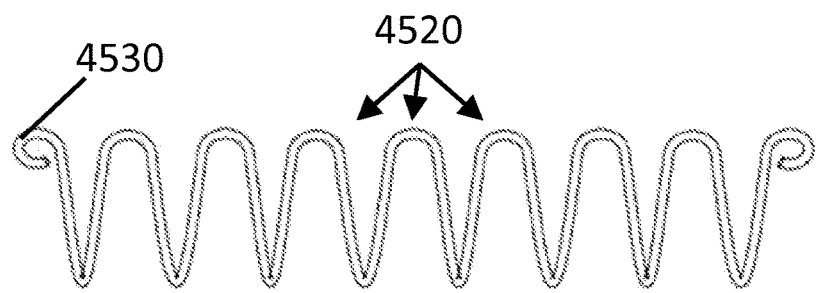
Figure 45C:
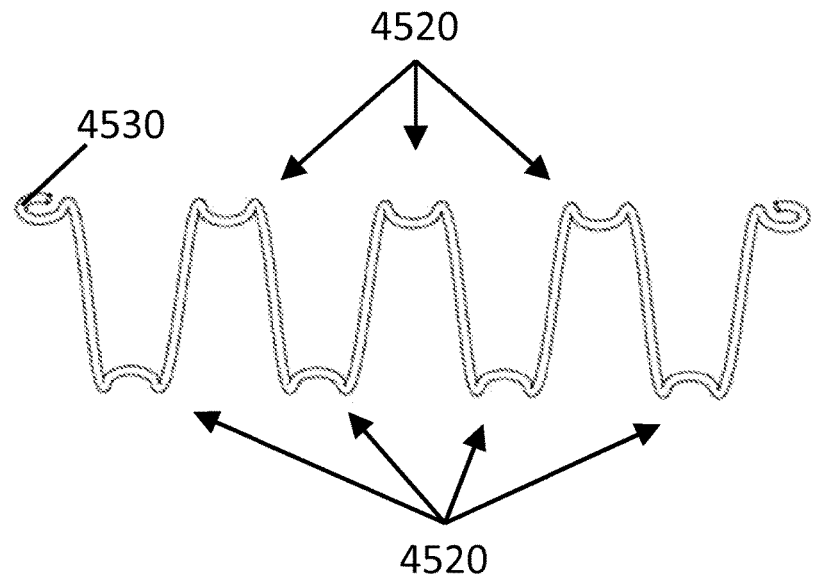

FIG. 45B illustrates a side view of device 4510. FIG. 45C illustrates a top-down view of device 4510.

Figure 46:
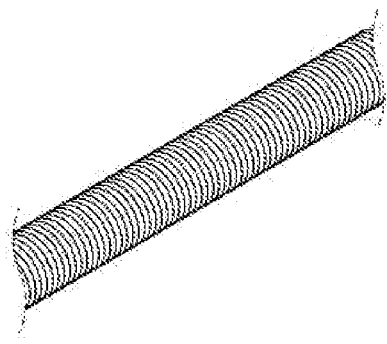
FIGS. 46, 47, 48, and 49 illustrate zoomed-in views of a segment of a device, each exemplifying embodiments of the general construction of the device.
Figure 47:
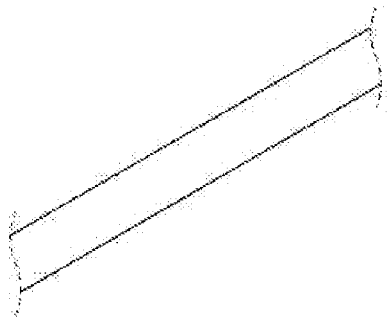
Figure 48:
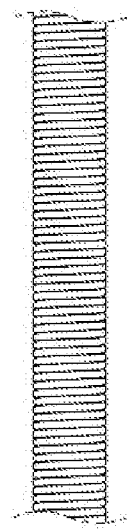
Figure 49:
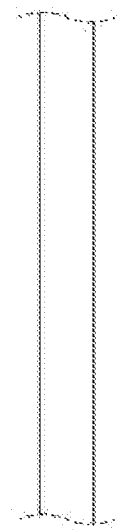

FIGS. 46, 47, 48, and 49 show zoomed-in views of a segment of a device, each exemplifying embodiments of the general construction of the device: in FIGS. 47 and 49, a substantially single structure, as in a wire or continuous segment of material, and in FIGS. 46 and 48, a wire or continuous segment of material surrounded by a coil. More generally, it should be understood that devices exemplified by FIGS. 43, 44, 45, 46, 47, 48, and 49 may include ends or segments that are curved or otherwise shaped in a manner that (a) reduces or prevents vessel trauma, and/or (b) facilitates deployment and/or retraction and/or radiographic visualization, and/or (c) provides a desired concentration and/or lack of concentration of pressure and/or force on a vessel.

Figure 50:
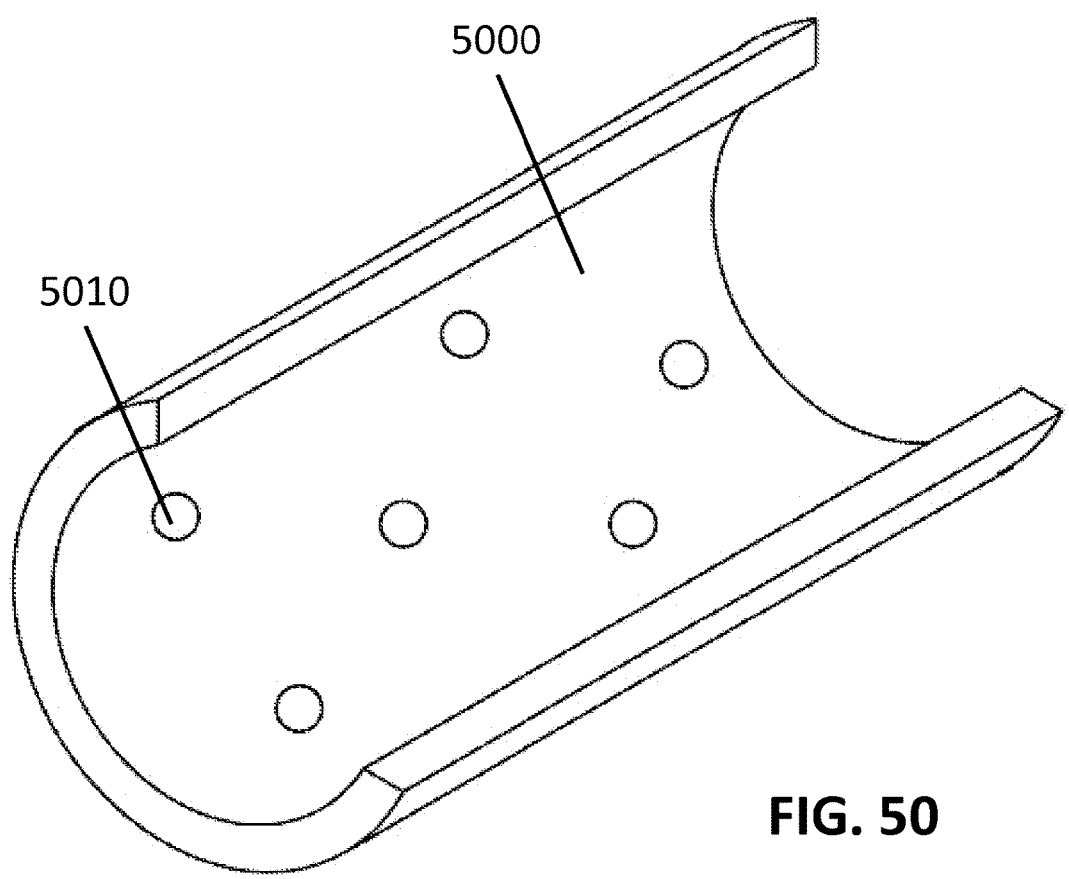
FIG. 50 illustrates a section of a blood vessel in which devices and/or methods have been employed to alter the chemical, biological, and/or mechanical properties and/or structural characteristics of a blood vessel wall and/or surrounding tissues, in order to effect changes in the strain occurring at some or all baroreceptors within the vicinity of the alterations.

FIG. 50 shows a section of a blood vessel in which devices and/or methods have been employed to alter the chemical, biological, and/or mechanical properties and/or structural characteristics of a blood vessel wall 5010 and/or surrounding tissues, in order to effect changes in the strain occurring at some or all baroreceptors within the vicinity of the alterations 5010. Alterations 5010 to the blood vessel wall 5000 may be caused by (for example) an ablation device that alters the mechanical properties of tissues. In the case that the alteration 5010 assumes a stiffness that differs from the target tissue's original stiffness (for example, an increased stiffness), the stress distribution in the blood vessel wall 5000 that results from blood pressure will change (and, for example, may especially change at high pressures within the cardiac cycle). The new stress distribution may result in higher strain at some or all baroreceptors, compared with the strain that would have occurred at one or more given blood pressures without the intervention. More generally, it should be understood that the following characteristics may pertain to one or more alterations to a blood vessel herein described and shown in one embodiment in FIG. 50: alterations 5010 may affect any combination of tissue types found within or around the blood vessel, including but not limited to one or more of the following: the intima, media, adventitia, surrounding tissues, or distinct cell types found within these tissues; alterations 5010 may create stress redistributions by increasing the stiffness of some tissues and/or decreasing the stiffness of some tissues; alterations 5010 may be similar to lesions created in cardiac tissue during ablation procedures; alterations 5010 may be permanent or temporary; alterations 5010 may be concentrated on a side of a vessel and/or within an axial region of a vessel where baroreceptors are thought, determined, or known to be concentrated; alterations 5010 may be generally circular; circular alterations 5010 may each assume an area that is approximately 0.2 mm to 4 mm in diameter; alterations 5010 may be concentrated on a side of a vessel and/or within an axial region of a vessel where baroreceptors are thought, determined, or known to be less concentrated than in another (such as opposing) region; alterations 5010 may cause formation of new tissue (for example, scar tissue), and/or may cause death of some tissue, and/or may damage some tissue.

Figure 51:
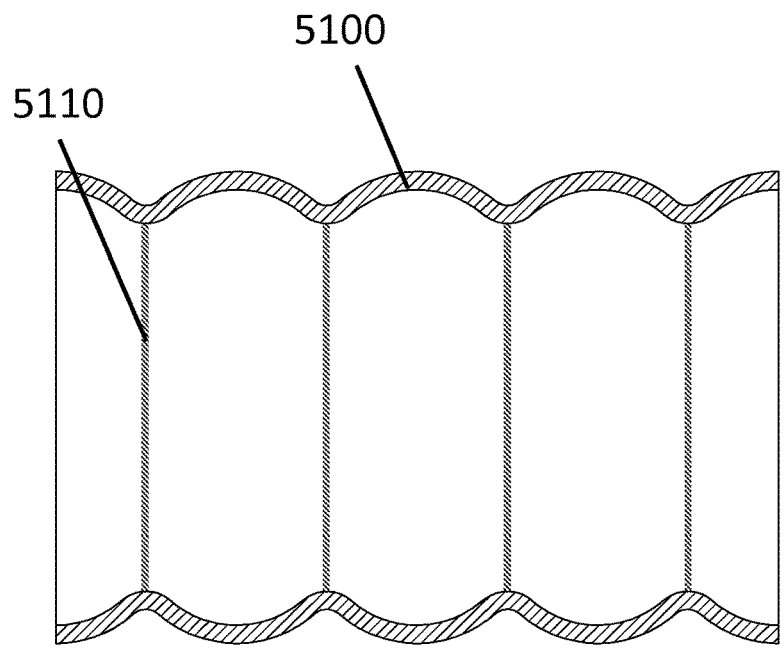
FIG. 51 illustrates a cross section of an altered blood vessel that has been stiffened along a number of generally circumferential paths.

FIG. 51 shows a cross section of an altered blood vessel 5100 that has been stiffened along a number of generally circumferential paths 5110. As blood pressure increases during the cardiac cycle, stiffened regions resist deformation more than unstiffened regions, creating advantageous changes in baroreceptor activation (compared with an untreated vessel). In some embodiments, baroreceptor activation is more greatly changed at higher blood pressures than at lower blood pressures during the cardiac cycle, and/or minimally changed or not at all changed at lower blood pressures during the cardiac cycle, which may help prevent baroreceptor activation and/or advantageous effects of baroreceptor activation, such as treatment of hypertension, from diminishing over time. In some embodiments, it may be advantageous to alter stiffness (for example, increase stiffness) in the vessel 5100 when the vessel diameter is similar to that occurring during at least one of the following: (a) diastole, (b) generally low pressure periods of the cardiac cycle, (c) periods of the cardiac cycle at which baroreceptor activation is desirably minimized, in comparison with other periods of the cardiac cycle. In some embodiments, it may be advantageous to alter stiffness in the vessel 5100 when the vessel diameter is similar to that occurring during at least one of the following: (a) systole, (b) generally high pressure periods of the cardiac cycle, (c) periods of the cardiac cycle at which baroreceptor activation is desirably maximized, in comparison with other periods of the cardiac cycle. In some embodiments, a desired vessel diameter is maintained during alteration by providing positive or negative pressure, for example by isolating a region within the blood vessel 5100 (for example, using one or more inflatable members) and injecting or aspirating a fluid and/or relying on changes in localized blood pressure caused by the one or more inflatable members. Tissue alterations themselves may change over time, for example as tissue heals or as scar tissue forms. The site of strain concentrations arising from the embodiment may coincide with the tissue alterations, or may not be coincident with the strain concentration, for instance occurring in a nearby region of the blood vessel 5100.

Figure 52:
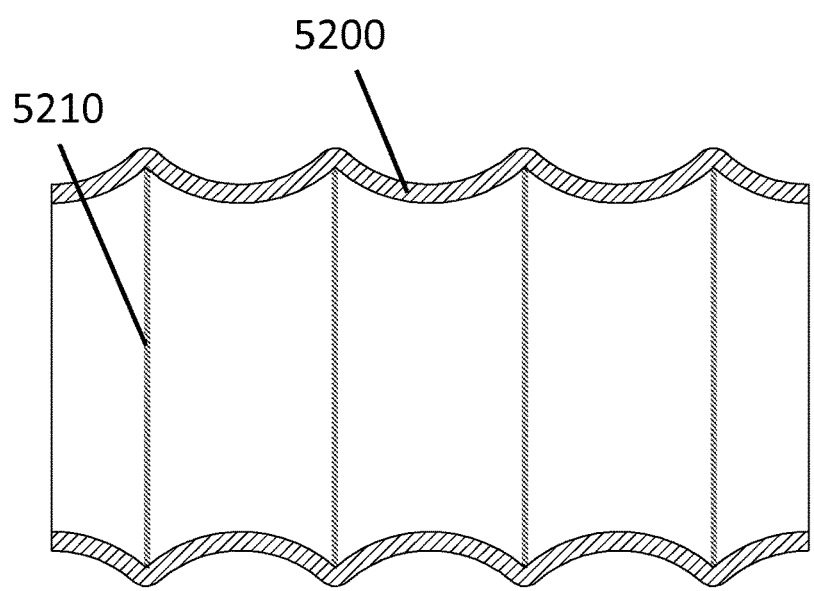
FIG. 52 illustrates a cross section of an altered blood vessel in which stiffness has been decreased along a number of generally circumferential paths.

FIG. 52 shows a cross section of an altered blood vessel 5200 in which stiffness has been decreased along a number of generally circumferential paths 5210. As blood pressure increases during the cardiac cycle, regions of decreased stiffness resist deformation less than untreated regions, creating advantageous changes in baroreceptor activation (compared with an untreated vessel). In some embodiments, baroreceptor activation is more greatly changed at higher blood pressures than at lower blood pressures during the cardiac cycle, and/or minimally changed or not at all changed at lower blood pressures during the cardiac cycle, which may help prevent baroreceptor activation and/or advantageous effects of baroreceptor activation, such as treatment of hypertension, from diminishing over time. In some embodiments, it may be advantageous to alter stiffness (for example, to decrease stiffness) in the blood vessel 5200 when the vessel diameter is similar to that occurring during at least one of the following: (a) diastole, (b) generally low pressure periods of the cardiac cycle, (c) periods of the cardiac cycle at which baroreceptor activation is desirably minimized, in comparison to other periods of the cardiac cycle. In some embodiments, it may be advantageous to alter stiffness in the blood vessel 5200 when the vessel diameter is similar to that occurring during at least one of the following: (a) systole, (b) generally high pressure periods of the cardiac cycle. In some embodiments, a desired vessel diameter is maintained during alteration by providing positive or negative pressure, for example by isolating a region within the blood vessel 5200 (for example, using one or more inflatable members) and injecting or aspirating a fluid and/or relying on changes in localized blood pressure caused by the one or more inflatable members. Tissue alterations themselves may change over time, for example as tissue heals or as scar tissue forms. The site of strain concentrations arising from the embodiment may coincide with the tissue alterations, or may not be coincident with the strain concentration, for instance occurring in a nearby region of the blood vessel 5200.

FIGS. 53, 54, 55, 56, 57, 58, 59, 60, and 61 show flattened views of blood vessel wall segments, onto which example geometric arrangements of alterations are projected.

FIG. 53 illustrates an example embodiment where alterations 5320 on vessel wall segment 5300 extend in two different directions to form a substantially cellular geometric arrangement with the sizes of some cells being smaller than others.

FIG. 54 illustrates an example embodiment of a geometric arrangement of alterations 5420 on vessel wall segment 5400 to form a pattern of alterations including row 5430 and offset row 5440.

FIG. 55 illustrates an example embodiment of a geometric arrangement of circumferential alterations 5520 on vessel wall segment 5500 that are substantially parallel to each other.

FIG. 56 illustrates an example embodiment of a geometric arrangement of circular alterations 5620 on a vessel wall segment 5600.

FIG. 57 illustrates an example embodiment of a geometric arrangement of elongate alterations 5720 running longitudinally on a vessel wall segment 5700.

Figure 58:
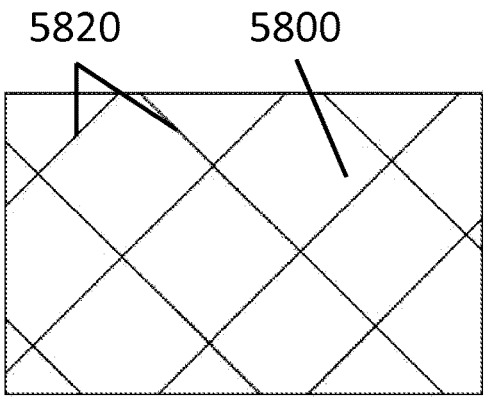

FIG. 58 illustrates an example embodiment of elongate alterations 5820 forming an angled check geometric arrangement along vessel wall segment 5800.

Figure 59:
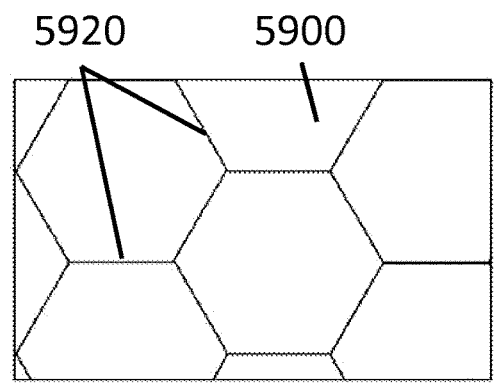

FIG. 59 illustrates an example embodiment of alterations 5920 forming a cellular geometric arrangement on a vessel wall segment 5900.

Figure 60:
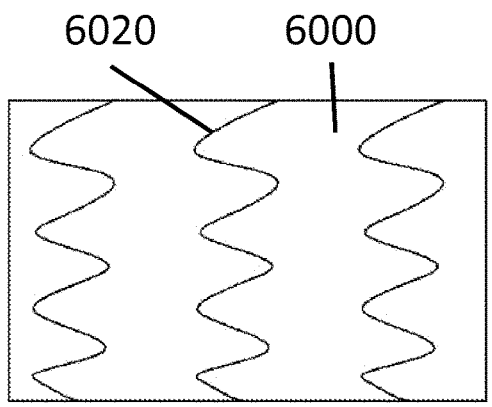

FIG. 60 illustrates an example embodiment of alterations 6020 forming a circumferentially wavy geometric arrangement on a vessel wall segment 6000.

Figure 61:
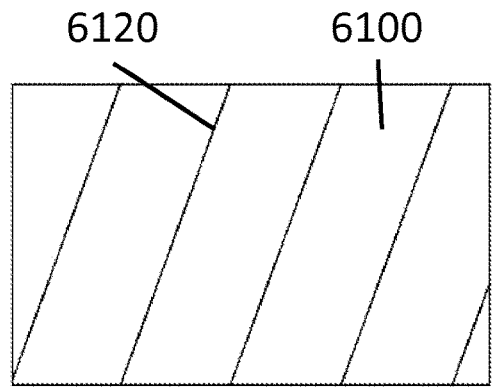

FIG. 61 illustrates an example embodiment of alterations 6120 forming a substantially circumferential angled geometric arrangement on a vessel wall segment 6100.

In some examples, alterations are discreet from one another (for example, alteration 5420 as shown in FIG. 54 and alteration 5620 as shown in FIG. 56), sometimes assuming areas that are approximately circular, sometimes assuming circular areas that are approximately 0.2 mm to approximately 4 mm in diameter. In some examples, alterations assume volumes that are approximately cylindrical, spherical, or hemispherical. In some examples, alterations assume regions or paths that are substantially longer than they are wide; for example one or more paths that are generally parallel to the long axis of the vessel (with same or differing spacing between paths), and/or one or more paths that are generally circumferential (for example, alterations 5520) and/or generally helical and/or generally "zig-zag" shaped; the paths may be approximately evenly spaced or may be unevenly spaced. In some cases, the paths may be between approximately 0.0254 mm (about 0.001 inches) and approximately 1.27 mm (about 0.050 inches) wide. In some examples, alterations assume a grid or cellular geometric arrangement (for example, alterations 5920). In some examples, alterations occupy a non-continuous path. In some examples, alterations occupy a non-closed path. The geometric arrangements herein described may be mixed or matched to achieve a desired overall geometric arrangement of one or more alterations. More generally, alterations of the chemical, biological, and/or mechanical properties of tissues of blood vessels and/or tissues surrounding blood vessels, and/or the structural characteristics of blood vessels and/or surrounding tissues, may assume a geometric arrangement, configuration, location, and/or set of locations described by one or more of the following, which may in some cases contact one another and/or connect one another to assume one or more other geometric arrangement s, configurations, locations, and/or sets of locations: one or more closed paths, one or more open paths, one or more shapes, a cellular geometric arrangement, other arrangements, or combinations thereof.

One or more closed paths may include but are not limited to one or more closed paths, the closed paths each tracing a path that follows the full circumference of a blood vessel; one or more closed paths, the closed paths each tracing a ring around the circumference of a blood vessel; one or more closed paths, the closed paths each tracing a path that corresponds at least one location along the path to all circumferential locations of a blood vessel; one or more closed paths that generally define a circumference of a blood vessel; one or more closed paths, the closed paths each tracing a path that does not include all possible circumferential locations of a blood vessel; one or more closed paths that do not generally define a circumference of a blood vessel; two or more closed paths, each closed path sharing at least part of its path with another closed path; one or more closed paths that traverse through one or more tissues or tissue layers, including but not limited to the intima, media, adventitia, and/or connective tissues; other paths; or combinations thereof.

One or more open paths may include but are not limited to: one or more open paths that each follow a generally helical path relative to the long axis of the blood vessel; two or more open paths that each follow a generally helical path, with at least one helix following a path that is at least partially contained within the axial range of the other helix, the axial range being relative to the long axis of the blood vessel; two or more open paths that each follow a generally helical path, with at least one helix following a path that is not partly or fully contained within the axial range of the other helix, the axial range being relative to the long axis of the blood vessel; one or more open paths that connect one or more closed paths; one or more open path that extend from one or more closed paths; one or more open paths that that trace a path that partially, but not fully, occupies a circumference of a blood vessel; one or more open paths that extend substantially parallel to the long axis of the blood vessel; one or more open paths that traverse through one or more of the following tissues or tissue layers, including but not limited to the intima, media, adventitia, and/or connective tissues; other paths; or combinations of these or other paths.

One or more shapes may include but are not limited to: one or more discrete points; one or more closed paths, the closed path traversing a path that travels the entire circumference of a blood vessel; one or more shapes that traverse through one or more tissues or tissue layers, including but not limited to the intima, media, adventitia, and/or connective tissues; other shapes; or combinations of these or other shapes.

A cellular geometric arrangement may include but is not limited to one or more geometric arrangement that traverses through one or more tissues or tissue layers, including but not limited to the intima, media, adventitia, and/or connective tissues.

Figure 62:
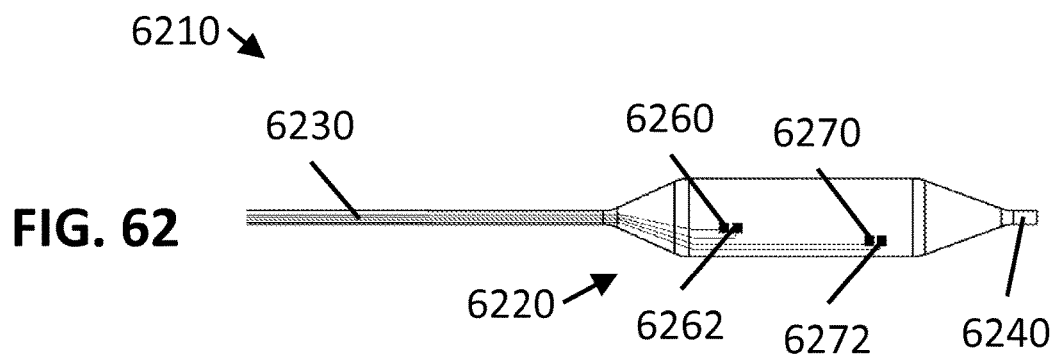
FIGS. 62, 63, and 64 illustrate the distal portion of devices that incorporate an inflatable component to help achieve a desired alteration to tissue.
Figure 63:
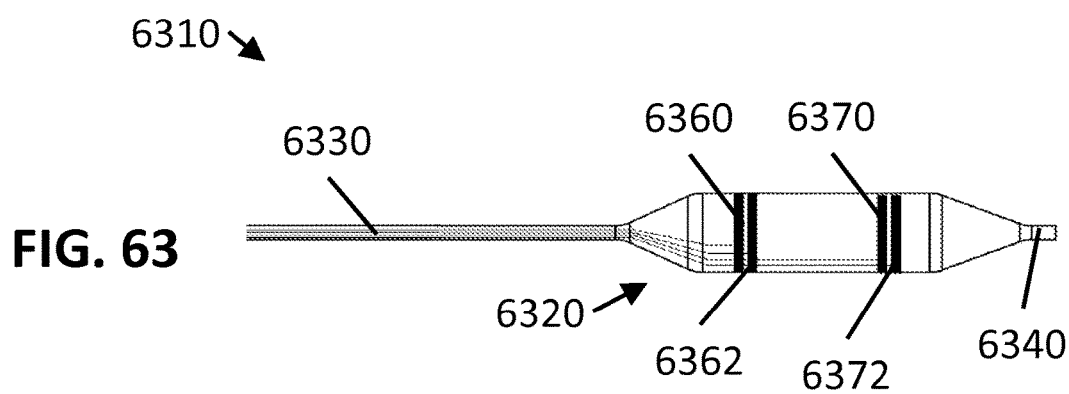
Figure 64:
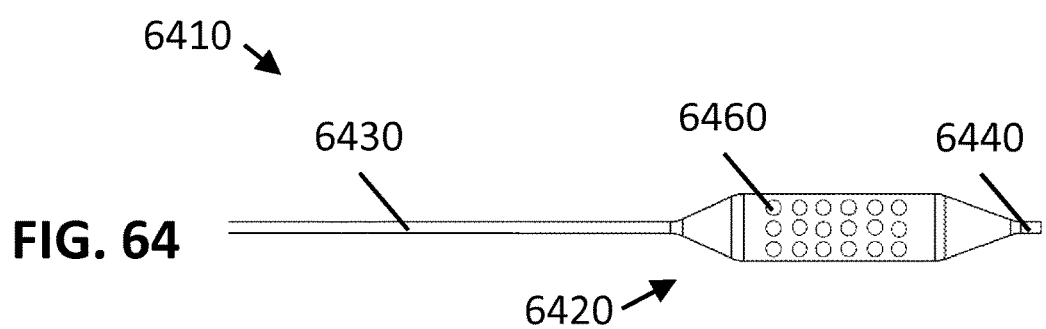

FIGS. 62, 63, and 64 show a distal portion of devices that incorporate an inflatable component to help achieve a desired alteration to tissue. In some cases, the inflatable component helps achieve a desired distance between (a) an energy-delivering and/or energy-withdrawing and/or alteration-focusing element, and (b) a targeted tissue. The inflatable member may be inflated using a fluid, such as saline and/or saline combined with a contrast agent.

FIG. 62 shows a distal portion of a balloon catheter 6210 with electrodes 6260, 6262, 6270, 6272 positioned on a balloon 6220 having a distal tip 6240 and a shaft 6230. The electrodes 6260, 6262, 6270, 6272 are in contact with conductive paths connecting to an energy source proximal to the balloon (as, for example, outside of the body); the electrodes 6260, 6262, 6270, 6272 may act in a monopolar manner, or in a bipolar manner. The electrodes 6260, 6262, 6270, 6272 may be positioned on the outer surface of the balloon 6220 or between the outer surface of the balloon and the inflation fluid. The inflation component may include an electrically insulating layer between the electrodes and the inflation fluid. The electrodes may be configured to provide a variety of different geometric arrangements of alterations in blood vessel tissue and/or surrounding tissue, as described in this document.

FIG. 63 shows a distal portion of a balloon catheter 6310 with electrodes 6360, 6362, 6370, 6372 positioned on a balloon 6320 having a distal tip 6340 and a shaft 6330. The electrodes 6360, 6362, 6370, 6372 may be configured to alter one or more generally circumferential paths; one or more of the circumferential paths may extend the entire circumference of the balloon 6320, or one or more of the circumferential paths may extend only within a partial circumference of the balloon 6320. The electrodes 6360, 6362, 6370, 6372 may act in a monopolar manner, or in a bipolar manner. The electrodes 6360, 6362, 6370, 6372 may be positioned on the outer surface of the balloon 6320 or between the outer surface of the balloon and the inflation fluid. The inflation component may include an electrically insulating layer between the electrodes and the inflation fluid. The electrodes may be configured to provide a variety of different geometric arrangements of alterations in blood vessel tissue and/or surrounding tissue.

FIG. 64 shows a distal portion of a balloon catheter 6410 with ports 6460 on a balloon 6420 having a distal tip 6340 and a shaft 6330. The ports may allow a chemical agent to be released at desired locations to create alterations in a blood vessel and/or its surrounding tissues. Multiple ports 6460 may be utilized, including a porous surface of balloon 6420 that enables delivery of the chemical agent at pressures sufficiently low to avoid unwanted vessel damage.

More generally, it should be understood that the following characteristics may pertain to devices and/or methods to create alterations in a blood vessel and shown, in a subset of possible embodiments, in FIGS. 62, 63, and 64. Balloon catheters 6210, 6310, 6410 may incorporate a balloon 6220, 6320, 6420 and/or other inflatable member, which provides apposition between (a) an electrode, a chemical delivery port, a channel containing a cooled fluid, and/or another therapy-focusing component, and (b) a target tissue. Balloon catheters 6210, 6310, 6410 may incorporate an inflatable member, such as a balloon, which promotes a desired position of an electrode, a chemical delivery port, a channel containing a cooled fluid, and/or another therapy-focusing component, relative to a target tissue. Electrodes and/or conductive paths may be positioned on the surface of the balloon 6220, 6320, 6420 and/or within the surface of the balloon and/or contained within the balloon 6220, 6320, 6420. The balloon catheter 6210, 6310, 6410 may contain a lumen designed to accommodate a guide wire and/or a lumen designed to enable balloon inflation and deflation. The balloon catheter shaft 6230, 6330, 6430 may be made of medical-grade polymers, and/or may be reinforced structurally with a metallic braid, which may be used as a conductive path. The distal tip 6240, 6340, 6440 may be configured to prevent unwanted vessel damage.

Figure 65:
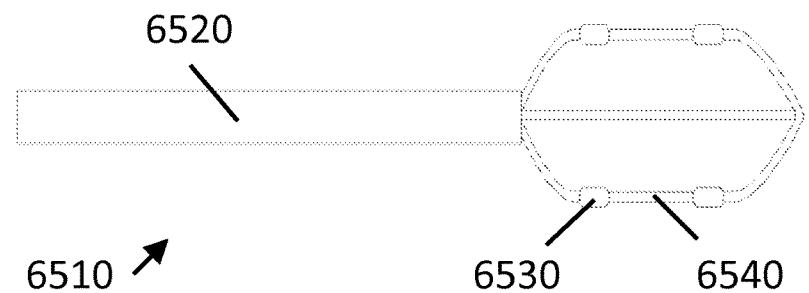
FIG. 65 illustrates the distal portion of an embodiment of a device delivered via a catheter with one or more electrodes positioned on one or more expandable members.

FIG. 65 shows the distal portion of an embodiment of a device 6510 delivered via a catheter 6520 with one or more electrodes 6530 positioned on one or more expandable members 6540). The device utilizes one or more expandable members 6540, which contact a vessel wall and aid in achieving a desired position of one or more electrodes 6530 relative to tissues targeted for alteration. More generally, it should be understood that the following characteristics may pertain to devices and/or methods to create alterations in a vessel and shown, in a possible embodiment, in FIG. 65. Expandable members 6540 may lack electrodes 6530, but provide positional support for other means of tissue alteration, such as by acting as conduits for cooled or heated fluid and/or chemical agents, and/or providing resistive heat. Expandable members 6540 may provide ports for delivery of a chemical agent. Expandable members 6540 may be connected to or integrated with a pusher wire that is advanced through a delivery catheter 3520. Expandable members 6540 may be partially or fully insulated in order to localize tissue alteration. Expandable members 6540 may utilize a shape-memory alloy, such as nickel titanium. Expandable members 6540 may be contained with a sheath and/or inflatable member; the sheath may be open or closed at its ends. The number of expandable members 6540 may range from one to thirty, and the number of electrodes 6530 on each expandable member may range from one to ten. However, in some instances, the numbers of expandable members 6540 and/or electrodes 6530 may deviate from these ranges. Expandable members 6540 may include flexible electronics. Expandable members 6540 may include electrically insulating materials. In some cases, expandable members 6540 may include multiple layers of conductive material separated by insulating material. Expandable members 6540 may culminate in a distal terminus that is configured to be atraumatic to a vessel. Expandable members 6540 may be intertwined when in a collapsed position, as in when constrained within a delivery catheter 6520. One or more non-expandable members 6520 may traverse the generally central axis of the device, to provide structural support and/or electrical conductivity and/or a guide wire lumen.

Figure 66:
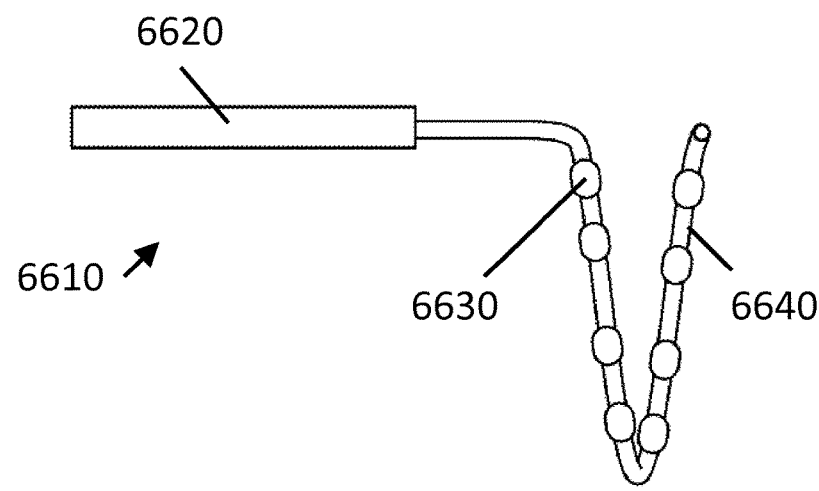
FIG. 66 illustrates the distal portion of an embodiment of a device with one or more electrodes positioned on a region of a device that extends from a catheter.

FIG. 66 illustrates the distal portion of an embodiment of a device 6610 with one or more electrodes positioned on a region of a device 6610 that extends from a catheter 6620. The device 6610 may have eight electrodes 6630, configured to create tissue alterations at a plurality of locations on a vessel wall; the structural member 6640 on which the electrodes 6630 are positioned provides a conductive path to the electrodes 6630, and also promotes apposition of the electrodes against the vessel wall. More generally, it should be understood that the following characteristics may pertain to devices and/or methods that are shown in one embodiment in FIG. 66: The electrodes 6630 may be monopolar, or the device 6610 may rely on a return conductive path integrated into the device 6610 delivered via catheter 6620 and/or a return conductive path integrated into the delivery catheter 6620. The device 6610 may utilize a shape-memory alloy such as nickel titanium.

Figure 67:
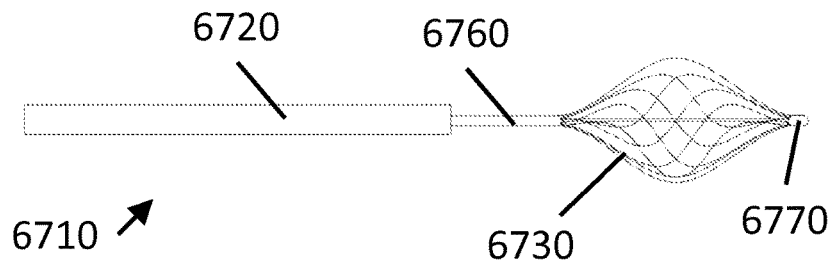
FIG. 67 illustrates the distal portion of an embodiment of a device with one or more electrodes positioned on a region of a device that extends from a catheter.

FIG. 67 shows the distal portion of an embodiment of a device 6710 with one or more electrodes 6730 positioned on a region of a device 6710 that extends from a catheter 6720. The device 6710 may have members 6730 that expand radially when not fully constrained within the catheter 6720. These members 6730 act as electrodes to deliver tissue-altering energy to tissues they contact, and/or tissues in their vicinity. These members 6730 terminate in a distal terminus 6770 that is configured to interact safely with a blood vessel (e.g., to avoid unwanted vessel trauma). These members 6730 are configured to create a desired geometric arrangement of tissue alteration(s). More generally, it should be understood that the following characteristics may pertain to devices 6710 and/or methods that are shown in one embodiment in FIG. 67: Any number of members 6730 may be used. In some embodiments, there may be 1 to 30 members 6730. In some other embodiments, there may be 3 to 8 members 6730. Members 6730 may be comprised in part or full of medical grade metals, including some alloys of nickel titanium and/or stainless steel and/or platinum. Some or all of these members 6730 are configured to create tissue alterations at a plurality of locations on, within, or in proximity to a vessel wall. Part or all of some or all members 6730 may be insulated, which may help isolate alteration effects to desired locations on, within, or in proximity to a vessel wall. Some or all of the distal ends of the members 6730 may converge at a terminus 6770 configured to protect tissues from unwanted damage. Some or all of the distal ends of the members 6730 may be electrically connected to or isolated from one another to facilitate provision of a desired geometric arrangement of tissue alterations. Each member 6730 may have a distinct conductive path to an external power source, or multiple members 6730 may share a common conductive path. Groups of multiple members 6730 may each share one of multiple conductive paths. One or more members 6730 may enable feedback regarding their apposition to a vessel wall, for example based on changes in impedance and/or resistance of an electrical circuit. An operator may vary exposure of the members 6730 by advancing or retracting a catheter 6720 or sheath 6760, which may act to insulate or isolate the members from tissues.

Figure 68:
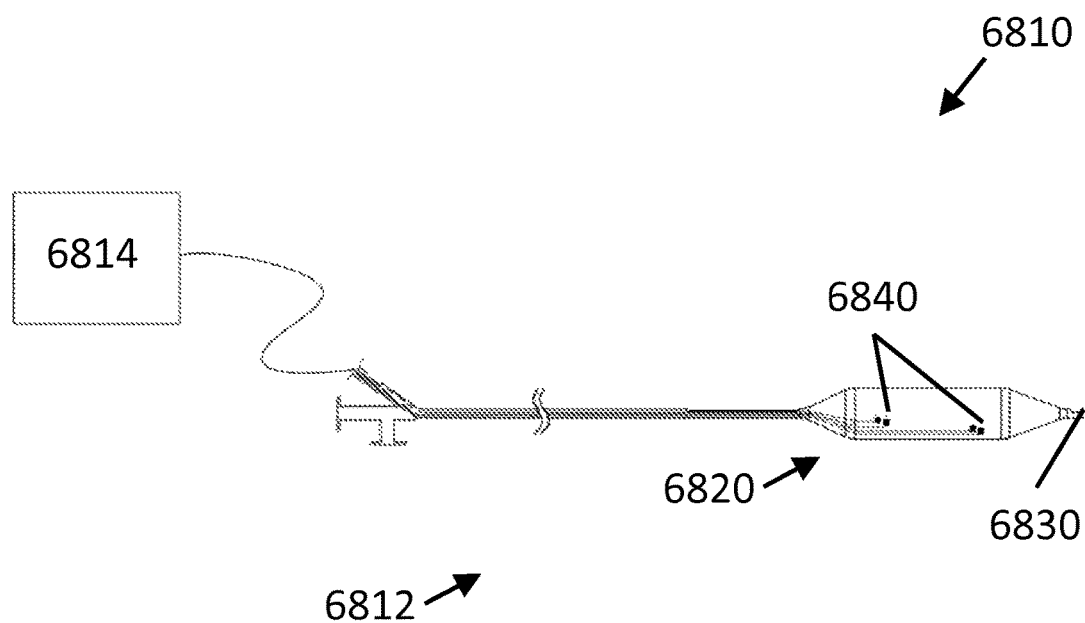
FIGS. 68 and 69 illustrate schematic views of a system for providing radiofrequency energy to body tissues in order to achieve desired tissue alterations.
Figure 69:
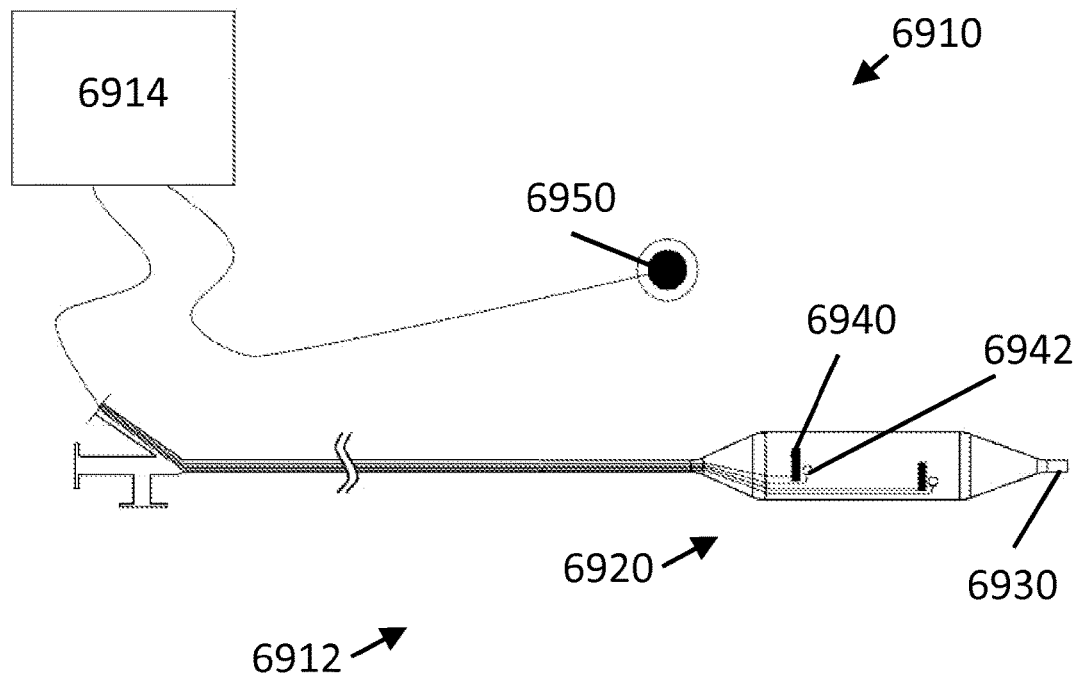

FIGS. 68 and 69 show schematic views of a system for providing radiofrequency energy to body tissues in order to achieve desired tissue alterations. The systems 6810, 6910 of FIGS. 68 and 69 each include a radiofrequency generator 6814, 6914 as well as an intravascular device 6812, 6912 configured to reach the site, or a vicinity of the site, of tissues intended for alteration. The generator 6814, 6914 may include a visual display, and/or an electronic system to adjust parameters of energy application, wherein the adjustment is based on input from the user and/or executed automatically based on an algorithm.

FIG. 68 illustrates an embodiment of a system 6810 having an intravascular device 6812 and generator 6814. Intravascular device 6812 may include inflatable member 6820, bipolar electrodes 6840, distal tip 6830, and various other components.

FIG. 69 illustrates an embodiment of a system 6910, including grounding element 6950, intravascular device 6912, generator 6914, and various other components. Grounding element 6950 may be coupled to a patient. Device 6912 may also feature inflatable member 6920 having distal tip 6930, electrode 6940, and a sensor to measure temperature 6942.

The following characteristics may pertain to systems 6810, 6910 used for tissue alteration described in this document and shown in specific embodiments in FIGS. 68 and 69. Embodiments of tissue alteration systems 6810, 6910 may include a support system and/or generator (such as a radiofrequency energy generator 6814, 6914 for radiofrequency energy, an ultrasound generator for ultrasound energy, or a reservoir of cooled liquid for cooling tissues). The intravascular device 6812, 6912 may be inserted into the vascular system by femoral approach, subclavian approach, insertion into the carotid artery, or by other approaches known or reasonably anticipated to be used in interventional medicine. The intravascular device 6812, 6812 may be integrated with a catheter, or may be passed through a catheter. An introducer sheath and/or guide wire may be used to introduce and/or deliver the intravascular device 6812, 6912. Measures may be taken to protect non-target tissues from undesired alteration, such as providing a cooled fluid to the vicinity of tissue alteration (such as in an inflatable member, such as that shown in FIGS. 68 and 69). Cooled fluid may be pumped from a reservoir through a lumen to an inflatable member, whereby the cooled fluid may cool tissue in the vicinity of the inflatable member. Cooled fluid may be circulated, injected and removed, and/or left in the body. In cases where cryotherapy is used to alter tissue, heat (for example, from heated fluid) may be used to maintain or achieve a desired temperature in tissue not targeted for alteration. In some embodiments, a combination of heat and cryotherapy may be used to achieve or maintain desired temperature in tissue for alteration or prevention thereof. In some embodiments, inflatable members and/or portions of a device that perform tissue alteration have features, or are shaped, to allow at least some blood flow during a tissue alteration procedure. For example, an entry port proximal to, or on the generally proximal side of, an inflatable member may allow blood to pass to an exit port distal to, or on the generally distal side of, the inflatable member 6820, 6920, for example via a tube or channel connecting the proximal and distal ports. In some embodiments, devices or features to prevent emboli are positioned proximal or distal to the tissue alteration device or feature. For example, a blood-permeable filter may be placed in the internal carotid artery distal to the location at which a radiofrequency-based tissue alteration device delivers energy.

Figure 70:
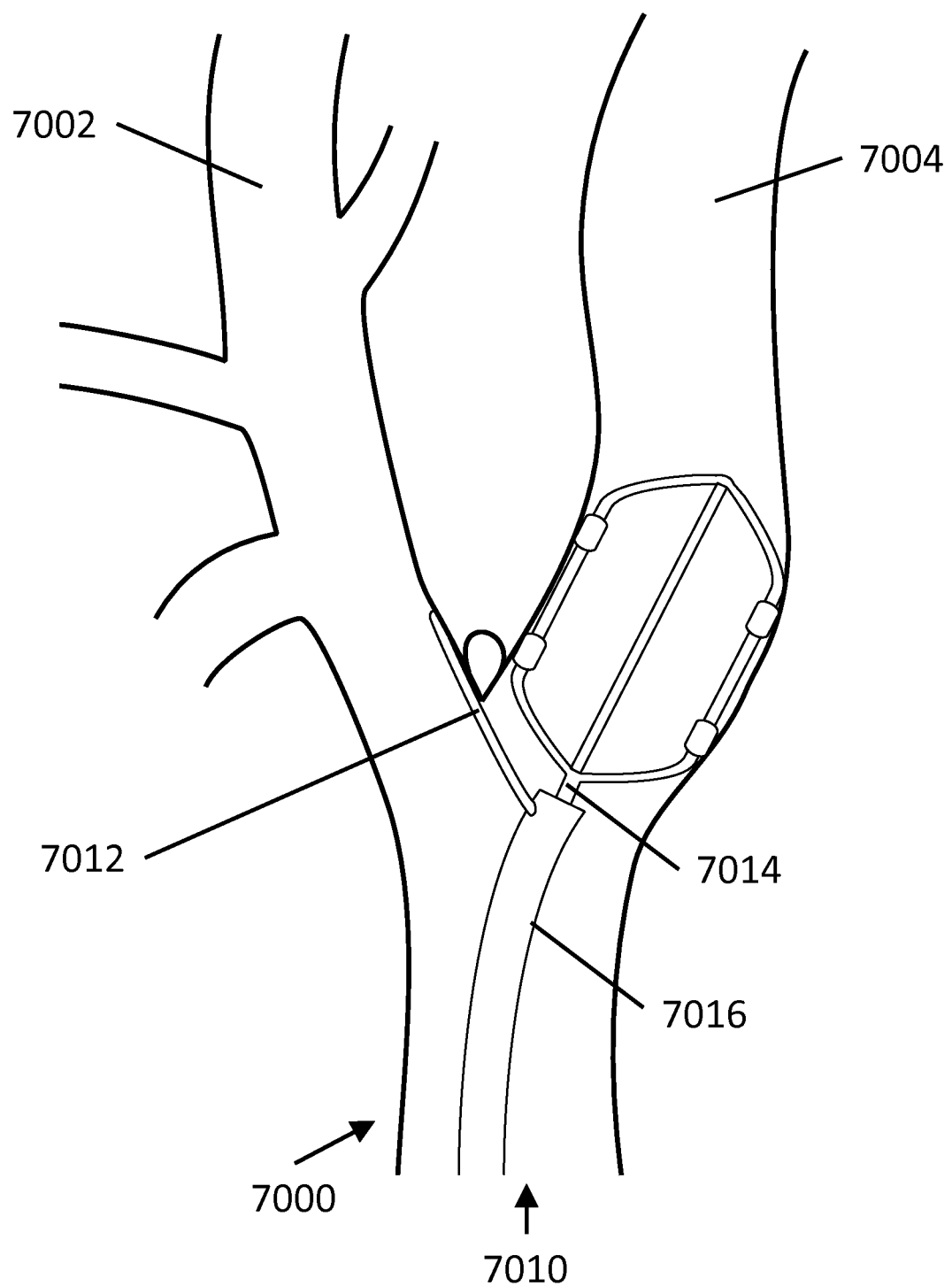
FIG. 70 illustrates a device and method that helps an operator desirably orient a delivery device, an implant, and/or a vessel treatment or alteration device.

FIG. 70 illustrates a device 7010 within the anatomy of the blood vessels near the bifurcation of the common carotid artery 7000 including the internal carotid artery 7004 and the external carotid artery 7002. Also illustrated is a method that helps an operator desirably orient a delivery device, an implant, and/or a vessel treatment or alteration device. In some embodiments, a first member 7012 extends at least partially into an external carotid artery 7002, while a second member 7014 extends at least partially into an internal carotid artery 7014. The relative orientation of the first and second members 7012, 7014 (constrained at least partially by the arteries 7002, 7004 into which they extend) helps an operator achieve a desired orientation between at least one of the members 7012, 7014 and a specific circumferential site or region of an artery (for example, the medial wall of the internal carotid artery). The first member 7012 and the second member 7014 may be advanced, retracted, and/or rotated by an operator relative to an elongate member 7016. In at least some embodiments, the position of the elongate member 7016 and/or the second member 7014 may be adjusted along a direction that generally follows the long axis of the internal carotid artery. In at least some embodiments, the elongate member 7016 and/or the second member 7014 may also or alternatively be rotated within the internal carotid artery 7004. Axial and/or rotational adjustments may help achieve a desired orientation of the delivery, the implant, and/or the vessel treatment or alteration device relative to a known or suspected region of baroreceptor concentration. Additional device features may help an operator achieve a desired placement, including one or more of the following: radio-opaque markers on a delivery device, an implant, and/or a vessel treatment or alteration device; markers on portions of a device outside the human body whose relative locations correspond to relative locations of portions of device(s) inside the human body; mechanical interferences that promote or help identify (such as by providing tactical feedback) desired axial or rotational position of the second member relative to the first member, the internal carotid artery 7004, the external carotid artery 7002, the carotid bifurcation, and/or a known or suspected region of baroreceptor concentration, or which restrict axial or rotational position to a desired position, such as one that directs a tissue alteration treatment toward a targeted region, protects untargeted tissues from alteration, and/or orients an implant to desirably impart stress on a vessel. In some embodiments, the device 7010 has one or more inflatable members that partly or fully occlude blood flow. In some embodiments, the first member 7012 and/or the second member 7014 engage with the carotid bifurcation.

Figure 71:
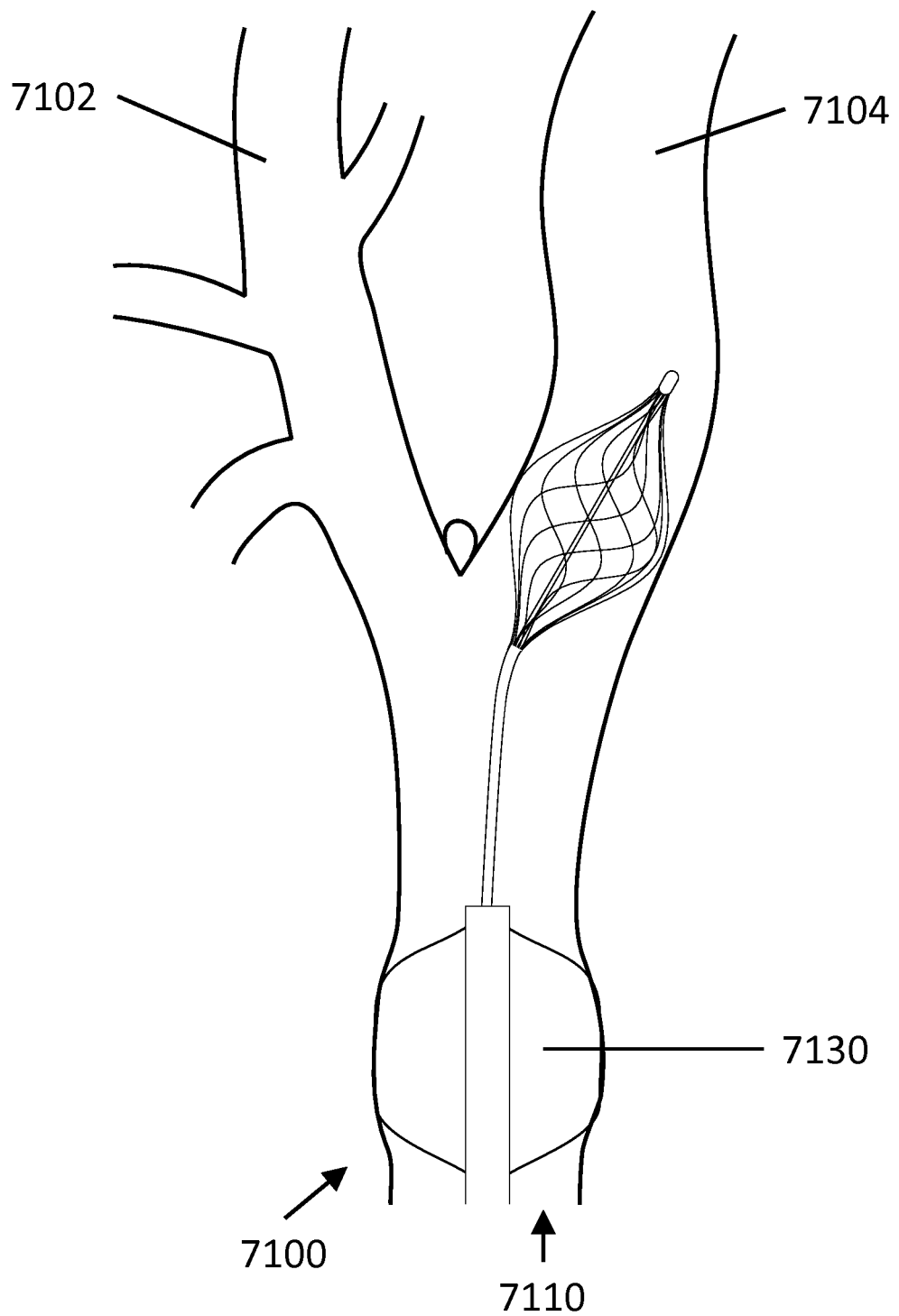
FIG. 71 illustrates an embodiment of a device or method that promotes engagement of a tissue-altering device with a vessel wall at a desired state of vessel dilation, such as one corresponding to a particular stage of the cardiac cycle.

FIG. 71 illustrates a device 7110 within the anatomy of the blood vessels near the bifurcation of the common carotid artery 7100 including the internal carotid artery 7104 and the external carotid artery 7102. Also illustrated is a method that promotes engagement of a tissue-altering device 7110 with a vessel wall at a desired state of vessel dilation, such as one corresponding to a particular stage of the cardiac cycle. In some embodiments, a vessel is partially or fully occluded, temporarily, upstream of the site targeted for tissue alteration or for an implant. The upstream occlusion may cause blood pressure at the targeted site to remain lower during at least part of the cardiac cycle than it would be at the site without the upstream occlusion. In some embodiments, tissue alteration is deliberately performed at this lower blood pressure. In some embodiments, performing tissue alteration at this lower blood pressure causes distortions in vessel wall strain to disproportionately occur at higher blood pressures during the cardiac cycle after upstream occlusion is discontinued. In other embodiments, a vessel is partially or fully occluded, temporarily, downstream of the site targeted for tissue alteration or for an implant. The downstream occlusion may cause blood pressure at the targeted site to remain higher during at least part of the cardiac cycle than it would be at the site without the downstream occlusion. In some embodiments, tissue alteration is deliberately performed at this higher blood pressure. In some embodiments, performing tissue alteration at this higher blood pressure causes distortions in vessel wall strain to disproportionately occur at lower blood pressures during the cardiac cycle after downstream occlusion is discontinued. In some embodiments, full or partial occlusions are positioned both upstream and downstream of a site targeted for vessel alteration and/or device implantation, and pressure in the region between the occlusions is manipulated, such as by injection or aspiration of fluid, to achieve a desired vessel dilation. In some cases, the desired vessel dilation corresponds to a dilation achieved during the cardiac cycle. Methods, devices and device components used to achieve partial or full occlusions may include inflatable balloons 7130, and/or augmentations on the delivery device 7110. In some embodiments, suction is used to pull a blood vessel against a tissue alteration device, for example to perform tissue alteration at a diameter corresponding to a particular phase (for example, diastole) of the cardiac cycle.

Figure 72:
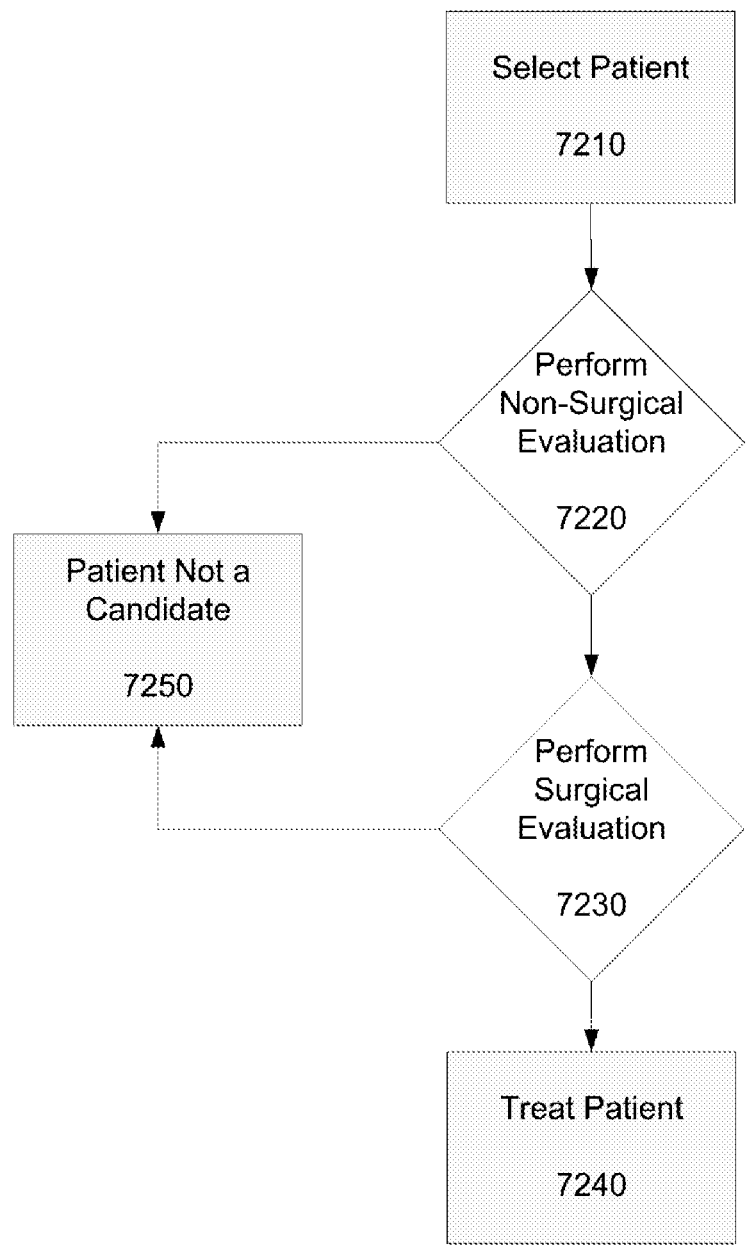
FIG. 72 illustrates a decision flow diagram that may be used to assess whether to treat a patient with one or more of the embodiments described herein. In some cases, according to additional exclusion criteria or medical circumstances not explicitly listed on the flow diagram, a patient may not be treated.

FIG. 72 shows a decision flow diagram that may be used to assess whether to treat a patient with one or more of the embodiments described herein. In some cases, according to additional exclusion criteria or medical circumstances not explicitly listed on the flow diagram, a patient may not be treated.

Step 7210 includes selecting a patient with hypertension or other baroreceptor-regulated condition. Step 7220 includes performing a non-surgical evaluation on the patient to determine the impact of baroreflex stimulation on the baroreceptor-regulated condition. In a non-limiting example, the non-surgical evaluation may comprise non-invasive application of vacuum, vibration, or ultrasound to tissue in the vicinity of baroreceptors. If the evaluation indicates that baroreflex stimulation would favorably impact the patient, then step 7230 may be performed; otherwise, it may necessary to move to step 7250. Step 7250 indicates labeling the patient as not a candidate for a particular treatment. Step 7230 involves performing a reversible surgical procedure to determine the impact of tissue alteration or device implantation on the baroreceptor regulated condition. If the impact justifies tissue alteration or device implantation, then it may be advisable to perform step 7240. Otherwise, it may be necessary to go to step 7250 and label the patient as not a candidate for a particular treatment.

Devices and methods for pre-operatively, peri-operatively, or post-operatively assessing, measuring, or predicting the impact of the described methods and devices on the patient's condition (including blood pressure) may include: assessing whether the morphology of pertinent anatomical features are amenable to the intervention; measuring baroreflex sensitivity; determining peripheral and central components of baroreflex sensitivity; assessing sympathetic nerve activity and/or renal sympathetic nerve activity; measuring carotid stenosis; determining of the presence of ulcerative plaques in the carotid artery and/or other vessels; evaluating a patient for orthostatic hypotension; in hypertensive patients, determining the type of hypertension (including essential hypertension and secondary hypertension); determining and/or considering whether a patient is taking anti-hypertensive medication, and which anti-hypertensive medication(s) are being taken; determining carotid artery distensibility; measuring oxidative stress; stimulating the receptors of the carotid sinus and measuring and/or assessing sympathetic nerve activity, muscle sympathetic nerve activity, renal sympathetic nerve activity, blood pressure, blood flow, heart rate, heart failure, respiration rate, and/or whether adaptation to the stimulation has occurred or will occur, whether acutely or chronically, wherein the stimulation may be applied over a period of seconds, hours, days, or weeks, with or without the use of a data logging system; and/or measuring sympathetic tone. Methods or devices for providing the stimulation may include, but are not limited to: electrical stimulation, vacuum applied to the head or neck, vibration or ultrasound applied externally or endovascularly, thermal energy, deployment of an intravascular device, inflation of an intravascular balloon, and/or other means of mechanical stimulation.

Devices and methods used to peri-operatively assess or optimize effectiveness of therapy include but are not limited to: an endovascular and/or extravascular device that locally stimulates the wall of the carotid sinus, the stimulation resulting from one or more of mechanical contact with the vessel wall, vibration, ultrasound, thermal energy, and electrical stimulation; devices and methods that allow reversible and/or repositionable deployment of an endovascular device that locally stimulates the wall of the carotid sinus by means including those described in this document (including, but not limited to, a stent-like device and/or an inflatable balloon); devices and methods that enable mapping of optimal location for treatment (such as device implantation and/or tissue modification); devices and methods that measure carotid sinus nerve afferent activity, sympathetic nerve activity, vagal nerve activity, muscle sympathetic nerve activity, renal sympathetic nerve activity, blood pressure, blood flow, heart rate, respiration rate or other physiological measures.

Devices and methods may be used to determine the appropriate size and/or length of therapeutic device and/or implant to be used, utilizing fluoroscopic and/or radiographic imaging, ultrasound, or other techniques.

Figure 73:
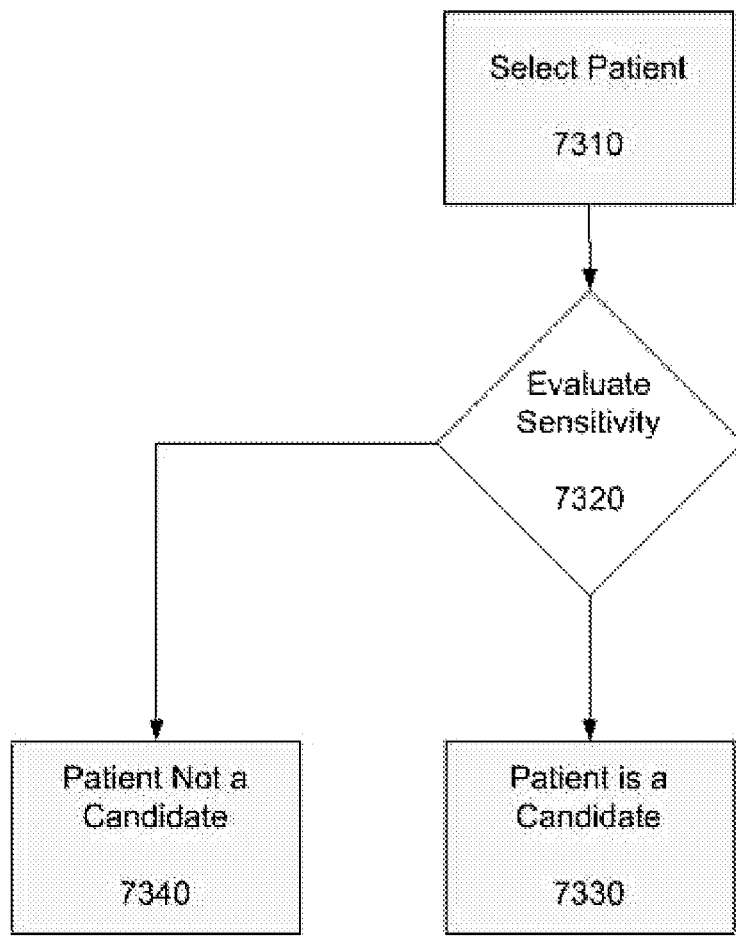
FIG. 73 illustrates a decision flow diagram that may be used to assess whether to treat a patient with one or more of the embodiments described herein. In some cases, according to additional exclusion criteria or medical circumstances not explicitly listed on the flow diagram, a patient may not be treated.

FIG. 73 shows a decision flow diagram that may be used to assess whether to treat a patient with one or more of the embodiments described herein. The process may begin with step 7310, selecting a patient with hypertension or another baroreceptor-regulated condition. Next, the central component of the patient's baroreflex sensitivity may be evaluated in step 7320. If the sensitivity is above a predetermined threshold, then the patient may be labeled a candidate in step 7330. If the sensitivity is below a predetermined threshold, then the patient may be labeled as not a candidate in step 7340. In some cases, according to additional exclusion criteria or medical circumstances not explicitly listed on the flow diagram, a patient may not be treated. In a non-limiting example, the non-surgical evaluation to determine the impact of baroreflex stimulation on the baroreceptor-regulated condition may comprise non-invasive application of vacuum, vibration, or ultrasound to tissue in the vicinity of baroreceptors.

The devices, methods, and systems shown and discussed above and in FIGS. 1-73 may be used in various combinations. Various additional devices, methods, and systems that incorporate and utilize those discussed above are described below.

Devices and methods described in this document may be utilized either unilaterally (e.g., on a side determined to be advantageous over the other side) or bilaterally (on both carotid sinuses).

Devices and methods may be employed that concentrate the effects described in this document at sites where stretch receptors are concentrated. In particular, the effects may be concentrated in the proximal internal carotid artery (for example, on the proximal-most one centimeter of the internal carotid artery) and/or in the medial wall of the internal carotid artery and/or in the side of the internal carotid artery originating in the crotch of the common carotid artery bifurcation and/or facing the external carotid artery. Additionally or alternatively, devices and methods may be employed that concentrate the effects described in this document on particular layer(s) in the blood vessel wall, including, for example, the adventitial layer.

One or more vessels associated with or comprising the carotid sinus may be subjected to a force created by an intravascularly-delivered device (which may be self-expanding or expanded by an inflatable balloon) and/or an extravascularly-delivered device, which may be geometrically constrained in a manner that preserves a desired position relative to the blood vessels.

Devices and methods may be employed to change the strain in the vessel wall(s) at the site of the receptors that occurs during the cardiac cycle. In particular, some or all of the strains occurring during the cardiac cycle may be altered. The changes in strain may arise from changes in blood pressure and/or localized blood flow. For example, devices and methods may be employed to shift the strains occurring throughout the cardiac cycle in one or more of the following manners: strains at all blood pressures occurring within the cardiac cycle are increased; strains at higher blood pressures occurring within the cardiac cycle are increased more (in absolute increase, by percentage increase, or both), than strains at lower blood pressures occurring within the cardiac cycle are increased; strains at lower blood pressures occurring within the cardiac cycle are increased more (in absolute increase, by percentage increase, or both), than strains at higher blood pressures occurring within the cardiac cycle are increased; strains at higher blood pressures occurring within the cardiac cycle are increased, while strains at lower blood pressures occurring within the cardiac cycle are unchanged or minimally increased or minimally decreased or changed by a lesser amount than strains at the higher blood pressures are changed; strains at lower blood pressures occurring within the cardiac cycle are increased, while strains at higher blood pressures occurring within the cardiac cycle are unchanged or minimally increased or minimally decreased or changed by a lesser amount than strains at the lower blood pressures are changed; or strains at lower blood pressures occurring within the cardiac cycle are decreased, while strains at higher blood pressures occurring within the cardiac cycle are unchanged or minimally increased or minimally decreased or changed by a lesser amount than strains at the lower blood pressures are changed.

The magnitudes of forces on one or more blood vessels associated with or comprising the carotid sinus may be purposefully localized, increased, or decreased using augmentations or recesses on the device, or other geometric configurations or features intended to distribute forces in an advantageous manner. In particular, forces may be concentrated in order to preferentially stretch receptors in the vessel wall at desired magnitudes and desired times in the cardiac cycle (where the cardiac cycle is understood to represent the period of time between a first and subsequent heart beat, and the range of blood pressures and blood flow rates occurring during the period). Relative to the normal configuration of the blood vessels, the receptors may be stretched circumferentially, or longitudinally, or a combination of circumferentially and longitudinally.

Devices and methods may be used which amplify the difference in strain in the wall of the carotid sinus that naturally occurs as blood pressure increases from diastolic pressure to systolic pressure (and activates stretch receptors in the vessel wall). For example, the following devices and methods may be used: substantially intravascular or substantially extravascular devices that assume a lower radius of curvature as blood pressure increases; substantially intravascular or substantially extravascular devices that impart minimal force on the vessel when blood pressure is at or near diastolic pressure, but considerable force on the vessel as blood pressure increases toward systolic pressure, thus activating the strain receptors directly or changing the shape of the vessel in a manner that increases strain receptor activation stemming from blood pressure; or substantially intravascular or substantially extravascular devices that provide decreasing resistance to radial expansion with increasing radial expansion of the blood vessel, including but not limited to devices that provide negative resistance to radial expansion with radial expansion of the blood vessel. In one example, devices and methods may be used that exhibit a higher strain or deformation in one or more sections of the device when a lower strain or deformation is created in one or more other sections of the device, thereby altering the relationship between blood pressure and strain in the vessel wall. In another example, devices may exhibit a strain or deformation in one or more sections of the device or directions when a strain is created in another one or more sections of the device or another direction. In another example, an intravascular implant features a strut geometry that promotes longitudinal elongation of the intravascular implant when the implant is radially expanded as a result of blood pressure.

Devices and methods that impart a force on a vessel wall—whether from inside the vessel wall, outside the vessel wall, or from within the vessel wall itself—may feature an implant with a particularly high or low unstressed radius of curvature in region(s) that interface with the vessel, such that the ratio of the range of force over the course of a cardiac cycle imparted by the implant to the vessel wall, to the mean force over the course of a cardiac cycle imparted by the implant to the vessel wall, is minimized and/or smaller than the ratio occurring with an implant with a less particularly high or low unstressed radius of curvature.

Devices and methods may be employed to change the strain in the vessel wall(s) at the site of the receptors that occurs during the cardiac cycle that utilize a device delivered using an intravascular catheter, the device engaging the vessel wall and (a) pulling one or more locations of the vessel wall radially inward, and/or (b) pushing or pulling one or more locations of the vessel wall in a direction generally parallel to the long axis of the vessel. Methods of engagement may include, but are not limited to, one or more of the following: suction, a mechanical anchor (including anchors that pass partly or fully through the vessel wall), an adhesive, an implantable structure that becomes anchored in the vessel wall due to a biological response to its implantation, and/or an implantable structure that becomes anchored in the vessel wall due to a biological response to its implantation and upon resorption, dissolution, or degradation of part of the structure imparts a force radially-inward and/or generally parallel to the long axis of the vessel, at least one location in the vessel wall.

Devices and methods may be used which alter the shape and/or curvature of the internal carotid artery in the region including the carotid sinus, in order to locally increase forces on the vessel wall arising from blood flow or blood pressure, in order to achieve greater activation of stretch receptors in the vessel wall. The devices may be positioned inside the blood vessel or outside the blood vessel, or a combination of the two. In one example, an endovascular implant is placed within the vicinity of the carotid sinus, such as in the internal carotid artery, which promotes a more curved vessel shape, causing an increase in strain in the vessel wall resulting from altered blood flow. In another example, an extravascular implant is placed within the vicinity of the carotid sinus, such as on the exterior of the internal carotid artery, which promotes a more curved vessel shape, causing an increase in strain in the vessel wall resulting from altered blood flow. In another example, an endovascular or extravascular implant is used to generally change the geometry of the transition between the common carotid artery and the internal carotid artery, such that the angle between the common carotid artery and the internal carotid artery is decreased.

Devices and methods may be used that utilize a partially resorbable, degradable, dissolvable, and/or absorbable structure, which assumes a first position in a blood vessel or body lumen according to residual mechanical forces and/or biological responses; then, upon resorption, degradation, dissolution, and/or absorption of part of the device's structure, provides an advantageous force or pressure profile on surrounding tissues. The resorbed, degraded, dissolved, or absorbed part of the device may advantageously deliver anti-inflammatory agents or other drugs, and may be constructed of a polymer. The remaining part of the device may be constructed of biocompatible metal and/or polymer. The remaining part of the device may feature geometric features, surface roughness, and/or surface treatments that prevent migration of the residual structure relative to directly surrounding tissues, or even promote tissue ingrowth into features of the device, which may prevent migration of the residual device structure. In one example, an implantable vascular device is configured to provide longitudinal force on a region of a vessel after one or more resorbable, degradable, dissolvable, and/or absorbable portions of the device's structure come to un-constrain portions of the device providing longitudinal force.

Devices and methods may be used which achieve stress or strain concentrations in the vessel wall that are commonly associated with the longitudinal ends of vascular implants such as stents. The stresses or strains may be used to advantageously activate strain receptors in the vessel wall. The stresses or strains may be achieved at locations in the vessel wall that correspond to the longitudinal ends of the device, and/or other locations near elements in the device that are configured to impart forces on the vessel wall similar to those imparted by the longitudinal ends of vascular implants such as stents, in order to achieve desired stresses and strains in the vessel wall. In one example, a vascular implant has intermediate longitudinal regions possessing geometry similar to the end of a stent, and the vascular implant is positioned within the vessel such that the regions are located near areas of concentrated stretch receptors in the vessel wall. In another example, a vascular implant has at least two regions that create circumferential strain on a vessel, and the at least two regions are positioned such that a region of concentrated strain receptors in the vessel wall is positioned between the at least two regions of the vascular implant creating circumferential strain on the vessel. The devices and methods discussed in this document may also be used to activate stretch receptors in the wall of the aortic arch, and or stretch receptors in other vessels. Electrical stimulation of the aortic arch depressor nerve and/or aortic arch stretch receptor afferents may be utilized.

Devices and methods may be used which promote a generally non-circular (for example, oval) cross-section of a vessel, using an intravascular or extravascular implant that has a generally non-circular cross section when observed in a free and unloaded state, and/or upon implantation.

Devices and methods may be used which provide an implant with a cross-section that varies in area, size, and/or shape along its longitudinal axis. For example, devices and methods may be used which provide an implant that promotes, maintains, or allows a circular vessel cross-section along the region of the vessel corresponding to the implant, with the area of the circular vessel cross-section varying in that region, with such variations providing advantageous stress or strain concentrations.

Devices and methods may be used that apply vacuum to the head and/or neck to stimulate stretch receptors in the vessel wall of the carotid sinus. The vacuum may be applied in a pulsatile manner, for example, in sync with, at a rate faster than, or at a rate lower than the patient's pulse rate.

Devices and methods may be used that electrically stimulate the stretch receptors in the vessel wall. Devices may be delivered and/or positioned extravascularly, and/or delivered and/or positioned intravascularly. For example, an intravascular implant with an integrated, externally-powerable energy storage element may be positioned near or within a region of the carotid sinus, anchored using radial force, and used to electrically activate stretch receptors. The stimulation may occur continuously, or at a frequency in sync with, faster than, or slower than the patient's pulse rate. The device may also respond to a detected blood pressure and/or pulse rate. The device may be an intravascular implant that also provides treatment for carotid stenosis, for example, in the same manner as a carotid stent. The device may provide less stimulation (by magnitude, frequency, or both) at night than during the day.

Devices and methods may be used which use elastase, collagenase, or other chemical agents to alter, either temporarily or permanently, the elasticity of a region of a vessel, changing the strain that occurs at the site of receptors through part or all of the blood pressure range encountered. The chemical agents may be delivered by catheter injection, and/or through an inflated intravascular balloon, and/or by elution from an implanted device, and/or by direct application during surgery. The chemical agents may be delivered in combination with carotid stenting and/or carotid endarterectomy.

Devices and methods may be used which heat or cool a region of a vessel, changing the strain that occurs at the site of receptors through part or all of the blood pressure range encountered.

Devices and methods may be used which involve the cutting of a portion of the vessel, including but not limited to the internal wall of a vessel, in order to increase the effective circumferential and/or longitudinal strain occurring at stretch receptors in the vessel wall.

Devices and methods may be used that combine conventional functionality of carotid artery stents with an ability to favorably activate stretch receptors in blood vessel walls of the carotid sinus, as through (but not limited to) devices and methods described in this document.

Devices and methods may be used that utilize tape, a stretchable adhesive, and/or suture to favorably activate stretch receptors in the carotid sinus wall. Such devices and methods may utilize the tape, stretchable adhesive and/or suture to maintain strain in a region of a vessel wall.

Devices and methods may be used that feature endovascular implants with one or more of the following: an adjustable length, drug elution to minimize hyperplasia and/or promote re-endothelialization, a geometry that promotes resistance to fracture and fatigue, deliverability via catheter, ability to self-expand, and/or balloon expandability.

Devices and methods may be used that reduce the activation level of the carotid body. These devices and methods may function through: destructing, damaging, lesioning, compromising, or partly or fully removing the carotid body using ablation, surgical resection, embolization, clipping, injection of a chemical agent, restricting blood supply to the carotid body, constriction of the carotid body or the vessels providing its blood supply with a filament (such as suture), or other methods. The devices and methods may be utilized in conjunction with devices and methods which advantageously activate the stretch receptors of the carotid sinus. For example, an endovascular method may be used that utilizes the same access point, and/or same access catheter system, and/or same guide wire to deliver therapy to regulate and/or activate the stretch receptors of the carotid sinus as well as to deliver therapy to regulate and/or partially or fully deactivate the carotid body. In another example, an extravascular method may be used that utilizes the same access point and/or instruments and/or navigation and/or visualization means to deliver therapy to regulate and/or activate the stretch receptors of the carotid sinus as well as to deliver therapy to regulate and/or partially or fully deactivate the carotid body.

Devices may be used which are comprised of biocompatible metals (including, but not limited to, medical-grade formulations of platinum, stainless steel, cobalt, titanium, Nitinol, and/or cobalt-chromium, and/or alloys containing these metals) and/or biocompatible polymers. Devices described herein may be supplemented with radio-opaque markers or components.

Devices and methods may be employed that produce arterial contact by an implantable device by three or more members of the device, the device constructed to increase the radius of curvature of the arterial wall at a first set of three or more arterial wall regions at a given longitudinal location, while allowing the first set of arterial wall regions to pulsate at the longitudinal location, with the aforementioned three or more artery contacting members contacting a second set of at least three regions of the arterial wall (but not contacting the aforementioned first set of arterial wall regions), wherein the first set of regions and the second set of regions are not arranged in an alternating manner.

Devices and methods may be employed that feature a device with three or more longitudinal regions, separated from other longitudinal regions at a given longitudinal location by one or both of (a) one or more of a first kind of absence of device material, where there is no contact between the device and the vessel wall, and the radius of curvature of the vessel wall is increased, and/or (b) one or more of a second kind of absence of device material, where there is no contact between the device and the vessel wall, and the radius of curvature of the vessel wall is not increased. At any given longitudinal location, any combination and/or sequence of the longitudinal regions of the device and the two kinds of absences may be encountered along the circumference of the device. In some cases, the second kind of absences are holes, cuts, slots, slits, grooves, notches, and/or troughs which pass partly or fully through a thickness of metal or polymer.

Devices and methods may be employed that feature a device with three or more longitudinal regions, separated from other longitudinal regions at a given longitudinal location by one or both of (a) one or more of a first kind of absence of device material, where there is no contact between the device and the vessel wall, and the vessel wall at the absence is allowed to stretch and contract during the cardiac cycle, and/or (b) one or more of a second kind of absence of device material, where there is no contact between the device and the vessel wall, and the vessel wall at the absence is restricted from stretching and contracting during the cardiac cycle. At any given longitudinal location, any combination and/or sequence of the longitudinal regions of the device and the two kinds of absences may be encountered along the circumference of the device. In some cases, the second kind of absences are holes, cuts, slots, slits, grooves, notches, and/or troughs which pass partly or fully through a thickness of metal or polymer.

Devices and methods may be employed that feature a device with three or more regions or members, which extend longitudinally relative to the main axis of the blood vessel along paths that may occupy varying positions along the circumference of the blood vessel. In some cases, two or more of the regions or members may be configured to be of equal distance from first and second adjacent regions or members. In some cases, two or more of the regions or members may be configured to assume non-parallel paths. In some cases, two or more of the regions may be of substantially equal length.

Devices and methods may be employed that feature two or more members of substantially similar length and/or stiffness connecting to a common member, thereby connecting regions of a first kind that provide substantial circumferential coverage of and/or radial force on a vessel, interspersed longitudinally (relative to the long axis of the vessel) with regions of a second kind that provide considerably less circumferential coverage of and/or radial force on the vessel. The connection may facilitate resheathing the device.

Devices and methods may be employed that feature a device with regions of a first kind that provide substantial circumferential coverage of and/or radial force on a vessel, interspersed longitudinally (relative to the long axis of the vessel) with regions of a second kind that provide considerably less circumferential coverage of and/or radial force on the vessel. In some cases, substantial circumferential coverage and/or radial force may be exemplified and/or provided by small average gaps between structural members at given longitudinal locations, and/or small maximum gaps between structural members at given longitudinal locations, and/or a higher quantity of structural members at given longitudinal locations, and/or structural members that are materially and/or geometrically stiffer at given longitudinal locations, while considerably less circumferential coverage and/or radial force may be exemplified and/or provided by large average gaps between structural members at given longitudinal locations, and/or large maximum gaps between structural members at given longitudinal locations, and/or a lower quantity of structural members at given longitudinal locations, and/or structural members that are materially and/or geometrically less stiff at given longitudinal locations. In some cases, regions of the first kind and regions of the second kind may be separated to achieve stress concentrations in the vessel wall, in some cases similar to those sometimes caused by the ends of vascular stents, at one or both ends of the subject device, and/or at one or more sites between the ends of the subject device. In some cases, regions of the first kind feature members that travel back and forth axially along a generally circumferential path, while regions of the second kind feature one or more members that provide mechanical connection (in some cases, substantially longitudinal connection) between regions of the first kind. In some cases, the radial force provided by regions of the first kind and/or the axial length of regions of the second kind are selected to advantageously activate stretch receptors in the blood vessel wall. In some cases, the device may be aligned to activate regions of blood vessels with a high concentration of stretch receptors, such as the proximal-most 1 cm of the internal carotid artery.

Devices and/or methods may be employed that feature a self-expanding implantable device that is unsheathed intravascularly to achieve deployment. In some cases, the implantable device utilizes a sheath to constrain the self-expanding implantable device. In some cases, the implantable device and sheath are configured such that movement of the sheath in a particular direction causes the sheath to only encounter a continuously-contacting path on the surface of the device (that is, a path on the surface that continuously contacts the leading edge of the sheath) of the implantable device, thereby allowing smooth transition of the implantable device into the sheath as the sheath is moved in the particular direction. In some cases, the particular direction is the distal direction (i.e., toward the distal end of the implantable device). In some cases, the particular direction is the proximal direction (i.e., toward the proximal end of the implantable device). In some cases, the implantable device and sheath are configured to achieve the smooth transition when the sheath is moved in either the proximal or distal direction. In some cases, the continuous contact is achieved by using regions or members on the implantable device structure that (a) diverge in the direction, or less than 90 degrees from in the direction, of the sheath's movement and/or a direction normal to the leading edge of the sheath at any given location around the sheath's leading edge; and/or (b) converge in the direction aligned with, or creating no more than a 90 degree angle with, the direction of the sheath's movement and/or a direction normal to the leading edge of the sheath at any given location around the sheath's leading edge; (c) do not diverge or converge at a particular location. In some cases, the above device and sheath configurations may facilitate resheathability and redeployment.

Devices and/or methods may be employed that feature a core structure (e.g., a core wire) made of one or more elastic metals and/or polymers (e.g., Nitinol) that assumes a shape, when implanted into a blood vessel, that causes stretch receptors in the vessel wall to be activated. In some cases, the core structure is surrounded by coiled wire, which causes an increase in bending stiffness of the assembly at a given axial location that is less than the increase that would arise from a corresponding increase in core wire thickness at that location. In some cases, the coiled wire has one or more of the following effects: achieving a more desirable spacing between the assembly and a lumen of a delivery catheter to reduce buckling and/or binding during delivery; improving the radio-opacity of the assembly; and/or achieving a more desirable concentration of force between the assembly and a blood vessel wall. In some cases, another type of augmentation is used instead of or in addition to a coil, including but not limited to a metal or polymer braid. Devices with the core structure, with or without the described coil or other augmentation, may be configured to apply force on a blood vessel wall in any number of sites and/or according to any number of geometric arrangements, including but not limited to any combination of the following: paths following the partial or full circumference of the vessel; paths providing longitudinal connection between different regions of the device; paths that help maintain proper alignment of the device with the blood vessel (e.g., a zig-zag following a generally circumferential path); paths that focus force on a region of the blood vessel wall that contains a high concentration of stretch receptors; paths that promote a generally circular cross-section of the blood vessel at a given longitudinal location. In some cases, the devices are configured to apply force or pressure to a vessel wall that differs between circumferential and/or axial locations in the vessel; in some cases, this variation in force or pressure applied depends on the radius of curvature of the device in its free state, or the difference in the radius of curvature of the device in its free state and the radius of curvature and/or diameter of the vessel, or degree of contact between the device and the vessel or the stiffness of the device at a given location, for example due to the device shape and/or material properties.

In some cases, variations in the nature and amount of interaction between the device and the blood vessel that occur during the cardiac cycle provide advantageous activation or lack of activation of baroreceptors in the vessel wall. In some cases, the cardiac cycle promotes variations in interactions due to the changing effective cross section of the vessel, which may cause variations in forces and pressures between the device and vessel wall. In some cases, these variations occur because of the changes in device geometry allowed by changes in the vessel cross section, the changes in device geometry allowing changes in the forces and pressures between the device and vessel wall. In some cases, these variations occur because the amount of mechanical interaction between the vessel and device vary during the cardiac cycle.

Devices and/or methods may be employed that utilize both (a) resorbable, dissolvable, and/or degradable components (hereafter, "shorter-term components"), as well as (b) components intended to resorb, dissolve, and/or degrade over a longer period or not at all (hereafter, "longer-term components"). In some cases, shorter-term components function in part or whole to secure a device in a desired location within a vessel until the device has become incorporated into the vessel wall, after which the shorter-term components resorb, dissolve, and/or degrade, after which longer-term components promote advantageous reshaping of a vessel, and/or advantageous concentrations of stress and/or strain in a vessel. For example, the longer-term components may pull the vessel wall radially inward at one or more locations, and/or provide strain relief in the vessel wall, and/or create or promote stress and/or strain concentrations in the vessel wall, and/or change the magnitude, direction, and/or location of momentum transfer between flowing blood and the vessel wall, causing one or more of the following: strains at all blood pressures occurring within the cardiac cycle are increased; strains at higher blood pressures occurring within the cardiac cycle are increased more (in absolute increase, by percentage increase, or both), than strains at lower blood pressures occurring within the cardiac cycle are increased; strains at lower blood pressures occurring within the cardiac cycle are increased more (in absolute increase, by percentage increase, or both), than strains at higher blood pressures occurring within the cardiac cycle are increased; strains at higher blood pressures occurring within the cardiac cycle are increased, while strains at lower blood pressures occurring within the cardiac cycle are unchanged or minimally increased or minimally decreased or changed by a lesser amount than strains at the higher blood pressures are changed; strains at lower blood pressures occurring within the cardiac cycle are increased, while strains at higher blood pressures occurring within the cardiac cycle are unchanged or minimally increased or minimally decreased or changed by a lesser amount than strains at the lower blood pressures are changed; or strains at lower blood pressures occurring within the cardiac cycle are decreased, while strains at higher blood pressures occurring within the cardiac cycle are unchanged or minimally increased or minimally decreased or changed by a lesser amount than strains at the lower blood pressures are changed.

In some cases, while the vessel diameters promoted by the device during the cardiac cycle may differ between at least two longitudinal locations within the blood vessel, the cross-section of the vessel remains substantially circular during part or all of the cardiac cycle.

Devices described herein may be made by a number of methods. In some cases, devices described herein may be made by removing material from a cylindrical tube, leaving a first structure. In some cases, the removal of material may be achieved by laser cutting. In some cases, the first structure may be expanded radially (by, for example, positioning it over a mandrel) and heat-treated to promote a different diameter (in many cases, an expanded diameter) when the structure is free of constraining loads.

Devices described herein may feature regions, struts, and/or members that have edges and/or surfaces that have been etched, electropolished, drug-coated, drug-embedded, or otherwise treated. In some cases, the etching, electropolishing, drug-coating, drug-embedding, or otherwise treating causes the edges to be more rounded, and/or the surfaces to be more smooth, which in some cases may promote a desired increase or reduction in hyperplasia, thrombosis, endothelialization, or other biological or chemical events or responses, after devices are implanted into a human body.

In some cases, devices and/or methods may be employed that feature a balloon-expandable implantable device, with the balloon positioned on a vascular catheter. In some cases, surgical tools are used that enable implantation via a surgical incision in the region of the head or neck.

Radio-opaque markers may be positioned on devices, to assist operators in determining the location of devices within the vascular system.

Devices and/or methods may be employed which alter the chemical, biological, and/or mechanical properties of tissues of blood vessels and/or tissues surrounding blood vessels, and/or the structural characteristics of blood vessels and/or surrounding tissues, in order to effect changes in the strain occurring at some or all baroreceptors within the vicinity of the alterations.

In some cases, the alterations may be created during a predetermined portion of the cardiac cycle. In some cases, the portion may include diastole. In some cases, the cross-section of a blood vessel in the vicinity of the target tissue may be modified prior to applying a tissue alteration. In some cases, the modification may decrease the blood vessel cross-section. In some cases, the modification may increase the blood vessel cross-section. In some cases, the modification may change the shape of the blood vessel cross-section, for example, to a more oval shape, or to a more square shape, or to a more triangular shape. In some cases, the modification may be partially or fully achieved by occluding flow upstream of the target tissue alteration site.

In some cases, the modification utilizes a flow occlusion mechanism, such as a balloon, deployed proximal and distal to the target tissue.

In some cases, suction may be applied between proximal and distal mechanisms for flow occlusion and/or volume isolation. In some cases, suction may result in apposition of the blood vessel wall to members that promote a desired shape and/or enable tissue alteration. In some cases, suction is provided by an external vacuum source made to engage with the proximal end of an intravascular device, which is in some cases a syringe or syringe-like device, such as an insufflator.

In some cases, a shunt may be provided with a lumen proximal to the proximal flow occlusion mechanism and a lumen distal to the distal flow occlusion mechanism, thereby enabling blood flow to bypass the target tissue region In some cases, the modification of the blood vessel cross-section enables or helps enable alteration of the blood vessel such that blood vessel dilation (as occurs during systole) introduces stress concentrations which increase activation of stretch receptors In some cases, modification of the blood vessel cross-section enables tissue alteration that results in altered tissues that are stressed disproportionately more at systolic pressures than at diastolic pressures. In some cases, the modification is achieved in part or whole by limiting the target tissue's exposure in part or whole to pulse pressure. In some cases, suction may be applied to a subset of the vessel wall that is intended to be moved to achieve a desired cross-sectional profile, as for example by engaging the vessel wall with a lumen opening, the lumen being negatively pressurized.

In some cases, methods and/or devices will be used to confirm that blood vessel wall tissue has been properly engaged for blood vessel cross-section modification. In some cases, the confirmation utilizes methods and/or devices described elsewhere in this document for achieving apposition between (a) devices or portions of devices, and (b) a blood vessel wall and/or tissues targeted for alteration.

In some cases, the alterations include stiffening of a region of a blood vessel and/or its surrounding tissues. In some cases, the alterations of tissue may be (a) performed using a catheter-utilizing system delivered intravascularly, and/or (b) performed using tools introduced via surgical incision and delivered to an extravascular site, with a tissue-modifying element positioned extravascularly at the time of tissue modification, and/or (c) performed using tools introduced via surgical incision and delivered to a vascular site, with a tissue-modifying element passing at least partly through a vascular wall at the time of tissue modification, and/or (d) performed using a catheter-utilizing system delivered intravascularly, with a tissue-modifying element passing at least partly through a vascular wall to reach tissues targeted for alteration. In some cases, the alterations are performed while an embolic protection device and/or system is utilized. In some cases, the alterations include formation of scar tissue and/or cell death and/or tissue emulsification and/or loss of nuclei and/or collagen denaturation and/or protein denaturation and/or tissue desiccation and/or alteration of proteins and/or formation or destruction of cross-linkages between structural components of tissues In some cases, the changes cause a change in activation profile of some or all baroreceptors within the vicinity of the alterations during the cardiac cycle that is characterized by one or more of the following: strains at all blood pressures occurring within the cardiac cycle are increased; strains at higher blood pressures occurring within the cardiac cycle are increased more (in absolute increase, by percentage increase, or both), than strains at lower blood pressures occurring within the cardiac cycle are increased; strains at lower blood pressures occurring within the cardiac cycle are increased more (in absolute increase, by percentage increase, or both), than strains at higher blood pressures occurring within the cardiac cycle are increased; strains at higher blood pressures occurring within the cardiac cycle are increased, while strains at lower blood pressures occurring within the cardiac cycle are unchanged or minimally increased or minimally decreased or changed by a lesser amount than strains at the higher blood pressures are changed; strains at lower blood pressures occurring within the cardiac cycle are increased, while strains at higher blood pressures occurring within the cardiac cycle are unchanged or minimally increased or minimally decreased or changed by a lesser amount than strains at the lower blood pressures are changed; or strains at lower blood pressures occurring within the cardiac cycle are decreased, while strains at higher blood pressures occurring within the cardiac cycle are unchanged or minimally increased or minimally decreased or changed by a lesser amount than strains at the lower blood pressures are changed.

When describing blood pressure, the phrase "highest local blood pressure" may be used to describe the highest blood pressure over the course of a cardiac cycle in a local region of vasculature in the vicinity of a baroreceptor. Likewise, the phrase "lowest local blood pressure" may be used to describe the lowest blood pressure over the course of a cardiac cycle in a local region of vasculature in the vicinity of a baroreceptor.

Alterations of the chemical, biological, and/or mechanical properties of tissues of blood vessels and/or tissues surrounding blood vessels, and/or the structural characteristics of blood vessels and/or surrounding tissues, may be achieved by one or more of the following: providing ultrasound energy; providing microwave energy; providing radiofrequency energy; or providing X-ray energy.

Reducing the temperature of target tissues, as for example by one or more of the following methods: delivery of a cold fluid to a site near the target tissue; creation or facilitation of an endothermic chemical reaction at a site near the target tissue, or in order to cool materials to delivered to a site near the target tissue; externally-applied cooling, as for example to supplement other means of cooling.

Increasing the temperature of target tissues, as for example by one or more of the following methods: delivery of a heated fluid to a site near the target tissue; providing ultrasound energy; providing microwave energy; providing radiofrequency energy; creating or facilitating an exothermic chemical reaction at a site near the target tissue, or in order to heat materials to be delivered to a site near the target tissue; providing light; providing exposure to a laser; providing vibrations, including but not limited to vibrations that correspond to resonant frequencies of target structures; delivering radiation to target tissues; or mechanical agitation or friction.

In some embodiments, the power levels of electrodes delivering radiofrequency energy may fall within the range of 0.1 to 100 Watts per electrode, or in some cases, 0.5 to 8 Watts per electrode. In some embodiments, elements acting to heat target tissues may reach temperatures of 40 to 80 degrees Celsius, or in some cases, 65 to 75 degrees Celsius. In some embodiments, elements acting to cool target tissues may achieve temperatures of 0 to −85 degrees Celsius, or in some cases, −70 to −80 degrees Celsius. In some embodiments, devices acting to cool target tissues may achieve temperatures that alter tissues for a shorter period of time, in order to evaluate or predict the effect of altering the tissue for a longer period of time (including permanent alteration). In some embodiments, the shorter-term alteration may be achieved at temperatures between 0 and −30 degrees Celsius, or in some cases, at approximately −10 degrees Celsius. In some embodiments, elastase, collagenase, and/or other chemical agents may be used to achieve a desired tissue alteration.

Alterations may be performed sequentially and/or simultaneously. Alterations may be performed by repositioning part or all of the enabling device. A balloon filled with fluid for improved acoustic coupling of the device with the anatomy may be used. A balloon that engages the wall of a blood vessel may be coated with a chemical agent that, after contacting the blood vessel, acts to achieve a tissue alteration. The coating may be applied to the balloon in a geometric arrangement that corresponds to a desired geometric arrangement of tissue alterations. A balloon that engages the wall of a blood vessel may be configured to release a chemical agent at one or more desired locations along the surface of the balloon, in order to achieve tissue alterations at locations that correspond to the sites of chemical agent release. A balloon or other structure that acts to define a location of one or more device components relative to a vessel wall may be used to achieve a desired focal length for delivery of energy and/or tissue alteration.

An intravascular device may include one or more tissue penetrating elements such as needles. Upon deployment, the tissue penetrating elements may penetrate the vessel wall and release a chemical agent. The chemical agent may be released preferentially in one or more radially-defined regions of a blood vessel and tissues surrounding a blood vessel, including the following regions: intima, media, and adventitia. An intravascular device may include a proximal flow obstruction mechanism, such as a proximal balloon, and a distal flow obstruction mechanism, such as a distal balloon. After locating the catheter such that the target tissue is aligned with the region between the proximal and distal flow obstruction mechanisms, the proximal and distal flow obstruction mechanisms may be deployed, and a chemical agent may be released from a lumen axially located between the flow obstruction mechanisms. Once a target time has elapsed, suction may be applied in the vessel between the flow obstruction mechanisms, thereby reducing the amount of the chemical agent in the blood vessel. In some cases, devices and/or methods may be used that provide or enable feedback to a user and/or to an electronic tissue modification protocol regarding forces, pressure, and/or energy applied to tissues by the devices. In some cases, devices and/or methods may be used that provide or enable feedback regarding apposition of one or more parts of the device to the wall of the blood vessel.

In some cases, energy delivery methods used to alter the tissue, such as radiofrequency ablation, may be pulsed or cycled to limit undesired tissue damage such as in some cases char formation; in some cases, devices may utilize battery power. In some cases, devices feature batteries contained within a unit or units that also acts as a handle. In some cases, devices may feature batteries contained within a unit or units that are connected to a catheter and/or device handle that is distinct from the structure or component containing a battery. In some cases, devices are powered from a unit that is powered or has been powered from a wall electrical outlet.

In some cases, devices and/or methods may be used that protect some tissues from alteration or an extent of alteration, while other tissues are deliberately altered. An inflatable component may be partly or fully filled with a fluid that is cooler than surrounding tissues or device elements, and/or which acts to draw heat away from tissues that are to be protected or from structures which contact tissues that are to be protected. Fluid that is cooler than surrounding tissues or device elements may be injected into the blood vessel at or near the site of intended alteration. A material or structure may be positioned to physically separate an electrode or other energy source from direct contact with tissue that is not targeted for alteration, or to achieve a separation that is conducive to delivering a desired amount of energy and/or altering effect. When heating is used as a mechanism for altering targeted tissue, cooling may be used as a mechanism to prevent alteration of non-targeted tissue. When cooling is used as a mechanism for altering targeted tissue, heating may be used as a mechanism to prevent alteration of non-targeted tissue.

In some cases, devices and/or methods may be utilized that feature atraumatic and/or flexible distal tips and/or tissue apposition region(s). In some cases, devices and/or methods may be utilized that feature a substantially non-cylindrical profile. In some cases, devices and/or methods may be utilized that promote a tapered and/or frustoconical vessel profile during tissue alteration. In some cases, devices and/or methods may be utilized that promote a noncircular vessel profile (such as an elliptical vessel profile) during tissue alteration In some cases, devices and/or methods that achieve the alterations may include a temperature measurement element and tissue modification element (such as radiofrequency electrode). The temperature measurement element may be located in close proximity to and/or integrated within the tissue modification element. Based on data from the temperature measurement element, a control algorithm may modify parameters of tissue alteration in order to reach or maintain a target temperature. When heating is used as a mechanism for altering targeted tissue, a measured temperature in excess of a threshold value, for example 75 degrees Celsius, may trigger a change in rate or degree of heating, such as the cessation of heating. When cooling is used as a mechanism for altering targeted tissue, a measured temperature below a threshold value may trigger a change in rate or degree of cooling, such as the cessation of cooling.

In some cases, devices and/or methods that achieve the alterations may utilize measurement(s) to determine whether the mechanism for altering the targeted tissue is properly located relative to the targeted tissue. In some cases, impedance measurements may be conducted to determine whether proper engagement with the target tissue has been achieved at each site. In some cases, a device may contain an element to measure contact force and/or pressure and/or strain to determine whether proper engagement with the target tissue has been achieved.

In some cases, devices feature elements for measuring tissue engagement at multiple locations. In some cases, the locations each correspond to tissue modification element(s). The devices may indicate to the user whether proper engagement with the target tissue has been achieved at each of the locations. In some cases, if fewer than all of the locations are measured to have proper tissue engagement, the user may be prompted with an option to reposition. In some cases, if fewer than all of the locations are measured to have proper tissue engagement, tissue modification may be restricted to regions in the vicinity of locations measured to have proper tissue engagement. Tissue modification elements in the vicinity of locations measured to lack proper tissue engagement may not activate.

In some cases, devices and/or methods that achieve the alterations may enable measurement of contact force and/or pressure and/or strain and/or impedance in the vicinity of the target tissue, and adjustment of the delivery of the tissue alteration based on this data. For example, with devices with radiofrequency electrode(s), the power delivered to the electrodes and/or the length of time of delivery of tissue alteration therapy may be adjusted based on this data.

In some cases, devices and/or methods that achieve the alterations may utilize one or more electrodes to provide energy to target tissues. An electrode may be used near or at the distal end of a catheter, which relies on a grounding component that is placed non-invasively on a patient and/or breaches the skin. A device may include a return path contained within the catheter and/or its distal apparatus. An electrode may resemble a stent-like device, which creates alterations in some or all of its structure made to contact blood vessel tissue. Some or all of the wire may be insulated to achieve a desired conductive path and/or targeting of tissue alteration. An electrode may be monopolar or bipolar. A device may utilize structures within a delivery catheter to provide part or all of a conductive path. An electrode may resemble a substantially continuous wire made to extend from a catheter. Some or all of a wire and/or conductive path that comprises or connects to an electrode may be exposed to facilitate and/or localize alteration of tissue, and some may be insulated to prevent and/or localize alteration of tissue. Some or all of a wire and/or conductive path that comprises or connects to an electrode may be insulated to establish and/or preserve a desired electrically conductive pathway and/or to focus the region of alteration. One or more electrodes may comprise and/or be positioned upon expandable members that assume positions in proximity and/or contact with a vessel wall. These electrodes may be constrained within a catheter structure or component before and/or after they are positioned to deliver energy to tissue. Some or all electrodes may be made to contact the targeted tissue, while some or all electrodes may be positioned such that they do not contact the targeted tissue. Some or all electrodes may be made to contact the blood vessel wall, while some or all electrodes may be positioned such that they do not contact the blood vessel wall. Some or all electrodes may be mounted on (including on the surface of) or within an expandable structure, which facilitates a desired position of the electrodes relative to target tissues (for example, direct contact between electrodes and a vessel wall). An expandable structure may be utilized that allows some blood flow to continue during tissue alteration. Examples of the expandable structure include a balloon, a low-pressure balloon, a compliant balloon, a substantially non-compliant balloon, and a Nitinol basket. Nitinol members may be used to position electrodes, for example against a vessel wall. A grounding element may be used that desirably focuses or disperses the current pathway in order to localize alteration effects to desired locations In some cases, desired relative distances between electrodes and target tissues, and/or desired locations of electrodes, are achieved by one or more of the following devices or methods. One or more electrodes may be mounted onto or incorporated into or contained within an inflatable structure, which when inflated, positions the one or more electrodes at a desirable location. One or more electrodes are positioned at the generally distal end of a catheter. One or more electrodes may be positioned on a self-expanding structure. The structure may itself be fully or partly comprised of electrodes and/or conductive paths to electrodes. The structure may resemble a self-expanding stent. In some cases, part or all of the structure is insulated. In some cases, an operator may change the degree of device contact with and/or energy delivery to the vessel wall by varying the extent to which the structure has been advanced beyond the distal end of a delivery catheter. In some cases, strands of the structure are secured at a generally distal location in a manner that provides desired insulation or electrical connection to achieve desired conductive paths. An electrode mounted on the generally distal end of a device is advance through a catheter and directed to contact a vessel wall. A generally curved member is advanced from or beyond the generally distal end of a catheter and assumes contact with the blood vessel conducive to energy delivery.

In some cases, an ultrasound transducer may be positioned within an expandable structure, such as a balloon, and utilized to deliver ultrasound energy to targeted structures. The expandable structure may be used to control the distance between the ultrasound transducer and the vessel wall and/or to center the transducer within the vessel. In some cases, the expandable structure comprises an inflatable structure, and in some cases, a cooling fluid may fill part or all of the inflatable structure. A pleating pattern may be used that promotes engagement of electrodes with the vessel wall, even when the balloon is not completely inflated. Feedback may be provided to the user on whether sites for creating alteration are engaged with tissue.

Characteristics or characterizations of the alterations may include one or more of the following: lesions, including those that may be created by medical ablation tools; scarring; removal of tissue; destruction of tissue; a tissue response resulting from introduction of a foreign body and/or material; cutting of tissue.

The alteration may take place through the full depth of a tissue, or through a partial depth only. The alteration may take place preferentially in one or more radially-defined regions of a blood vessel and tissues surrounding a blood vessel, including the following regions: intima, media, and adventitia. In some cases, devices and/or methods will utilize an over-the-wire guide wire structure. In some cases, devices and/or methods will utilize a rapid-exchange guide wire structure. Alterations may affect any combination of tissue types found within or around the blood vessel, including but not limited to one or more of the following: the intima, media, adventitia, surrounding tissues, or distinct cell types found within these tissues. Alterations may create stress redistributions by increasing the stiffness of some tissues and/or decreasing the stiffness of some tissues. Alterations may be similar to lesions created in cardiac tissue during ablation procedures. Alterations may be permanent or temporary. Alterations may be concentrated on a side of a vessel and/or within an axial region of a vessel where baroreceptors are thought, determined, or known to be concentrated Devices and methods may be used may be used which locally release chemical agent(s) to reduce and/or control pain and/or discomfort during procedures and/or interventions described in this document. The chemical agent(s) may be deployed before, and/or during and/or following the delivery of therapy. In some cases, the chemical agent(s) may include lidocane. In some cases, a balloon that engages the wall of a blood vessel may be configured to release the chemical agent(s) at one or more desired locations along the surface of the balloon. In some cases, a balloon that engages the wall of a blood vessel may be coated with the chemical agent(s) that is transferred to the wall of the blood vessel after expansion.

In some cases, an intravascular device may include tissue penetrating elements. The tissue penetrating elements may be deployed from a first position to a second position in which penetration of the wall of a blood vessel is achieved. The chemical agent(s) may be released via the tissue penetrating elements into the wall of the blood vessel and/or tissues surrounding the blood vessel.

The invention claimed is:

1. A method of treating a wall of an artery in a patient, to facilitate activation of a baroreceptor in or adjacent the wall of the artery, the method comprising:
   advancing a treatment portion of a flexible, elongate treatment delivery device into the artery to position the treatment portion at or near the baroreceptor;
   expanding the treatment portion to contact the wall of the artery;
   delivering a treatment from the treatment portion to the wall of the artery, to increase a stiffness of a first portion of the wall of the artery; and
   removing the treatment delivery device from the artery, without leaving any implant in the artery,
   wherein the stiffness of the first portion of the wall of the artery remains increased after the treatment, and
   wherein the stiffness of the first portion of the wall of the artery is increased by the treatment such that a post-treatment strain in a second portion of the wall of the artery at or near the baroreceptor is increased relative to a pre-treatment strain.

2. A method as in claim 1, wherein delivering the treatment comprises delivering a treatment selected from the group consisting of radiofrequency energy, microwave energy, ultrasound energy, X-ray energy, cryotherapy, light energy, laser energy, a chemical treatment and a mechanical alteration.

3. A method as in claim 1, further comprising, before advancing the treatment portion into the artery, assessing a likelihood of success of the method.

4. A method as in claim 3, wherein assessing the likelihood comprises:
   reversibly altering the stiffness of the first portion of the wall of the artery; and
   measuring a physiological parameter of the patient to determine whether the altering of the stiffness has caused a desired effect.

5. A method as in claim 1, further comprising protecting a non-treatment portion of the artery with a protective portion of the treatment delivery device at least one of before or during delivering the treatment.

6. A method as in claim 1, further comprising allowing blood to flow past a portion of the treatment device within the artery, while the method is being performed.

7. A method as in claim 1, wherein the artery is an internal carotid artery, wherein the baroreceptor is a carotid baroreceptor, and wherein delivering the treatment helps to reduce systemic blood pressure in the patient.

8. A method as in claim 1, further comprising:
   measuring an amount of the treatment delivered to the artery; and
   providing feedback to a user regarding the measured amount of the treatment.

9. A method as in claim 1, wherein delivering the treatment comprises delivering the treatment asymmetrically to a circumference of the wall of the artery, such that a portion of the wall closer to the baroreceptor receives more treatment than a portion of the wall farther from the baroreceptor.

10. A method as in claim 1, wherein delivering the treatment causes a greater increase in the post-treatment strain in the second portion of the wall of the artery during a high-pressure portion of a cardiac cycle of the patient than during a low-pressure portion of the cardiac cycle.

11. A method as in claim 10, wherein the high-pressure portion of the cardiac cycle comprises a systolic portion, and wherein the low-pressure portion of the cardiac cycle comprises a diastolic portion.

12. A method as in claim 10, wherein delivering the treatment causes an increase in the post-treatment strain in the second portion of the wall of the artery during the high-pressure portion of the cardiac cycle and causes no increase in the post-treatment strain during the low-pressure portion of the cardiac cycle.

13. A method as in claim 1, wherein delivering the treatment comprises increasing the stiffness of multiple portions of the wall of the artery in a geometric arrangement.

14. A method as in claim 13, wherein the geometric arrangement comprises multiple rows, and wherein at least one of the multiple rows is offset from another of the multiple rows.

* * * * *